US009034573B1

(12) United States Patent
Flegel et al.

(10) Patent No.: US 9,034,573 B1
(45) Date of Patent: May 19, 2015

(54) MOLECULAR STRUCTURE OF RHD NEGATIVE

(75) Inventors: Willy A. Flegel, Dieburg (DE); Franz F. Wagner, Ulm (DE)

(73) Assignee: DRK-BLUTSPENDEDIENST BADEN-WURTTEMBERG-HESSEN GEMEINNUTZIGE GMBH, Ulm (DE)

( * ) Notice: Subject to any disclaimer, the term of this patent is extended or adjusted under 35 U.S.C. 154(b) by 1120 days.

(21) Appl. No.: 10/129,580

(22) PCT Filed: Oct. 31, 2000

(86) PCT No.: PCT/EP00/10745

§ 371 (c)(1), (2), (4) Date: Nov. 12, 2002

(87) PCT Pub. No.: WO01/32702

PCT Pub. Date: May 10, 2001

(30) Foreign Application Priority Data

Nov. 2, 1999 (EP) .................................... 99121686
May 31, 2000 (EP) .................................... 00111696

(51) Int. Cl.

| | |
|---|---|
| ***C12Q 1/68*** | (2006.01) |
| ***C12N 15/12*** | (2006.01) |
| ***C12N 15/52*** | (2006.01) |
| *C07H 21/02* | (2006.01) |
| *C07H 21/04* | (2006.01) |

(52) U.S. Cl.

CPC .............. *C12Q 1/6883* (2013.01); *C12N 15/52* (2013.01); *C12Q 2600/172* (2013.01); *C12Q 2600/156* (2013.01)

(58) Field of Classification Search

CPC ...... C12Q 1/6883; C12Q 1/6881; C12Q 1/68; C12Q 1/6827; C12Q 1/6876; C12Q 1/6888; C12Q 2600/112; C12N 15/52

USPC .......................... 536/23.1, 24.33; 435/6, 91.2

See application file for complete search history.

(56) References Cited

U.S. PATENT DOCUMENTS 5,474,796 A * 12/1995 Brennan ...................... 427/2.13
5,654,419 A * 8/1997 Mathies et al. .............. 536/25.4
5,972,602 A 10/1999 Hyland et al. .................... 435/6
6,821,724 B1 * 11/2004 Mittman et al. .................. 435/6

FOREIGN PATENT DOCUMENTS

WO 98/45712 A2 10/1998
WO 99/37763 A2 7/1999
WO 99/47555 A1 9/1999

OTHER PUBLICATIONS

Robles et al (J. Am. Chem. Soc. (1996) 118:5820-5821).*

Kim et al. Molecular cloning and primary structure of the human blood group RhD polypeptide. PNAS, vol. 89, pp. 10925-10929, 1992.*

Okuda, H et al. Sequence analysis of the spacer region between the RHD and RHCE genes. Biochem. Biophys. Res. Commun., vol. 263, pp. 378-383, Sep. 1999.*

Chien-Feng, S et al. RHD gene polymorphisms among RHD-negetive chinese in Taiwan. Vox Sanguinis, vol. 75, pp. 52-57, 1998.*

Lowe et al., A computer program for selection of oligonucleotide primers for polymerase chain reactions. Nucleic Acids Research, vol. 18, No. 7, pp. 1757-1761, 1990.*

Matassi, G. et al. Characterization of the recombination hot spot involved in genomic rearrangement leading to the hybrid D-CE-D gene in the D VI phenotype. Am. J. Hum. Genet., vol. 60, pp. 808-817, 1997.*

Sekizawa et al. Noninvasive prenatal diagnosis using a single fetal nucleated erythrocyte isolated by micromanipulation from maternal blood. Methods Mol Med 1998;16:275-85.*

Zhang et al. Whole genome amplification from a single cell: implications for genetic analysis. Proc Natl Acad Sci USA 1992;89:5847-51).*

(Continued)

*Primary Examiner* — Teresa E Strzelecka

(74) *Attorney, Agent, or Firm* — Pillsbury Winthrop Shaw Pittman LLP

(57) ABSTRACT

The RH blood group antigens derive from two genes, RHD and RHCE, that are located at chromosomal position 1p34.1-1p36. In whites, a "cde" haplotype with a deletion of the whole RHD gene occurs with a frequency of about 40%. The relative position of the two RH genes and the location of the RHD deletion was previously unknown. A model for the RH locus was developed using RHD- and RHCE-related nucleotide sequences deposited in nucleotide sequence databases along with PCR and nucleotide sequencing. The open reading frames of both RH genes had opposite orientations. The 3' ends of the genes faced each other and were separated by about 30,000 base pairs (bp) that contained the SMP1 gene. The RHD gene was flanked by two DNA segments, dubbed Rhesus boxes, that had about 9,000 bp length, 98.6% homology, and identical orientation. The Rhesus box contained the RHD deletion occurring within a stretch of 1,463 bp of identity. A PCR-SSP and a PCR-RFLP for specific detection of the RHD deletion was devised. The molecular structure of the RH gene locus explains mechanisms for generating RHD/RHCE hybrid alleles and the RHD deletion. Specific detection of the RHD negative genotype is now possible. The utility of the RHD PCR is limited by the incomplete knowledge of presumably rare RHD positive alleles in D negative. 1068 serologically RhD-negative samples were checked by PCR-SSP for the presence of RHD specific nucleotide sequences. 48 Samples were positive and were then assigned to specific PCR patterns or distinct RHD alleles. Seven PCR patterns were identified, three of which were not described previously, and four new RHD alleles that were RhD-negative because of nonsense or splice mutations. Another three new haplotypes represented a $D_{el}$ phenotype. Three samples were mislabeled weak D or partial D. The sensitivity of current RHD PCR methods exceeded routine serology. As the molecular background of D-negative alleles causing false-positive RHD PCR in whites is more heterogeneous than anticipated, improvements in test specificity will critically depend on detecting RhD-negative RHD positive alleles.

5 Claims, 37 Drawing Sheets

(56) References Cited

OTHER PUBLICATIONS

Figure 1:
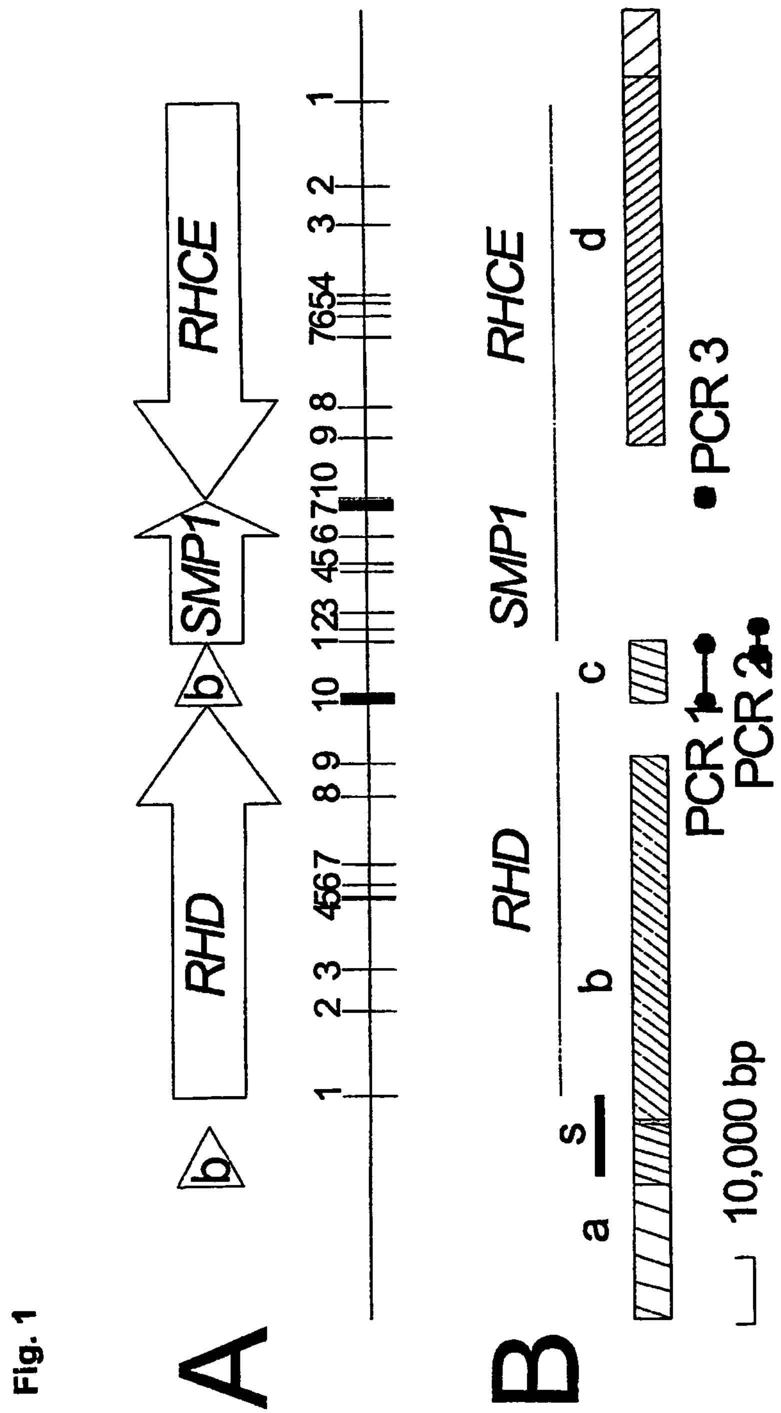

Grothues et al. PCR amplification of megabase DNA with tagged random primers (T-PCR). Nucleic Acids Research 1993;21(5) 1321-2.*

Warren et al. Principles and methods for the analysis and purification of synthetic deoxyribonucleotides by high-performance liquid chromatography. Molecular Biotech 1999;4:179-99.*

Cobley, V., et al., Human DNA sequence clone RP3-469D22 on chromosome 1p35. 1-36.13, contains the 5'part of the gene for RHCE, Database EM_HUM Online! EMBL; Aug. 1998, p. 1-3, retrieved for EBI, accession No. HS469D22, Data base accession No. AL031284, XP002178290.

Blunt, T., et al., Serotype switching in a partially deleted RHD gene, Vox Sanguinis, vol. 67, No. 4, 1994, pp. 397-401, XP000926512.

Avent, N.D., et al., Evidence of genetic an diversity underlying RhD-, weak D (Du), and partial D phenotypes as determined by multiplex polymerase chain reaction analysis of the RHD gene, Blood, W.B. Saunders, Philadelphia, VA., US, vol. 89, No. 7, Apr. 1997, pp. 2568-2577, XP002108680, ISSN 0006-4971.

Carritt, B., et al., Evolution of the Human RH (Rhesus) Blood Group Genes: a 50 Year Old Prediction (Partially) Fulfilled, Human Molecular Genetics, 1997, 6(6), 843-850.

Carritt, B., et al., Rh Null Phenotypes Are Not Due to a Gross Deletion and Can Occur on Different Rh Genetic Backgrounds, Ann. Hum. Genet., 1993, 57, 273-279.

Cherif-Zahar, B., et al., Organization of the Gene (RHCE) Encoding the Human Blood Group RhCcEe Antigens and Characterization of the Promoter Region, Geneomics, 1994, 19-68-74.

Hu, G., Human Small Membrane Protein 1 (SMP1) mRNA, EMBL Sequence Database, XP002170737, Heidelberg De cited in the application Accession No. AF081282,.

Okuda, Hiroshi, et al., Sequence Analysis of the Spacer Region between the RHD and RHCE Genes, Biochemical and Biophysical Research Communications, 1999, 263, 378-383.

Singleton, Belinda K., et al., The Presence of an RHD Pseudogene Containing a 37 Base Pair Duplication and a Nonsense Mutation in Africans with the Rh D-negative Blood Group Phenotype.

Wagner, Franz F., et al., RHD Gene Deletion Occurred in the Rhesus Box, Blood, 2000, 95:12, 3662-3668.

Daniels, G., "Human Blood Groups," Molecular Genetics of the Dipolymorphism, European/African/Asians, 2002, pp. 204-206.

Daniels, G., "Human Blood Groups," Molecular Genetics of the Dipolymorphism, European/African/Asians, 2002, pp. 208-209.

Daniels, G., "Human Blood Groups," Molecular Genetics of the Dipolymorphism, European/African/Asians, 2002, pp. 218-219, 221-223.

Flegel, W.A., "The Genetics of Rhesus Blood Group System", Dtsch Arztebl, 2007, 104(10):A 651-7.

Flegel, W.A., "Genetik des Rhesus-Blutgruppensystems", Dtsch Arztebl, 2007, 104(10):A 651-7.

Okuda, H., et al., "The RHD Gene is Highly Detectable in RhD-negative Japanese Donors," Journal of Clinical Investigation, 1997, 11(2):373-379.

Reid & Lomas-Francis, "Rh Blood Group System," The Blood Group Antigen FactsBook, 2004, pp. 109-110.

Wagner, F.F., et al., "Molecular Basis of Weak D Phenotypes", Blood, 1999, 93(1):385-393.

Wagner, F.F., et al., "RHD Gene Deletion Occurred in the Rhesus Box", Blood, 2000, 95(12):3662-3668.

Flegel, W.A., et al., Rh Phenotype by DNA Typing and its Application to Practice, Transfusion Medicine, 8:281-302 (1998).

Gassner, C., et al., RHD/CE Typing by Polymerase Chain Reaction Using Sequence-Specific Primers, Transfusion, 37:1020-1026 (1997).

Beckers, E.A.M., et al., Characterization of the Hybrid RHD Gene Leading to the Partial D Category IIIc Phenotype, Transfusion, 36:567-574 (1996).

Cherif-Zahar, B., et al., Molecular Defects of the RHCE Gene in Rh-Deficient Individuals of the Amorph Type, Blood, 92(2):639-646 (1998).

* cited by examiner

A
B
RHD
SMP1
RHCE
b
b
a
s
b
c
d
PCR 1
PCR 2
PCR 3
10,000 bp

A
B
AGCACAGTTCCGGGAAGTTGGCTGCAG
AGCACAG----GGGAAGTTGGCTGCAG
a
b
c
d
e
5'
ATG 3'
RHCE
RHD
dJ469D22
dJ465N24
1,000 bp
23,130 bp
9,416 bp
6,557 bp
4,361 bp
2,322 bp
1 2 3 4 5 6 7 8 9
Primers
RHD

Fig. 3

```
-- Rhesus box ----------------------------------->
gcatgcgcgactgagccgggtggatggtactgctgcatccgggtgtctg

               <- SMP1 Exon 1 (91 bp, 5'UTR)-------
gaggctgtggccgttttgttttcttggctaaaatcgggggagtgaggcggg

-- SMP1 Exon 1 ----------><--- Intron ~ 2,000 bp
...actgcacgacggggctggactgacgt....................

Intron ---><---- SMP1 Exon 2 (106 bp, 93 translated)-----
........,agctgaaaaaaATGTCTGGATTTCTAGAGGGCTTGAGATGCTCAG...

-- SMP1 Exon 2 ----------><--- Intron ~ 2,500 bp
...GCTTCCATTGCTGCTGGTGTACTAgt...

Intron ----><--- SMP1 Exon 3 (113 bp, all translated)----
..........agTTTTTTACAGGCTGGTGGATTATCATAGATGCAGCTGTTATT...

-- SMP1 Exon 3 ----------><--- Intron ~ 8,000 bp
...TATAGCAACCATAGCCTTCCTAATgt....................

Intron ----><--- SMP1 Exon 4 (68 bp, all translated)-----
..........agGATTAATGCAGTATCGAATGGACAAGTCCGAGGTGATAGTTA...

-- SMP1 Exon 4 ----------><--- Intron ~ 1,400 bp
...TGAAGGTTGTCTGGGTCAAAACAGgt....................
```

Fig. 3 cont.

```
Intron ---->   <--- SMP1 Exon 5 (93 bp, all translated)-----
..........agGTGCTCGCATTTGGCTTTTCGTTGGTTTCATGTTGGCCTTTG...

-- SMP1 Exon 5 ----------->   <--- Intron ~ 4,000 bp
...TTTTTGGAGGTTATGTTGCTAAAGgt.....................

Intron ---->   <--- SMP1 Exon 6 (61 bp, all translated)-----
..........agAAAAAGACATAGTATACCCTGGAATTGCTGTATTTT.........

-- SMP1 Exon 6 ----------->   <--- Intron ~ 4,000 bp
...TCCAGAATGCCTTCATCTTTTTTGgt

Intron ---->   <--- SMP1 Exon 7 (1,703 bp, 47 translated)---
..........agGAGGGCTGGTTTTTAAGTTTGGCCGCACTGAAGACTTATGGCAGT

                 <---------- RHCE Exon 10 -----
-- SMP1 Exon 7 ------------------------------
GAacac....agcatcatcctaatgaaactaaacatttattttaaac

---------- RHCE Exon 10 ---------------------------
------- SMP1 Exon 7 --->
ttattaaattgactcttaaactaagtttttagtctttaatttttaatatcaa

                                >---- Homology with RHD -
-- RHCE Exon 10 -------------------------------------
atctgtctctgaccttgtttcattatacataaggagctttgctgtcatgagcgtttc
```

Fig. 3 cont.

```
---------- Homology with RHD --------------
------------- RHCE Exon 10 ----------------
tcacgtacaaatgcaggcaacagtgagaggaagttgtcttgtt

-- Homology with RHD ---------------------------------------
-- RHCE Exon 10 --------------------------------------------
tttgaacaggccttgtttttcttggatgcttttgcTTAAAATCCAACAGCCAAATGAGG
```

Fig. 5

```
attcactatcacaagaacagcacgggtaa
*****************************
**-*********g****************

  -------rez7----------->
gacctgtccccatgattcagttacct
**************************
**************************

cccactgggtccctcccacaacgcatgggaattcaggatgagattt
**********************************************
**********************************************

gggtggggacacaaccaaaccctatcattccacccatggcccctcccaaa
**************************************************
**************************************************

tttcatgtcctcacatttcaaaaccaatcacaccatcccaacagtccctc
**************************************************
**************************************************

aaagtcttaaatgatttcagcattaactcaaaagtccacagtctaatgtc
**************************************************
**************************************************
```

Fig. 5 cont.

```
tcatctgagacaaggcaagtcctttccatttatgagcctataaaatccaa
**************************************************
*****************************c********************

agcaagttagttacttcctagatacaatggggg tacaggcattgggtaaa
**************************************************
*********a****************************************

tacagccattccaaatgggataaattggtcaaaacaaagaggctacaggc
**************************************************
**************************************************

ccatgagagtccaaaatccagtggggcagtcaaatcttaaagctccaaaat
***************************************************
***************************************************

gatctcct-ttgactccacatctcacatccaggtcacgcagatggaagg
********_****************************************
********c****************************************

ggtgggttcccatggtcttgggcagctctgcccctgtacctttgcagggt
**************************************************
**************************************************
```

Fig. 5 cont.

```
acagcctccctctcagctgctttcatgggctggcattgagtgtctgcagc
**************************************************
************************************************a*
                                           ^^^^^^

ttttccaggtacacggtgcaagctgtcggtggatctaccattctggggtc
**************************************************
**************************************************

tggaggacctcttctcacagctccactaggtggtgccccagtagggactg
**************************************************
**************************************************

tgtggggtctctgaccccacatttcccttctgcactgccctggcagag
**************************************************
**************************************************

gatctccatgagggccctgctcctgcagcaaacttctgactgggcatcca
**************************************************
********************c*****************c***********
                      ^^^^^^

ggcatttccgcacatcctctttaatctaggcgaaggtttccaaaccccaa
**************************************************
*************************************************g
```

Fig. 5 cont.

```
ttcttgacttctgtgcactcgcagtctcaacaccacatggaagctgtcaa
**************************************************
**************************************************

ggcttggggcttgcactccccgaagctacagcccaagctctaccttgcct
**************************************************
**************************************************

cccgtcagtcatggttgggagtggctgggatgcagggcaccaagtcccta
**************************************************
**t***********************************************

ggctgcacacagcatgaggaccccgggcctggccaacaaaaccatttttt
**************************************************
**************************************************

        +-- breakpoint region ->
        +-- identity region ->
cctgatacctctggacctgtgatgggaggggttgccataaagacctctga
**************************************************
*******t******************************************

catgccctggagacattttccccattgtcttgggaattagcatttggctc
**************************************************
**************************************************
```

Fig. 5 cont.

```
ctgttactcatgcaaatttctgcagccagcttgaatttctcctcagaaaa
**************************************************
**************************************************
                   ^^^^^^

tgggaatttttcttttctatcacattgtcaggctgcaaattttccgaactt
***************************************************
***************************************************

ttatgctctgcttcccttataaaactgaatgtctttaacagcacccaag
*************************************************
*************************************************

tcacctcttgaatgctttgctgcttagaaatttctcctgccagatactct
**************************************************
**************************************************

aaatcatctctctgaagttcaaagttctacaaatatctcgtgcaggggca
**************************************************
**************************************************

aaatgccgccagtatctttgctaaaacataacaagagtcccctttgctcc
**************************************************
**************************************************
```

Fig. 5 cont.

```
agttcccaacaagttcctcatttccgtctgagaccacctcagcctatgga
**************************************************
**************************************************

ctttattgtccacagtgctatcagcatttgggcaaagccattcaacaag
**************************************************
**************************************************
tctctaggaagttccaaactttcccacatttgcctgtcttcttctgagcc
**************************************************
**************************************************

ctccaaactgttccaaaccctgcctgttacccagttccaaagtcacatac
**************************************************
**************************************************

ccattttgagtatctacggcagcaccccactctactggtaccaatttag
**************************************************
**************************************************

ccactgaagtagttggagaacagaagtaatagactctggtttacattgta
**************************************************
**************************************************

aaagcttctctgtggctgctgtgtgaagaaaatatatgagaatgaagccc
**************************************************
**************************************************
```

Fig. 5 cont.

```
caagatgaagcagggacacagttgcagtggttagagtaagaaatgctgct
**************************************************
**************************************************

ggctggcactgaagtgatagcctggaggtttgtgtgtgcacatgcatgtg
**************************************************
**************************************************

tatgtgttttacgatagtaggcccaacagat
*******************************
*******************************

  <-- breakpoint region ----+
actgtaatccacacttgtttttttttttt----ga
*****************************tttt**
*****************************tttt**

gacagagtctcacctgttgcctagactagaatgc
**********************************
**********************************

agtggcacaatcttggctcactacaacctccacctcccaggttcaaacaatc
****************************************************
****************************************************
```

Fig. 5 cont.

```
cttgtgcttcagcctcccgagtagttgggattacaggtgtgtgccacc
************************************************
************************************************

gtgcccagctatatttttgtatttttagcagagatgggatttgccacat
*************************************************
*************************************************

tggccaggctggtcttgaactcctggcctcaagcaatcctcccacctta
*************************************************
*************************************************

gcctcccaaagtgctgagccaccacacctggccgcaactgattttaatc
*************************************************
*************************************************

atgaaatgacacatacatttaaaaacccaatacctataatattcctggc
*************************************************
*************************************************

tagtactcttcacatctatatcatcaaaaacaaagaaagtatgtgaaact
**************************************************
**************************************************
```

Fig. 5 cont.

```
gacacagccaaggggagactaaggagacataacaattaactgtaatgtgg
**************************************************
**************************************************

tattctggaggggatcctggaacagaaaaagacattaggcaaaaaactaa
**************************************************
**************************************************

agaaatctgaataaaatgtggatgtcagttaataataatgtatcatatta
**************************************************
**************************************************

    <-- identity region-+
gtccagtaattgtaacaaatataccacaataatgaaagccattaattata
*************************-************************
*************************-************************

gggaaaatggaggggttaatatgggtggctggcttttgctatttctagcag
***************************************************
***************************************************

ctccattttatctgcaaaagacaaacattcattaagtcccaaaaaggtaaa
*************a*************************************
*************a*************************************
```

Fig. 5 cont.

```
gaatgacaaattaagcatgtatcttattagtaagagtaatataaagatg
*************************************************
*************************************************

ctcactcctatttataaatatttgacaatcatgttaaggccacaaaagag
*******a*********************g************g*******
*******a*********************g************g*******

aaaaaagggtaggggcaaaaaacgcaaagagaaaggagttagtatctttt
**************************************************
**************************************************

ctcccgcactcattagctattaaaagaggatgtttgtttaaagctgctca
**************************************************
**************************************************

gagctggtaaactaatgttaagtcactaacgggaatttaaaggtttcat
**************************************************
**************************************************

taagaactgcctgcactagattcctccaccctgagacattaaacaatcac
**************************************************
**************************************************
```

Fig. 5 cont.

```
gataaacctcctgagtggtaagaacttgtccatttaaaaacaggctatag
************************g*************************
************************g*************************

attgtatcatgcagttttatctactaatcggctaa
*****__****************************
*****__****************************

tatcccgccaaaaac----aaaaaaccccaaa
*gca**********aaac******a******
*gca**********aaac******a******
 <--------rnb31-----------mm

gggatgaaagtttcatccatcaaaggaaacaac
*********************************
*********************************
```

Fig. 8

Hybrid Rhesus box of RHD negatives

```
5' ctagaaaacactttgtcattttagaggtgtta
(start of Rhesus box)
tccaatgttcgcgcaggcactggagtcagagaaaatggagttgaatcctttctctgccactc
tttgaggagaatctcaccatttattatgcactgtagaatacaacaataaaatacagccatgt
accacataacaacatcttggtaaacaacagactgcatatatgatggtggtcatccagtaagc
taaggttaatttattattattcccttttttttttcttttttttgagatgtagtcttactctg
tcacccaggctagagtgcaatggcaccatcttggctcactgcaacctctgcctcctgggttc
aagcgaatctcctgcctcagcctccgaagtagctgggaattacaggcacccaccacatctgg
ctaatttttgtatttttagtaaagatggggtttcaccatgttggccaggctgatctcaaac
tcctgacctcaagtgatctgcctgcctcggcctcccaaagtgctgggaccataggcctgagc
cactgtgcccggccttgtttgctttttaacagttaacagtgtgctcatagaaactgctttg
acatgactgcaatcatgtgcttcatagaaacttaattagattataccactagagtcttcaga
tttttatactttttttttttgaaacggagtctcactctgtcaccaggctggagtgcagtgccg
caatctcagctcgccgcaacctccgcctcccaggttcaagtgattctcctgcctcagcctcc
cgagtagctgggattacaagtgcacactaccacgcccagctaatttttgcatttttactaga
cagggtttcaccatgttggctaggatagtttcaccaggatctcttggcctcatgatcagcct
gcctcggcctcccaaagtgctgggattacaggtgtgagccaccgtgcccagcctatacttcc
ctttttgaataccatttggcgttttgaagaattaacagctttgtgaacgtggcagtgcttgt
gattcaggcttccactgagaccaaggggagaacctggttgcaggacaaacagacggacagcg
tgtggcagtgtttaaatgctcttctgaaggctgatacgacagctctctgtgcactgattgta
tacgcatcccaagattatattattgttttctattgctatgtgtcacactttgccaaacagga
tgtggaaaatgaataagcggttttcttaggcacttcttaacagacaattggtcaaaatgaac
tccattgcttaagaaacacataaacaccatttagtcactgaatatagctatatgtatggttg
ctactatggggaatcttgttttgccaattttctttgaaaattctggcagaccaaggttcttt
ttgtttacacaatacttgaaaaataaaaatgaacaagccaacaaactaccaagttttcactt
acataaatgtagttacatacagaaaatgtgactgtgaatttttttctaggacttttaaactat
aagcactatttgcacgaaagagaaccaatctatcaattacaaactcacataattttacagat
tttttttccctacacagcacataaaacagaaggaatttgaagccaccctccaaacacaggg
gaaggaggctgtgtgtatatcctcattgtctttcacattctaaggtggttccactcagtgac
tgaaatccttaagtgttgtattagtcggcttgggctaccataacagcagcttaaactgttgt
taagccactcagacttaaacaacagaaatttatttccttatagttctggaggctggaagttc
aaggtgccggcaaggctggtttctggtgagacctctctccctgtcttgcagatggctgcctc
ctccctgtgtcctcatagagcctgtcctctgcttttacacttctggtgtcatcttccttttt
tttttttttttgagacagagtctcgctctatcgcccaggctggagtgcagtggcccgatcga
tctcggctcactgcaacctctgcctcccaggttcaagcaattctcctgcctcagcctcccga
gtagctgggactacaggtgcccgccatcatgtctggctaatttttgtatttttagtagagac
agggtttcaccatattggccaggctggtctccaactcctgaccttgtcatctgcctgcctcg
gcctcccaaagtgctaggattacaggcgtgagccaccgcacccggcctctttctcttcttat
aaggacaccagtcctattagattagggctccaccctcatgacctcatttgaccttaactatt
atttctttaaagcacctatttccaaatatagtcactttaggggttagggcttcaaaatatga
atctgagggagatcaattcagtaaatagcagtagtcattaacggacaatatatacaaagata
atttcgtgattactgtccttatgcataaatgtcctcagtgttccactgcctttatccagatt
tactatcacaaagactttgctctgagaaaaatgtgatttctttctttttttttttttttttga
gacagagtctcactctgtcacccaggctggagtgcagtggtgcaatctcggctcactgcaat
ctccgcctcccaggttcacgccattctcttgcctcagtctcccgagtagctgggcctacagg
```

Fig. 8 cont.

Hybrid Rhesus box of RHD negatives cgcccgccaccctgcccagctaatttttgtatttttagtagagacggggtttcaccatgtt
agccaggatggtctcaatctcctgacctcgtgatccacctgcctcagcctcccaaagtgctg
ggattacaggcatgagccaccgcgcccagcagattttttttttttttttttttgagat
ggagtcttgctgtgttgcccagcctggagtgcagtgttatgattttggctcactgcaacctc
tgtctaccatgttcaagcgattctcccacctctgcctcccgtgtagctgggatcacaggcac
acgccaccacacctagctacttttgtatttttagtagaaatggggtttcaccatgttggcc
aggatggtcccgaactcctgacctcaagtgatcctcctgcctcggcctcccaaagtgctggg
attacaggtgtgagccactgtgcctggccaaaaatgtgatttcttatttcccacattgccaa
ttccatttcaattaactataatagctatgtctattgagcactcaagtgtattctagaaactg
ttcctgattctggggatatatccatgaatcaactatagtccctgttattaagtaatctgtag
tctgactaaaccattagaaatttaaaaaatggctactttcaaagacatcttggagttcagga
gtcccacactgcgaaccatattacctaataatccaacctgcttgtaattcacttatttaacc
aatatttattgagtgccaactttgagcctaagatacagcagtaaacaaatggataaagtccc
tgtcctcatgaaacttgtattctaatggaagaaacagaaaacaaacagatataggatgtaat
atcaggtagggataaatactttgaattcaaacaaaagtatacgtagtcagggttcgccaaag
agacacagccaatcggatacatagatatataaaagagggtttatgagttagaaagggctcac
atgattacagaggctgagaagtcccacagcagattgtctgcaagctggagacccagggatac
tggtagcatggctcagtccaagtcccaaagcctcagaatcaggaaagctgatgatataattc
ttagcccaaaggccttagaaccccagcggtgacggaaaggctgatgtaggtcctggagtcct
gagacccaacagcctgggatcctgaaatccaagggcaggaatggaagcgtgtattccagctc
caagagagtaagaccaatttgcctttcttccgtttttgtttcaagccacctgcacattgagg
gcggatggttccctcttagtccattcagtcatatatcaatctcttctggaaataccctcaca
gacacactaacaaataatgcctttccagttctctaggtattctttaatccagtcaagctgac
acctaaaattaaccatcacaaaagttaaggagaaagaagacaacttgtaggggaggctgcta
tgcaagacagtgtgtgaaggaagggctctctgaagaggttaatatctgagcagagacttgaa
tgaagtgaagaagtgagccatgtgggtatggggaatacaacttccaggtagagaagacaagt
gtggtgtgtatcagggtcagcaaagaagccatgtgacagagaagggtgggccagggagagac
ggataagtgatctaactcctgaggaggtggcctggccaggagctagagcatgaagatctcgt
aggactttattctgcaaggtgaaaagccattgtattagtctgttcacaaacccgagactagg
caatttacaaaagaaagagaggtttaatggacttacagttccacatggctggggaggcctca
caatcatggcgaaaggcaatgaggagcaagtcacgtcttacgtggatggcaggcaaagacaa
agacagcttgtgcagagaaactcccccttatagagccatcagatcctgttagacttattcac
tatcacaagaacagcacgggtaagacctgtccccatgattcagttacctcccactgggtccc
tcccacaacgcatgggaattcaggatgagatttgggtggggacacaaccaaaccctatcatt
ccacccatggcccctcccaaatttcatgtcctcacatttcaaaaccaatcacaccatcccaa
cagtccctcaaagtcttaaatgatttcagcattaactcaaaagtccacagtctaatgtctca
tctgagacaaggcaagtcctttccatttatgagcctataaaatccaaagcaagttagttact
tcctagatacaatggggtacaggcattgggtaaatacagccattccaaatgggataaattg
gtcaaaacaaagaggctacaggcccatgagagtccaaaatccagtggggcagtcaaatctta
aagctccaaaatgatctcctttgactccacatctcacatccaggtcacgcagatggaagggg
tgggttcccatggtcttgggcagctctgcccctgtacctttgcagggtacagcctccctctc
agctgctttcatggctggcattgagtgtctgcagcttttccaggtacacggtgcaagctgt
cggtggatctaccattctggggtctggaggacctcttctcacagctccactaggtggtgccc
cagtagggactgtgtgtggggtctctgaccccacatttcccttctgcactgccctggcagag
gatctccatgagggccctgctcctgcagcaaacttctgactgggcatccaggcatttccgca

Fig. 8 cont.

Hybrid Rhesus box of RHD negatives

```
catcctctttaatctaggcgaaggtttccaaaccccaattcttgacttctgtgcactcgcag
tctcaacaccacatggaagctgtcaaggcttggggcttgcactccccgaagctacagcccaa
gctctaccttgcctcccgtcagtcatggttgggagtggctgggatgcagggcaccaagtccc
taggctgcacacagcatgaggaccccgggcctggccaacaaaaccatttttttcctgatacct
ctggacctgtgatgggaggggttgccataaagacctctgacatgccctggagacattttccc
cattgtcttgggaattagcatttggctcctgttactcatgcaaatttctgcagccagcttga
atttctcctcagaaaatgggaatttttcttttctatcacattgtcaggctgcaattttccg
aacttttatgctctgcttcccttataaaactgaatgtctttaacagcacccaagtcacctct
tgaatgctttgctgcttagaaatttctcctgccagatactctaaatcatctctctgaagttc
aaagttctacaaatatctcgtgcaggggcaaaatgccgccagtatctttgctaaaacataac
aagagtcccctttgctccagttcccaacaagttcctcatttccgtctgagaccacctcagcc
tatggactttattgtccacagtgctatcagcattttgggcaaagccattcaacaagtctcta
ggaagttccaaactttcccacatttgcctgtcttcttctgagccctccaaactgttccaaac
cctgcctgttacccagttccaaagtcacatacccattttttgagtatctacggcagcacccca
ctctactggtaccaatttagccactgaagtagttggagaacagaagtaatagactctggttt
acattgtaaaagcttctctgtggctgctgtgtgaagaaaatatatgagaatgaagccccaag
atgaagcagggacacagttgcagtggttagagtaagaaatgctgctggctggcactgaagtg
atagcctggaggtttgtgtgtgcacatgcatgtgtatgtgttttacgatagtaggcccaaca
gatactgtaatccacacttgttttttttttttttgagacagagtctcacctgttgcctag
actagaatgcagtggcacaatcttggctcactacaacctccacctcccaggttcaaacaatc
cttgtgcttcagcctcccgagtagttgggattacaggtgtgtgccaccgtgcccagctatat
tttttgtatttttagcagagatgggatttgccacattggccaggctggtcttgaactcctg
gcctcaagcaatcctcccaccttagcctcccaaagtgctgagccaccacacctggccgcaac
tgatttttaatcatgaaatgacacatacatttaaaaaacccaatacctataatattcctggc
tagtactcttcacatctatatcatcaaaaacaaagaaagtatgtgaaactgacacagccaag
gggagactaaggagacataacaattaactgtaatgtggtattctggaggggatcctggaaca
gaaaaagacattaggcaaaaaactaaagaaatctgaataaaatgtggatgtcagttaataat
aatgtatcatattagtccagtaattgtaacaaatatacccaataatgaaagccattaattat
agggaaaatggaggggttaatatgggtggctggcttttgctatttctagcagctccatttta
tctacaaaagacaaacattcattaagtcccaaaaaggtaaagaatgacaaattaagcatgta
tcttattagtaagagtaatataaagatgctcactcatatttataaatatttgacaatgatgt
taaggccagaaaagagaaaaaagggtaggggcaaaaaacgcaaagagaaaggagttagtatc
ttttctcccgcactcattagctattaaaagaggatgtttgtttaaagctgctcagagctggt
aaactaatgttaagtcactaacgggaatttaaaaggtttcattaagaactgcctgcactaga
ttcctccaccctgagacattaaacaatcacgataaacctcctgagtggtaagaacgtgtcca
tttaaaaacaggctatagattgtcatgcagttttatctactaatcggctaatgcaccgccaa
aaacaaacaaaaaaacccaaagggatgaaagtttcatccatcaaaggaaacaacagtcacct
tggttcccatcccactcatatactgccgccgtacatgtcaatcagatgaacctgtgcgtatc
tcttaacgacaattgacccaccttttttaactgaagtgaagggggggttctgctccgcgaccac
ttcctggatctctcccttcaccctctgtgttctttcgggtgcaccatcgggtcaaagccgca
gcaacgccgtctctgtgtgatcgcatgtgcccttctgcacacgaccttcccccgagagtgac
cagctaccggacaggcaccaaggagggctaccgagcacctcccggaccggcggctgcaggat
cgcgagcgcctccgctagggagaccgcacgttgcgcctgtgcttcctgcggtggcgccttct
gcaaggagacctcgaccctgctccctctccggggctggatctgactccttgacggtgattcc
agacgcgagacccaaactgacggcttctagaagaggggcgagcccggccgcaagtctttcac
```

Fig. 8 cont.

Hybrid Rhesus box of RHD negatives

```
gtagctaagtcatcgttgcttccggcttcttaccgttctcccctttgtaaacggttacctcc
cgaaaacccaggctctcctccaacagtggttctcaagcgaggcgatcttccccgggaggga
tatttggcaaagtctgggggcattttggttcactggggctgctacttgcatccactgggta
gaggcgggggatgcagctacacaacctgcgaagcacgggacagcaccctccccaacccagac
agaattagccggcccaaaacctcagtagtgcccaggctgagaaaccctgccttaaacaaaca
acaaagaaaggccaagtcccataagtgggtcaccgcgccgagactggggtccacgggacacc
ccagccacgccaagccgggaagtccccgcctcctggagctgaacccgcccctctcccagagg
tggagctgcgggggcgggaacaggcacggagaaaataaacaagactaaaaagtcctgagta
gcgctgtgtggccgcaaacctgaacccaccttttgcaccacgcgggacccggcactcttcct
gccacccacccctgagagggctgcgcggccgaccccagtactagaaaacactcgtcacctca
ctcaagacgggtacgaaggccaacggacgccttcctttagaacgctcagcacacagagcaac
ttctcacgcctactctcaaatggcgtactccaaactagcactcccgacgtccagctgtgaac
ccagagcggcggaaagcccctgaacccagcgcccgggcatgcgcagacgcgttgttgtggtg
ggcgtggctccctccggacccggcgccccgccctccgccccgtgtccgcatgcgcgactgag
ccgggtggatggtactgctgcatccgggtgtctg
(end of Rhesus box)
gaggctgtggccgttttgttttcttggctaaaatcgggggagtgaggcgggccggcgcggc
3'
```

Fig. 9

Upstream Rhesus box of D-positives

```
5' ctagaaaacactttgtcattttagaggtgtta
(start of Rhesus box)
tccaatgttcgcgcaggcactggagtcagagaaaatggagttgaatcctttctctgccactc
tttgaggagaatctcaccatttattatgcactgtagaatacaacaataaaatacagccatgt
accacataacaacatcttggtaaacaacagactgcatatatgatggtggtcatccagtaagc
taaggttaatttattattattcccttttttttttcttttttttgagatgtagtcttactctg
tcacccaggctagagtgcaatggcaccatcttggctcactgcaacctctgcctcctgggttc
aagcgaatctcctgcctcagcctccgaagtagctgggaattacaggcacccaccacatctgg
ctaatttttgtatttttagtaaagatggggtttcaccatgttggccaggctgatctcaaac
tcctgacctcaagtgatctgcctgcctcggcctcccaaagtgctgggaccataggcctgagc
cactgtgcccggccttgtttgctttttaacagttaacagtgtgctcatagaaactgctttg
acatgactgcaatcatgtgcttcatagaaacttaattagattataccactagagtcttcaga
tttttatacttttttttttgaaacggagtctcactctgtcaccaggctggagtgcagtgccg
caatctcagctcgccgcaacctccgcctcccaggttcaagtgattctcctgcctcagcctcc
cgagtagctgggattacaagtgcacactaccacgcccagctaattttgcattttttactaga
cagggtttcaccatgttggctaggatagtttcaccaggatctcttggcctcatgatcagcct
gcctcggcctcccaaagtgctgggattacaggtgtgagccaccgtgcccagcctatacttcc
ctttttgaataccatttggcgttttgaagaattaacagctttgtgaacgtggcagtgcttgt
gattcaggcttccactgagaccaaggggagaacctggttgcaggacaaacagacggacagcg
tgtggcagtgtttaaatgctcttctgaaggctgatacgacagctctctgtgcactgattgca
tacgcatcccaagattatattattgttttctattgctatgtgtcacactttgccaaacagga
tgtggaaaatgaataagcggttttcttaggcacttcttaacagacaattggtcaaaatgaac
tccattgcttaagaaacacataaacaccatttagtcactgaatatagctatatgtatggttg
ctactatggggaatcttgttttgccaatttctttgaaaattctggcagaccaaggttcttt
ttgtttacacaatacttgaaaaataaaaatgaacaagccaacaaactaccaagttttcactt
acataaatgtagttacatacagaaaatgtgactgtgaatttttctaggacttttaaactat
aagcactatttgcacgaaagagaaccaatctatcaattacaaactcacataattttacagat
ttttttttccctacacagcacataaaacagaaggaatttgaagccaccctccaaacacaggg
gaaggaggctgtgtgtatatcctcattgtctttcacattctaaggtggttccactcagtgac
tgaaatccttaagtgttgtattagtcggcttgggctaccataacagcagcttaaactgttgt
taagccactcagacttaaacaacagaaatttatttccttatagttctggaggctggaagttc
aaggtgccggcaaggctggtttctggtgagacctctctccctgtcttgcagatggctgcctc
ctccctgtgtcctcatagagcctgtcctctgcttttacacttctggtgtcatcttcctttttt
tttttttttttgagacagagtctcgctctatcgcccaggctggagtgcagtggcccgatcga
tctcggctcactgcaacctctgcctcccaggttcaagcaattctcctgcctcagcctcccga
gtagctgggactacaggtgcccgccatcatgtctggctaattttgtattttagtagagac
agggtttcaccatattggccaggctggtctccaactcctgaccttgtcatctgcctgcctcg
gcctcccaaagtgctaggattacaggcgtgagccaccgcacccggcctctttctcttcttat
aaggacaccagtcctattagattagggctccaccctcatgacctcatttgaccttaactatt
atttctttaaagcacctatttccaaatatagtcactttaggggttagggcttcaaaatatga
atctgagggagatcaattcagtaaatagcagtagtcattaacggacaatatatacaaagata
atttcgtgattactgtccttatgcataaatgtcctcagtgttccactgcctttatccagatt
tactatcacaaagactttgctctgagaaaaatgtgatttctttcttttttttttttttttga
gacagagtctcactctgtcacccaggctggagtgcagtggtgcaatctcggctcactgcaat
ctccgcctcccaggttcacgccattctcttgcctcagtctcccgagtagctgggcctacagg
```

Fig. 9 cont.

Upstream Rhesus box of D-positives cgcccgccaccctgcccagctaatttttgtatttttagtagagacggggtttcaccatgtt
agccaggatggtctcaatctcctgacctcgtgatccacctgcctcagcctcccaaagtgctg
ggattacaggcatgagccaccgcgcccagcagatttttttttttttttttttttgagat
ggagtcttgctgtgttgcccagcctggagtgcagtgttatgattttggctcactgcaacctc
tgtctaccatgttcaagcgattctcccacctctgcctcccgtgtagctgggatcacaggcac
acgccaccacacctagctacttttgtatttttagtagaaatggggtttcaccatgttggcc
aggatggtcccgaactcctgacctcaagtgatcctcctgcctcggcctcccaaagtgctggg
attacaggtgtgagccactgtgcctggccaaaaatgtgatttcttatttcccacattgccaa
ttccatttcaattaactataatagctatgtctattgagcactcaagtgtattctagaaactg
ttcctgattctggggatatatccatgaatcaactatagtccctgttattaagtaatctgtag
tctgactaaaccattagaaatttaaaaaatggctactttcaaagacatcttggagttcagga
gtcccacactgcgaaccatattacctaataatccaacctgcttgtaattcacttatttaacc
aatatttattgagtgccaactttgagcctaagatacagcagtaaacaaatggataaagtccc
tgtcctcatgaaacttgtattctaatggaagaaacagaaaacaaacagatataggatgtaat
atcaggtagggataaatactttgaattcaaacaaaagtatacgtagtcagggttcgccaaag
agacacagccaatcggatacatagatatataaaagagggtttatgagttagaaagggctcac
atgattacagaggctgagaagtcccacagcagattgtctgcaagctggagacccagggatac
tggtagcatggctcagtccaagtcccaaagcctcagaatcaggaaagctgatgatataattc
ttagcccaaaggccttagaaccccagcggtgacggaaaggctgatgtaggtcctggagtcct
gagacccaacagcctgggatcctgaaatccaagggcaggaatggaagcgtgtattccagctc
caagagagtaagaccaatttgcctttcttccgtttttgtttcaagccacctgcacattgagg
gcggatggttccctcttagtccattcagtcatatatcaatctcttctggaaataccctcaca
gacacactaacaaataatgcctttccagttctctaggtattctttaatccagtcaagctgac
acctaaaattaaccatcacaaaagttaaggagaaagaagacaacttgtaggggaggctgcta
tgcaagacagtgtgtgaaggaagggctctctgaagaggttaatatctgagcagagacttgaa
tgaagtgaagaagtgagccatgtgggtatggggaatacaacttccaggtagagaagacaagt
gtggtgtgtatcagggtcagcaaagaagccatgtgacagagaagggtgggccagggagagac
ggataagtgatctaactcctgaggaggtggcctggccaggagctagagcatgaagatctcgt
aggactttattctgcaaggtgaaaagccattgtattagtctgttcacaaacccgagactagg
caatttacaaaagaaagagaggtttaatggacttacagttccacatggctggggaggcctca
caatcatggcgaaaggcaatgaggagcaagtcacgtcttacgtggatggcaggcaaagacaa
agacagcttgtgcagagaaactccccttatagagccatcagatcctgttagacttattcac
tatcacaagaacagcacgggtaagacctgtccccatgattcagttacctcccactgggtccc
tcccacaacgcatgggaattcaggatgagatttgggtggggacacaaccaaaccctatcatt
ccacccatggcccctcccaaatttcatgtcctcacatttcaaaaccaatcacaccatcccaa
cagtccctcaaagtcttaaatgatttcagcattaactcaaaagtccacagtctaatgtctca
tctgagacaaggcaagtcctttccatttatgagcctataaaatccaaagcaagttagttact
tcctagatacaatgggggtacaggcattgggtaaatacagccattccaaatgggataaattg
gtcaaaacaaagaggctacaggcccatgagagtccaaaatccagtggggcagtcaaatctta
aagctccaaaatgatctcctttgactccacatctcacatccaggtcacgcagatggaagggg
tgggttcccatggtcttgggcagctctgcccctgtacctttgcagggtacagcctccctctc
agctgctttcatgggctggcattgagtgtctgcagcttttccaggtacacggtgcaagctgt
cggtggatctaccattctggggtctggaggacctcttctcacagctccactaggtggtgccc
cagtagggactgtgtgtggggtctctgaccccacatttcccttctgcactgccctggcagag
gatctccatgagggccctgctcctgcagcaaacttctgactgggcatccaggcatttccgca

Fig. 9 cont.

Upstream Rhesus box of D-positives catcctctttaatctaggcgaaggtttccaaaccccaattcttgacttctgtgcactcgcag
tctcaacaccacatggaagctgtcaaggcttggggcttgcactccccgaagctacagcccaa
gctctaccttgcctcccgtcagtcatggttgggagtggctgggatgcagggcaccaagtccc
taggctgcacacagcatgaggaccccgggcctggccaacaaaaccatttttcctgatacct
ctggacctgtgatgggaggggttgccataaagacctctgacatgccctggagacattttccc
cattgtcttgggaattagcatttggctcctgttactcatgcaaatttctgcagccagcttga
atttctcctcagaaaatgggaatttttcttttctatcacattgtcaggctgcaaattttccg
aacttttatgctctgcttcccttataaaactgaatgtctttaacagcacccaagtcacctct
tgaatgctttgctgcttagaaatttctcctgccagatactctaaatcatctctctgaagttc
aaagttctacaaatatctcgtgcaggggcaaaatgccgccagtatctttgctaaaacataac
aagagtcccctttgctccagttcccaacaagttcctcatttccgtctgagaccacctcagcc
tatggactttattgtccacagtgctatcagcatttgggcaaagccattcaacaagtctcta
ggaagttccaaactttcccacatttgcctgtcttcttctgagccctccaaactgttccaaac
cctgcctgttacccagttccaaagtcacatacccatttttgagtatctacggcagcacccca
ctctactggtaccaatttagccactgaagtagttggagaacagaagtaatagactctggttt
acattgtaaaagcttctctgtggctgctgtgtgaagaaaatatatgagaatgaagccccaag
atgaagcagggacacagttgcagtggttagagtaagaaatgctgctggctggcactgaagtg
atagcctggaggtttgtgtgtgcacatgcatgtgtatgtgttttacgatagtaggcccaaca
gatactgtaatccacacttgtttttttttttgagacagagtctcacctgttgcctagacta
gaatgcagtggcacaatcttggctcactacaacctccacctcccaggttcaaacaatccttg
tgcttcagcctcccgagtagttgggattacaggtgtgtgccaccgtgcccagctatattttt
tgtatttttagcagagatgggatttgccacattggccaggctggtcttgaactcctggcct
caagcaatcctcccaccttagcctcccaaagtgctgagccaccacacctggccgcaactgat
ttttaatcatgaaatgacacatacatttaaaaaacccaatacctataatattcctggctagt
actcttcacatctatatcatcaaaaacaaagaaagtatgtgaaactgacacagccaagggga
gactaaggagacataacaattaactgtaatgtggtattctggaggggatcctggaacagaaa
aagacattaggcaaaaaactaaagaatctgaataaaatgtggatgtcagttaataataatg
tatcatattagtccagtaattgtaacaaatataccacaataatgaaagccattaattatagg
gaaaatggaggggttaatatgggtggctggcttttgctatttctagcagctccattttatct
gcaaaagacaaacattcattaagtcccaaaaaggtaaagaatgacaaattaagcatgtatct
tattagtaagagtaatataaagatgctcactcctatttataaatatttgacaatcatgttaa
ggccacaaaagagaaaaaagggtaggggcaaaaaacgcaaagagaaaggagttagtatcttt
tctcccgcactcattagctattaaaagaggatgtttgtttaaagctgctcagagctggtaaa
ctaatgttaagtcactaacgggaatttaaaaggtttcattaagaactgcctgcactagattc
ctccaccctgagacattaaacaatcacgataaacctcctgagtggtaagaacttgtccattt
aaaaacaggctatagattgtatcatgcagttttatctactaatcggctaatatcccgccaaa
aacaaaaaaccccaaagggatgaaagtttcatccatcaaaggaaacaacagtcaccttggtt
cccatctcactcatatactgccgccgtacatgtcaatcagatgaacctgtgcgtatctctta
atgacaattgacccacatttttgactgaagtgaaagggggttctgctccgcgaccacttcct
ggatctccccctccaccctctgtgttctttcgggtgcaccatcgggtcaaagccgcagcaac
gccgtctctgtgtgatcgcatgtgcccttctgcacacgaccttcccccgagagtgaccagct
accggacaggcaccaaggagggctaccgagcacctcccggaccggcggctgcaggatcgcga
gcgcctccgctagggagactgcacgttgcgcctgtgcttcctgcggtggcgccttctgcaag
gagacctcgaccctgctccctctccggggctggatctgactccttgacggtgattccagacg
cgagacccaaactgacggcttctagaagaggggcgagcccggccgcaagtctttcacgtagc

Fig. 9 cont.

Upstream Rhesus box of D-positives

```
taagtcatcgttgcttccggcttcttaccgttctcccctttgtaaacggttacctcccgaaa
acccaggctctcctccaacagtggttctcaagcgaggcgatcttccccgggaggggatattt
ggcaaagtctgggggcatttttggttcactggggctgctacttgcatccactgggtagaggc
ggggatgcagctacacaacctgcgaagcacgggacagcaccctccccaacccagacagaat
tagccggcccaaaacctcagtagtgcccaggctgagaaaccctgccttaaacaaacaacaaa
gaaaagccaagtcccataagtgggtcaccgcgccgagactggggtccacgggacaccccagc
cacgccaagccgggaagtccccgcctcctggagctgaacccgcccctctcccagaggtggag
ctgcgggggcgggaacaggcacggagaaaataaacaagactaaaaagtcctgagtagcgct
gtgtggccgcaaacctgaacccacctttgcaccacgcgggacccggcacgcttcctgccac
ccacccctgagagggctgcgcggccgaccccagtactagaaaacactcgtcacctcaatcaa
gacgggtacgaaggccaacggacgccttcctttagaacgctcagcacacagagcaacttctc
acgcctactctcaaatggcgtactccaaactagcactcccgacgtccagctgtgaacccaga
gcggcggaaagcccctgaacccagcgcccgggcatgcgcagacgcgttgttgtggtgggcgt
ggctccctccggacccggcgccccgccctccgccccgtgtccgcatgcgcgactgagccgcg
gggtggtactgctgcatccgggtgtctg
(end of Rhesus box)
aagatccgatgaaataacatatgcaaaatgattgggtccgtgattggcattccagaaatgg
3'
```

Figure 10

Downstream Rhesus box of D-positives aaacgctcat gacagcaaag tc
(Start of Rhesus box)
tccaatgt tcgcgcaggc actggagtca gagaaaatgg
agttgaatcc tttctctgcc actctttgag gagaatctca ccatttatta tgcactgtag
aatacaacaa taaaatacag ccatgtacca cataacaaca tcttggtaaa caacagactg
catatatgat ggtggtcatc cagtaagcta aggttaattt attattattc cttgtttttt
tttttttttt ttttttttg agatgtagtc ttactctgtc acccaggcta gagtgcaatg
gcaccatctt ggctcactgc aacctctacc tcctgggttc aagcaaatct cctgcctcag
cctccaaagt agctgggatt acaggcaccc accacatctg gctaattttt tgtattttta
gtaaagatgg ggtttcacca tgttggccag gctgatctca aactcctgac ctcaagtgat
ctgcccgcct cggcctccca aagtgctgga accacaggcc tgagccactg tgcccagcct
tggttgcttt tttaacagat aacagtgtgc tcatagaaac tgctttgaca tgactgcaat
catgtgcttc atagaaactt aattagatta taccactaga gtcttcagat ttttatactt
ttttttttg aaacggagtc tcactctgtc accaggctgg agtgcagtgc cgcaatctcg
gctcactgca acctccgcct cccaggttca agcaattctc ctgcctcagc ctcccgagta
gctgggatta caagtgcgca ctaccacacc cagctaattt ttgcattttt acttgacagg
gtttcaccat gttggctagg atagtttcac caggatctct tggcctcatg atcagcctgc
ctcggcctcc caaagtgctg ggattacagg tgtgagccac cgtgcccagc ctatacttcc
ctttttgaat accatttggc gttttgaaga attaacagct ttgtgaacgt ggcagtgctt
gtgattcagg cttccattga gaccaagggg agaacctggt tgcaggacaa acagacggac
agcgtgtggc agtgtttaaa tgctcttctg aaggctgata cgacagctct ctgtgcactg
attgcatacg catcccaaga ttatattatt gttttctact gctatgtgtc acactttgcc
aaacaggatg tggaaaatga ataagcggtt ttcttaggca cttcttaaca gacaattggt
caaaatgaac tccattgctt aagaaacaca taaacaccat ttagtcactg aacatagcta
tatgtatggt tgttactatg ggaaatcttg ttttgccaat tttctttgaa aattctggca
gaccaaggtt ctttttgttt acataatact tgaaaaataa aaatgaacaa gctaacaaac
taccaagttt tcacttacat aaatgtagtt gcatacagaa aatgtgactg tgaattaatt
tttctaggac ttttaaacta taagcactat ttgcacaaaa gagaaccaat ctatcaatta
caaactcaca taattttaca gatttttttt ttcctacaca gcacataaaa cagaaggaat
ttgaagccac cctccaaaca caggggaagg aggctgtgtg tatatcctca ttgtctttca
cattctaagg tggttccact cagtgactga aatccttaag cgttgtatta gtctgcttgg
gctaccataa cagcagctta aactgttgtt tagccactca gacttaaaca acagaaattt
atttccttat agttctggag gctggaagtt caaggtgccg gcaaggttgg tttctggtga
gacctctctc cctgtcttgc agatggctgc ctcctccctg tgtcctcata gagcctgtct
tctgctttta cacttctggt gtcatcttcc tttttttttt tttttttttt ttttgagaca
gagtctcgct ctatcgccca ggctggagtg cagtggcccg atcgatctcg gctcactgca
acctctgcct cccaggttca agcaattctc ctgcctcagc ctcccaagta gctgggacta
caggtgcccg ccatcatgcc tggctaattt ttgtattttt agtagagaca gggtttcacc
atattggcca ggctggtctc gaactcctga ccttgtcatc tgcctgcctc ggcctcccaa
agtgctagga ttacaggcgt gagccaccgc acccggcctc ttcctcttct tataaggaca
ccagtcctat tagattaggg ctccaccctc ataacctcat ttgaccttaa ctattatttc
tttaaagcac ctatttccaa atatagtcac tttaggggtt agggcttcaa aagatgaatc
tgagggagct caattcagta aatagcagta gtcattaatg gacaatgtat acaaagataa
tttcgtgatt actgtcctta tgcataaacg tcctcagtgt tccactgcgt ttatccagat
ttagtatcac aaagactttg ctctgagaaa aatgtgattt tttttttttt ttttttttg
agacggagtc tcgctctgtt acccaggctg gagtgcagtg gcgcgatctc ggctcactgc
aagctccgcc tcccgggttc acgccattct cctgcctcag cctccggagt agctgggact
acaggcgccc gccactacgc ccggctaact tttttgtatt tttagtagag acggggtttc
accatgttag ccaggatggt ctcaatctcc tgacctcgtg atccacctgc ctcagcctcc
caaagtgctg ggattacagg catgagccac cgcgcccagc agattttttt tttttttttt
gagatggagt cttgctctgt tgcccaacct ggagtgcagt gttatgattt tggctcactg
caacctctac catgttcaag cgattctccc acctctgcct cccgtgtagc tgggatcaca
ggcacacgcc accacaccta gctacttttt gtatttttag tagaaatggg gtttcaccat
gttggccagg atggtcccga actcctgacc tcaagtgatc ctcctgcctc ggcctccaaa

Figure 10 cont.

Downstream Rhesus box of D-positives gtgctgggat tacaggtgtg agccactgtg cctggccaaa aatgtgattt cttatttccc
acattgccaa ttccatttca attaactata atagctatgt ctattgagca ctcaagcgta
ttctagaaac tgttcctgat tctggggata tatccatgaa tcaactatag tccctgttat
taagtaatcc gtagtctgac taaaccatta gaaattaaaa aaaaatggct actttcaaag
acatcttgga gttcaggagt cccacactgc gaaccatatt acctaataat ccaacctgct
tgtaattcac ttatttaacc aatatttatt gagtgccaac tttgagccta agatacagca
gtaaacaaat gcataaagtc cctgtcccca tgaaacttgt attctaatgg aaaaaacaga
aaacaaacag atataggatg taatatcagg tagggataaa tactttgaat tcaaacaaaa
gtatacgtag tcagggttcc ccagagagac acagccaatc gatacataga tatataagag
agggtttatg agttagaaag ggctcacatg attacagagg ctgagaagtc ccacaacaga
ttgtctgcaa gctggagacc cagggatact ggtagcatgg ctcagtccaa gtcccaaagt
ctcagaatca ggaaagctga tgatataatt cttagcccaa aggccttaga accccagcgg
tgacggaaag gctgatgtag gtcctggcgt cctgagaccc aacagcctgg gatcctgaaa
tccaagggca ggaatggaag cgtgtattcc agctccaaga gagtaagacc aatttgcctt
tcttccgttt ttgttccaag ccaactgcac gttgagggcg gatggttccc tcttagccca
ttcagtcata tatcaatctc ttctggaaat accctcacag acacactaac aaataatgcc
tttccagttc tctaggtatt ctttaatcca gtcaagctga cacctaaaat taaccatcac
aaaagttaag gagaaagaag acaacttgta ggagaggctg ctatgcaaga cagtgtgtga
aggaagggct ctctgaagag gttaatatct gagcagagac ttgaatgaag tgaagaagtg
agccatgtgg gtatggggaa tacaacttcc aggtagagaa gacaagtgtg gtgtgtatca
cggtcagcaa agaagccatg tgacagagaa gggtgggcca gggagagacg gataagtgat
ctaactcctg aggaggtggc ctggccagga gctagagcat gaggatctcg taggatttta
ttctgcaagg tgaaaagcca ttgtattagt ctgttcacaa accccagact aggcaattta
caaaagaaag agaggtttaa tggacttaca gttccacatg gctggggagg cctcacaatc
atggcgaaag gcaatgagga gcaagtcacg tcttacgtgg atggcaggca aagacaaaga
cagcttgtgc agagaaactc cccctatag agccatcaga tcctgttaga cttatcacta
tcacgagaac agcacgggta agacctgtcc ccatgattca gttacctccc actgggtccc
tcccacaacg catgggaatt caggatgaga tttgggtggg gacacaacca aaccctatca
ttccacccat ggcccctccc aaatttcatg tcctcacatt tcaaaaccaa tcacaccatc
ccaacagtcc ctcaaagtct taaatgattt cagcattaac tcaaaagtcc acagtctaat
gtctcatctg agacaaggca agtcctttcc gtctatgagc ctataaaatc caaagcaagt
taattacttc ctagatacaa tgggggtaca ggcattgggt aaatacagcc attccaaatg
ggataaattg gtcaaaacaa agaggctaca ggcccatgag agtccaaaat ccagtggggc
agtcaaatct taaagctcca aaatgatctc ctcttgactc cacatctcac atccaggtca
tgcagatgga aggggtgggt tcccatggtc ttgggcagct ctgcccctgt acctttgcag
ggtacagcct ccctctcagc tgctttcatg ggctggcatt gagtgtctgc aacttttcca
ggtacacggt gcaagctgtc ggtggatcta ccattctggg gtctggagga cctcttctca
cagctccact aggtggtgcc ccagtaggga ctgtgtgtgg ggtctctgac ccccacatttc
ccttctgcac tgccctggca gaggatctcc atgagggccc tgcccctgca gcaaacttct
gcctgggcat ccaggcattt ccgcacatcc tctttaatct aggcgaaggt ttccaaaccc
cagttcttga cttctgtgca ctcgcagtct caacaccaca tggaagctgt caaggcttgg
ggcttgcact ccccgaagct acagcccaag ctctaccttg cctcctgtca gtcatggttg
ggagtggctg ggatgcaggg caccaagtcc ctaggctgca cacagcatga ggaccccggg
cctggccaac aaaaccattt tttcctgata tctctggacc tgtgatggga ggggttgcca
taaagacctc tgacatgccc tggagacatt ttccccattg tcttgggaat tagcatttgg
ctcctgttac tcatgcaaat ttctgcagcc agcttgaatt tctcctcaga aaatgggaat
ttttcttttc tatcacattg tcaggctgca aattttccga acttttatgc tctgcttccc
ttataaaact gaatgtcttt aacagcaccc aagtcacctc ttgaatgctt tgctgcttag
aaatttctcc tgccagatac tctaaatcat ctctctgaag ttcaaagttc tacaaatatc
tcgtgcaggg gcaaaatgcc gccagtatct ttgctaaaac ataacaagag tccccttttgc
tccagttccc aacaagttcc tcatttccgt ctgagaccac ctcagcctat ggactttatt
gtccacagtg ctatcagcat tttgggcaaa gccattcaac aagtctctag gaagttccaa
actttcccac atttgcctgt cttcttctga gccctccaaa ctgttccaaa ccctgcctgt
tacccagttc caaagtcaca tacccatttt tgagtatcta cggcagcacc ccactctact
ggtaccaatt tagccactga agtagttgga gaacagaagt aatagactct ggtttacatt

Figure 10 cont.

Downstream Rhesus box of D-positives gtaaaagctt ctctgtggct gctgtgtgaa gaaaatatat gagaatgaag ccccaagatg
aagcagggac acagttgcag tggttagagt aagaaatgct gctggctggc actgaagtga
tagcctggag gtttgtgtgt gcacatgcat gtgtatgtgt tttacgatag taggcccaac
agatactgta atccacactt gttttttttt ttttttgag acagagtctc acctgttgcc
tagactagaa tgcagtggca caatcttggc tcactacaac ctccacctcc caggttcaaa
caatccttgt gcttcagcct cccgagtagt tgggattaca ggtgtgtgcc accgtgccca
gctatatttt ttgtattttt agcagagatg ggattttgcc acattggcca ggctggtctt
gaactcctgg cctcaagcaa tcctcccacc ttagcctccc aaagtgctga gccaccacac
ctggccgcaa ctgattttta atcatgaaat gacacataca tttaaaaaac ccaataccta
taatattcct ggctagtact cttcacatct atatcatcaa aaacaaagaa agtatgtgaa
actgacacag ccaaggggag actaaggaga cataacaatt aactgtaatg tggtattctg
gaggggatcc tggaacagaa aaagacatta ggcaaaaaac taaagaaatc tgaataaaat
gtggatgtca gttaataata atgtatcata ttagtccagt aattgtaaca aatataccca
ataatgaaag ccattaatta tagggaaaat ggaggggtta atatgggtgg ctggcttttg
ctatttctag cagctccatt ttatctacaa aagacaaaca ttcattaagt cccaaaaagg
taaagaatga caaattaagc atgtatctta ttagtaagag taatataaag atgctcactc
atatttataa atatttgaca atgatgttaa ggccagaaaa gagaaaaaag ggtaggggca
aaaaacgcaa agagaaagga gttagtatct tttctcccgc actcattagc tattaaaaga
ggatgtttgt ttaaagctgc tcagagctgg taaactaatg ttaagtcact aacgggaatt
taaaaggttt cattaagaac tgcctgcact agattcctcc accctgagac attaaacaat
cacgataaac ctcctgagtg gtaagaacgt gtccatttaa aaacaggcta tagattgtca
tgcagtttta tctactaatc ggctaatgca ccgccaaaaa caaacaaaaa aacccaaagg
gatgaaagtt tcatccatca aaggaaacaa cagtcacctt ggttcccatc ccactcatat
actgccgccg tacatgtcaa tcagatgaac ctgtgcgtat ctcttaatga caattgaccc
accttttaa ctgaagtgaa ggggggttct gctccgcgac cacttcctgg atctctccct

Figure 10 cont.

Downstream Rhesus box of D-positives

```
tcaccctctg tgttctttcg ggtgcaccat cgggtcaaag ccgcagcaac gccgtctctg
tgtgatcgca tgtgcccttc tgcacacgac cttcccccga gagtgaccag ctaccggaca
ggcaccaagg agggctaccg agcacctccc ggaccggcgg ctgcaggatc gcgagcgcct
ccgctaggga gaccgcacgt tgcgcctgtg cttcctgcgg tggcgccttc tgcaaggaga
cctcgaccct gctccctctc cggggctgga tctgactcct tgacggtgat tccagacgcg
agacccaaac tgacggcttc tagaagaggg gcgagcccgg ccgcaagtct ttcacgtagc
taagtcatcg ttgcttccgg cttcttaccg ttctcccctt tgtaaacggt tacctcccga
aaacccaggc tctcctccaa cagtggttct caagcgaggc gatcttcccc gggaggggat
atttggcaaa gtctgggggc atttttggtt cactggggct gctacttgca tccactgggt
agaggcgggg gatgcagcta cacaacctgc gaagcacggg acagcaccct ccccaaccca
gacagaatta gccggcccaa aacctcagta gtgcccaggc tgagaaaccc tgccttaaac
aaacaacaaa gaaaggccaa gtcccataag tgggtcaccg cgccgagact ggggtccacg
ggacacccca gccacgccaa gccgggaagt ccccgcctcc tggagctgaa cccgcccctc
tcccagaggt ggagctgcgg ggggcgggaa caggcacgga gaaaataaac aagactaaaa
agtcctgagt agcgctgtgt ggccgcaaac ctgaacccac cttttgcacc acgcgggacc
cggcactctt cctgccaccc acccctgaga gggctgcgcg gccgacccca gtactagaaa
acactcgtca cctcactcaa gacgggtacg aaggccaacg gacgccttcc tttagaacgc
tcagcacaca gagcaacttc tcacgcctac tctcaaatgg cgtactccaa actagcactc
ccgacgtcca gctgtgaacc cagagcggcg gaaagcccct gaacccagcg cccgggcatg
cgcagacgcg ttgttgtggt gggcgtggct ccctccggac ccggcgcccc gccctccgcc
ccgtgtccgc atgcgcgact gagccgggtg gatggtactg ctgcatccgg gtgtctg
(end of Rhesus box)
gag gctgtggccg ttttgttttc ttggctaaaa tcgggggagt gaggcgggcc ggcgcggc  3'
```

Fig. 11

```
ctgatctaca taggaattgt tttcaagaca tttctgcatt cctctagtga cagggtgctc      60
actacctcat gagtatttca gtggacaact gtaatggtca ataaagtatc cactttccac     120
ctccctgcag ctcctggccc tggctttatt ctctggggct ccacacattc agtttacact     180
cagtggccag tggctgggac cattgtagaa aataaggaaa ctccaattcc ttccttcttt     240
tcttcctctt tcatctcttc ctccctctct acatccctct ctctcttcct tccttcctcg     300
acacttacca tgtaccagac cttctgccag gcacatggat gggagcacag gggaagttgg     360
ctgcagggtt agaactaagt cccaagcccc ctaaagctca tgccagggga ctggactgtc     420
cagtactgag ggatggggat gctgaggctg gtggccttcc tcaaatgcac tgtagtgccc     480
caggcagagt cctgggctgc cctgtgagga ggtgaccaga ggtagagcaa cttcacccta     540
aggctggatc aggatcccct ccaggttttt actagagcca aacccacatc tcctttctct     600
tctgccaccc ccccttaaaa tgcttagaaa cacatagatt taaatacaaa ttcaaatgta     660
agtaatttca actgtgtaac tatgaggagt cagttctacg tgggtcctat ctgtatcctc     720
cccagggctc agctccattc tttgctttca ttcattctca ttcaatacat tgttgttaag     780
agctcactgg gtgccctctc tgtcatgtag taaggtttta aaaagaaagc ctcttctgag     840
cttcagtttc cttattcata aaataggagt attgatccgt tccttgcttt tcttacaagg     900
atatgctgaa gatgactgaa gtacagagta aagaaggatt atgtttgggt gtcaaaggaa     960
tagaatgccc tctttcaaac tgagcacagc aggaacctgt aacaggaaca cagcaacttg    1020
ttgaatgaat gacaatattg gaaaacatac atttcctccc ctccccatca tagtccctct    1080
gcttccgtgt taactccata gagaggccag cacaaccagc cttgcagcct gagataaggc    1140
ctttggcggg tgtctcccct atcgctccct caagccctca agtaggtgtt ggagagaggg    1200
gtgatgcctg gtgctggtgg aacccctgca cagagacgga cacaggatg                1249
```

Fig. 12

```
2938 CTAGAGAGGGAAGTTTTTGAAAATTAAACACTGTCTAATTTTCTGCAAAGTTTTTATTCATGAATTAAGAGTATTTCCCTTAGTCCATTATTCCCAAGGC RHCE
     CTAGAGAGGGAAGTTTTTGAAAATTAAACACTGTCTAATTTTCTGCAAAGTTTTTATTCATGAATTAAGAGTATTTCCCTTTGTCCATTATTCCCAAGGC Cde^s
     CTAGAGAGGGAAGTTTTTGAAAATTAAACACTGTCTAATTTTCTGCAAAGTTTTTATTCATGAATTAAGAGTATTTCCCTTTGTCCATTATTCCCAAGGC RHD

                             |********************** breakpoint region ************************************
3038 AAATATGGAAGTTTGATCATATGCTAATCATAGTAAAGCTGGATTCTCTTTAAGAGATTGAGAAATTAAAAGGCAAAAGCTGATATATCATGTTTAGTTA RHCE
     AAATATGGAAATTTGATCATGTAACTAATCATAGTAAAGCTGGATTCTCTTTAAGAGATTGAGAAATTAAAAGGCAAAAGCTGATATGTCATGTTTAGTTA Cde^s
     AAATATGGAAATTTGATCATGTAACTAATCATAATAAAGCTGGATTCTCTTTAAGAGATTGAGAAATTAAAAGGCAAAAGCTGATATATCATGTTTAGTTA RHD

     ********************************** breakpoint region **********************|
3138 TACTGTGAGTCTTATAAGAAGCTGGGAGGCAACCCCATTAACTCACCAGAATACAGAACTCAGTCTCACAACTTAAATATAATTCCTCTCAAACCTTTTC RHCE
     TATTGTGAGTCTTATAAGAAGCTGGGAGGCAACCCCATTAACTCACCAGAATACAGAACTCAGTCTCACAACTTAAATATAATTCCTCTCAAACCTTTTC Cde^s
     TATTGTGAGTCTTATAAGAAGCTGGGAGGCAACCCCATTAACTCACCAGAATACAGAACTCAGTCTCACAACTTAGATATAATTCCTCTCAAACCTTTTC RHD

3238 CTCAAAG-TTAAATTCTGAAAATAATCTTGTGATTAAGAGAAGAAGGCTGTCCACCAATGGACTTATCTGTTATTTCTTCCTTATTGTGAGCTTAATGGC RHCE
     CTCAAAG-TTAAATTCTGAAAATAATCTTGTGATTAAGAGAAGAAGGCTGTCCACCAATGGACTTATCTGTTATTTCTTCCTTATTGTGAGCTTAATGGC Cde^s
     CTCAAAGATTAAATTCTGAAAATAATCTTGTGATTAAGAGAAGAAGGCTGTCCACCAATGGGCTTATCTGTTATTTCTTCCTTATTGTGAGCTTAATGGC RHD

3337 ATGACAAAGCAGAGGCAAAGAGGCATACATCAATTCTTCAAAGTAGGAAGTCAAAAAGGTCAGAGCTTCCACAGCATGGCAACAGCTTTGCAGATGCCCA RHCE
     ATGACAAAGCAGAGGCAAAGAGGCATACATCAATTCTTCAAAGTAGGAAGTCAAAAAGGTCAGAGCTTCCACAGCATGGCAACAGCTTTGCAGATGCCCA Cde^s
     ATGACAAAGCAGAGGCAAAGAGGCATACATCAATTCTTCAAAGTAGGAAGTCAAAAAGGTCAGAGCTTCCACAGCATGGCAACAGCTTTGCAGATGCCCA RHD

3437 CATCGTGATAGTTGAAATAGCAAAGCCCAGCAAAGGTTAAAGCTGAAAATGCCAAAAGCCCTGCCTTGGCAGCTTTCTGCGAGGCATCCCCATGAACATA RHCE
     CATCGTGATAGTTGAAATAGCAAAGCCCAGCAAAGGTTAAAGCTGAAAATGCCAAAAGCCCTGCCTTGGCAGCTTTCTGCGAGGCATCCCCATGAACATA Cde^s
     CATCGTGATAGTTGAAATAGCAAAGCCCAGCAAAGGTTAAAGCTGAAAATGCCAAAAGCCCTGCCTTGGCAGCTTTCTGCGAGGCATCCCCATGAACATA RHD

3537 GTCAGTAACAACTTGTCCAAGGCCCCAGTGACCATGAAGAGTGAGGGCTGCAGCCAGGGAATAGTCCGTCGCAGAGCAAGGATTCAAATAAGCAGCCGGA RHCE
     GTCAGTAACAACTTGTCCAAGGCCCCAGTGACCATGAAGAGTGAGGGCTGCAGCCAGGGAATAGTCCGTCGCAGAGCAAGGATTCAAATAAGCAGCCGGA Cde^s
     ATCAGTAACAACTTGTTCAAGGCCCCAGTGACCATGAAGAGTGAGGGCTGCAGCC-GGGAATAGTCCGTCGCAGAGCAAGGATTCAAATAAGCAGCCGGA RHD
```

Fig. 13

```
2726 TTGTATCTCTTTTTACAGCTACCTCCCATTTCCCTTCTATTTCAAGCTAGTAACACAGTTTTCTTTTAAATTCATTTATTTAAATGTAAAAATAAGTCTA RHCE
     TTGTATCTCTTTTTACAGCTACCTCCCATTTCCCTTCTATTTCAAGCTAGTAACACAGTTTTCTTTTAAATTCATTTATTTAAATGTAAAAATAAGTCTA Cde^s
     TTGTATCTCTTTTTACAGCTACCTCCCATTTCCCTTCTATTTCAAGCTAGTAACTCAGTTTTCTTTTAAATTCAATTATTTAAATGTAAAAATAAGTCTA RHD

2826 TTTGGAGAAAAAAAATTTTTAATAGCATCTCTGGAATGCCAGTATGGCTAAATTCATGAATGTTGTCCTCAAATGCTGAAATCTGGGAAGCATCTGGCCA RHCE
     TTTGGAGAAAAAAAATTTTTAATAGCATCTCTGGAACGCCAGTATGGCTAAATTCATGAATGTTGTCCTCAAATGCTGAAATCTGGGAAGCATCTGGCCA Cde^s
     TTTGGAGAAAAAAAATTTT-AATAGCATCTCTGGAATGCCAGTATGGCTAAATTCATGAATGTTGTCCTCAAATGCTGAAATCTGGGAAGCATCTGGCCA RHD

                                                     |************** breakpoint region ****************
2926 AGCTTTGTGGACAGGCCTGCCTAGTTTGAATCCCAAGAGCCACTCATTCCGAGCCACAAAACATTGGAATTCTTGGTTCACTTCCCTAACCTGAACTTGT RHCE
     AGCTTTGTGGAGAGGCCTGCCTAGTTTGAATCCCAAGAGCCACTCATTCCGAGCCACAAAACATTGGAATTCTTGGTTCACTTCCCTAACCTGAACTTGC Cde^s
     AGCTTTGTGGACAGGCCTGCCTAGTTTGAATCCCAAGAGCCACCCAGTCCAAGCCACAAAACATTGGAATTCTTGGTTCACTTCCCTAACCTGAACTTGC RHD

     ************************************ breakpoint region ********************************************
3026 CCTCTGTGAAATAGGGACATTAATAGCTCACTCACAGGGCTGCTGTGAGGACATGTGTTGAGCTGAGGGTCTCGCCAGGGGAGACCCTGTGCAGGGAGAC RHCE
     CCTCTGTGAAATAGGGACATTAATAGCTCACTCACAGGGCTGCTGTGAGGACATGTGTTGAGCTGAGGGTCTGGTCAGGGGAGACCCTGTGCAGGGAGAC Cde^s
     CCTCTGTGAAATAGGGACACTAATAGCTCACTCACAGGGCTGCTGTGAGGACATGTGTTGAGCTGAGGGTCTCGCCAGGGGAGACCCTGTGCAGGGAGAC RHD

     ************************************ breakpoint region ********************************************
3126 TGTTATCATGGTGATGGATTTCTGCTTCATTCATTTCTTTTTCCAGACAGCATCATATAGAATGAGTTGTGGGGTGGCAGTCAGCAGGTTTGGGTTTATC RHCE
     TGTTATCATGGTGATGGATTTCTGCTTCATTCATTTCTTTTTCCAGACAGCATCATATAGAATGAGTTGTGGGGTGGCAGTCAGCAGGTTTGGGTTTATC Cde^s
     TGTTATCATGGTGATGGATTTCTGCTTCATTCATTTCTTTTTCCAGACAGCATCATATAGAATGAGTTGTGGGGTGGCAGTCAGCAGGTTTGGGTTTATC RHD

     ************************************ breakpoint region ********************************************
3226 CTCTATTCTGCCACTTATTACTTAAAAAAA------AAAACCCAACTTATATAGTATAAGCTATATCCAGAAAAGTGCAAATATCATACAAGTACCATTT RHCE
     CTCTATTCTGCCACTTATTACTTAAAAAAACCCCAAAAAACCCAACTTATATAGTATAAGCTATATCCAGAAAAGTGCAAATATCATACAAGTACCATTT Cde^s
     CTCTATTCTGCCACTTATTACTTAAAAAAACCCCAAAAAACCCAACTTATATAGTATAAGCTATATCCAGAAAAGTGCAAATATCATACAAGTACCATTT RHD
```

Fig. 13 cont.

```
     ************************************ breakpoint region **************************************************
3320 GATGAATCTTCTGATATCCCCACATAACCAACACCCAGAACCTCTTCTTGTCTCATTCCAGGATAACCACTAACCTGACTTCTAACAGCATCAGTCAGTT RHCE
     GATGAATCTTCTGATATCCCCACATAACCAACACCCAGAACCTCTTCTTGTCTCATTCCAGGATAACCACTAACCTGACTTCTAACAGCATCAGTCAGTT Cde^s
     GATGAATCTTCTGATATCCCCACATAACCAACACCCAGAACCTCTTCTTGTCTCATTCCAGGATAACCACTAACCTGACTTCTAACAGCATCAGTCAGTT RHD

     ************************************ breakpoint region **************************************************
3420 TTGTCTGTTTTTGTACATTATATATGTGATGGTTTGAATGTGTCCCCCAAATTTCATGTGCTAGAAACTTAATCCTTCAATTCATATGTTGATGCTATTT RHCE
     TTGTCTGTTTTTGTACATTATATATGTGATGGTTTGAATGTGTCCCCCAAATTTCATGTGCTGGAAACTTAATCCTTCAATTCATATGTTGATGCTATTT Cde^s
     TTGTCTGTTTTTGTACATTATATATGTGATGGTTTGAATGTGTCCCCCAAATTTCATGTGCTGGAAACTTAATCCTTCAATTCATATGTTGATGGTTTTT RHD

     ************************************ breakpoint region **************************************************
3520 GGAGGAAGGGCCTTTGGGAAGTAATTAGGATTAGATAAGGTCATGGGGTGAGGTATGATGGCACTGGTGACTTATAAGAAGAGAAAGAGAAATCTGAGCT RHCE
     GGAGGAAGGGCCTTTGGGAAGTAATTAGGATTAGATAAGGTCATGGGGTGAGGTATGATGGCACTGGTGACTTATAAGAAGAGAAAGAGAAATCTGAGCT Cde^s
     GGAGGAAGGGCCTTTGGGAAGTAATTAGGATTAGATAAGGTCATGGGGTGAGGTATGATGGCACTGGTGACTTATAAGAAGAGAAAGAGAAATCTGAGCT RHD

     * breakpoint region *|
3620 GGCATGCTCTTGCCCTCTCACCGTGTGATGACTTCTCCATGTCATGATGCAGCAAGAAGGCCCTCACCAGATGGTGGCACCATGCTTTTGGACTTCCCAG RHCE
     GGCATGCTCTTGCCCTCTCACTGTGTGATGACTTCTCCATGTCATGATGCAGCAAGAAGGCCCTCACCAGATGGTGGCACCATGCTTTTGGACTTCCCAG Cde^s
     GGCATGCTCTTGCCCTCTCACTGTGTGATGACTTCTCCATGTCATGATGCAGCAAGAAGGCCCTCACCAGATGGTGGCACCATGCTTTTGGACTTCCCAG RHD
```

A
B
control
Intron 4
Exon 7
control
Intron 7
RHD(W16X)
RHDΨ
1
2
3
4
5
6
7
8
standard RHD
RHD negative
RHD-CE(8-9)-D
RHD(W16X)
RHDΨ
Cde^s
D cat VI type II
D cat IV type III

SEQUENCE LISTING

```
<160> NUMBER OF SEQ ID NOS: 114

<210> SEQ ID NO 1
<211> LENGTH: 100
<212> TYPE: DNA
<213> ORGANISM: Homo sapiens

<400> SEQUENCE: 1

gcatgcgcga ctgagccggg tggatggtac tgctgcatcc gggtgtctgg aggctgtggc     60

cgttttgttt tcttggctaa aatcggggga gtgaggcggg                          100


<210> SEQ ID NO 2
<211> LENGTH: 26
<212> TYPE: DNA
<213> ORGANISM: Homo sapiens

<400> SEQUENCE: 2

actgcacgac ggggctggac tgacgt                                          26


<210> SEQ ID NO 3
<211> LENGTH: 45
<212> TYPE: DNA
<213> ORGANISM: Homo sapiens

<400> SEQUENCE: 3

agctgaaaaa aatgtctgga tttctagagg gcttgagatg ctcag                     45


<210> SEQ ID NO 4
<211> LENGTH: 26
<212> TYPE: DNA
<213> ORGANISM: Homo sapiens

<400> SEQUENCE: 4

gcttccattg ctgctggtgt actagt                                          26


<210> SEQ ID NO 5
<211> LENGTH: 44
<212> TYPE: DNA
<213> ORGANISM: Homo sapiens

<400> SEQUENCE: 5

agttttttac aggctggtgg attatcatag atgcagctgt tatt                      44


<210> SEQ ID NO 6
<211> LENGTH: 26
```

<212> TYPE: DNA
<213> ORGANISM: Homo sapiens

<400> SEQUENCE: 6
tatagcaacc atagccttcc taatgt 26

<210> SEQ ID NO 7
<211> LENGTH: 44
<212> TYPE: DNA
<213> ORGANISM: Homo sapiens

<400> SEQUENCE: 7
aggattaatg cagtatcgaa tggacaagtc cgaggtgata gtta 44

<210> SEQ ID NO 8
<211> LENGTH: 26
<212> TYPE: DNA
<213> ORGANISM: Homo sapiens

<400> SEQUENCE: 8
tgaaggttgt ctgggtcaaa acaggt 26

<210> SEQ ID NO 9
<211> LENGTH: 44
<212> TYPE: DNA
<213> ORGANISM: Homo sapiens

<400> SEQUENCE: 9
aggtgctcgc atttggcttt tcgttggttt catgttggcc tttg 44

<210> SEQ ID NO 10
<211> LENGTH: 26
<212> TYPE: DNA
<213> ORGANISM: Homo sapiens

<400> SEQUENCE: 10
tttttggagg ttatgttgct aaaggt 26

<210> SEQ ID NO 11
<211> LENGTH: 38
<212> TYPE: DNA
<213> ORGANISM: Homo sapiens

<400> SEQUENCE: 11
agaaaaagac atagtatacc ctggaattgc tgtatttt 38

<210> SEQ ID NO 12
<211> LENGTH: 26
<212> TYPE: DNA
<213> ORGANISM: Homo sapiens

<400> SEQUENCE: 12
tccagaatgc cttcatcttt tttggt 26

<210> SEQ ID NO 13
<211> LENGTH: 53
<212> TYPE: DNA
<213> ORGANISM: Homo sapiens

<400> SEQUENCE: 13
aggagggctg gtttttaagt ttggccgcac tgaagactta tggcagtgaa cac 53

<210> SEQ ID NO 14

```
<211> LENGTH: 249
<212> TYPE: DNA
<213> ORGANISM: Homo sapiens

<400> SEQUENCE: 14

agcatcatcc taatgaaact aaacatttat tttaaactta ttaaattgac tcttaaacta     60

agtttttagt ctttaatttt ttaatatcaa atctgtctct gaccttgttt cattatacat    120

aaggagcttt gctgtcatga gcgtttctca cgtacaaatg caggcaacag tgagaggaag    180

ttgtcttgtt tttgaacagg ccttgttttt cttggatgct tttgcttaaa atccaacagc    240

caaatgagg                                                            249


<210> SEQ ID NO 15
<211> LENGTH: 3093
<212> TYPE: DNA
<213> ORGANISM: Homo sapiens

<400> SEQUENCE: 15

attcactatc acaagaacag cacgggtaag acctgtcccc atgattcagt tacctcccac     60

tgggtccctc ccacaacgca tgggaattca ggatgagatt tgggtgggga cacaaccaaa    120

ccctatcatt ccacccatgg cccctcccaa atttcatgtc ctcacatttc aaaaccaatc    180

acaccatccc aacagtccct caaagtctta aatgatttca gcattaactc aaaagtccac    240

agtctaatgt ctcatctgag acaaggcaag tcctttccat ttatgagcct ataaaatcca    300

aagcaagtta gttacttcct agatacaatg gggtacagg cattgggtaa atacagccat     360

tccaaatggg ataaattggt caaaacaaag aggctacagg cccatgagag tccaaaatcc    420

agtggggcag tcaaatctta aagctccaaa atgatctcct ttgactccac atctcacatc    480

caggtcacgc agatggaagg ggtgggttcc catggtcttg ggcagctctg cccctgtacc    540

tttgcagggt acagcctccc tctcagctgc tttcatgggc tggcattgag tgtctgcagc    600

ttttccaggt acacggtgca agctgtcggt ggatctacca ttctggggtc tggaggacct    660

cttctcacag ctccactagg tggtgcccca gtagggactg tgtgtggggt ctctgacccc    720

acatttccct tctgcactgc cctggcagag gatctccatg agggccctgc tcctgcagca    780

aacttctgac tgggcatcca ggcatttccg cacatcctct ttaatctagg cgaaggtttc    840

caaaccccaa ttcttgactt ctgtgcactc gcagtctcaa caccacatgg aagctgtcaa    900

ggcttggggc ttgcactccc cgaagctaca gcccaagctc taccttgcct cccgtcagtc    960

atggttggga gtggctggga tgcagggcac caagtcccta ggctgcacac agcatgagga   1020

ccccgggcct ggccaacaaa accatttttt cctgatacct ctggacctgt gatgggaggg   1080

gttgccataa agacctctga catgccctgg agacattttc cccattgtct tgggaattag   1140

catttggctc ctgttactca tgcaaatttc tgcagccagc ttgaatttct cctcagaaaa   1200

tgggaatttt tcttttctat cacattgtca ggctgcaaat tttccgaact tttatgctct   1260

gcttccctta taaaactgaa tgtctttaac agcacccaag tcacctcttg aatgctttgc   1320

tgcttagaaa tttctcctgc cagatactct aaatcatctc tctgaagttc aaagttctac   1380

aaatatctcg tgcaggggca aaatgccgcc agtatctttg ctaaaacata acaagagtcc   1440

cctttgctcc agttcccaac aagttcctca tttccgtctg agaccacctc agcctatgga   1500

ctttattgtc cacagtgcta tcagcatttt gggcaaagcc attcaacaag tctctaggaa   1560

gttccaaact ttcccacatt tgcctgtctt cttctgagcc ctccaaactg ttccaaaccc   1620

tgcctgttac ccagttccaa agtcacatac ccatttttga gtatctacgg cagcacccca   1680
```

```
ctctactggt accaatttag ccactgaagt agttggagaa cagaagtaat agactctggt   1740
ttacattgta aaagcttctc tgtggctgct gtgtgaagaa aatatatgag aatgaagccc   1800
caagatgaag cagggacaca gttgcagtgg ttagagtaag aaatgctgct ggctggcact   1860
gaagtgatag cctggaggtt tgtgtgtgca catgcatgtg tatgtgtttt acgatagtag   1920
gcccaacaga tactgtaatc cacacttgtt ttttttttt gagacagagt ctcacctgtt   1980
gcctagacta gaatgcagtg gcacaatctt ggctcactac aacctccacc tcccaggttc   2040
aaacaatcct tgtgcttcag cctcccgagt agttgggatt acaggtgtgt gccaccgtgc   2100
ccagctatat tttttgtatt tttagcagag atgggatttt gccacattgg ccaggctggt   2160
cttgaactcc tggcctcaag caatcctccc accttagcct cccaaagtgc tgagccacca   2220
cacctggccg caactgattt ttaatcatga aatgacacat acatttaaaa aacccaatac   2280
ctataatatt cctggctagt actcttcaca tctatatcat caaaaacaaa gaaagtatgt   2340
gaaactgaca cagccaaggg gagactaagg agacataaca attaactgta atgtggtatt   2400
ctggagggga tcctggaaca gaaaaagaca ttaggcaaaa aactaaagaa atctgaataa   2460
aatgtggatg tcagttaata ataatgtatc atattagtcc agtaattgta acaaatatac   2520
cacaataatg aaagccatta attataggga aaatggaggg gttaatatgg gtggctggct   2580
tttgctattt ctagcagctc cattttatct gcaaaagaca aacattcatt aagtcccaaa   2640
aaggtaaaga atgacaaatt aagcatgtat cttattagta agagtaatat aaagatgctc   2700
actcctattt ataaatattt gacaatcatg ttaaggccac aaaagagaaa aaagggtagg   2760
ggcaaaaaac gcaaagagaa aggagttagt atcttttctc ccgcactcat tagctattaa   2820
aagaggatgt ttgtttaaag ctgctcagag ctggtaaact aatgttaagt cactaacggg   2880
aatttaaaag gtttcattaa gaactgcctg cactagattc ctccaccctg agacattaaa   2940
caatcacgat aaacctcctg agtggtaaga acttgtccat ttaaaaacag gctatagatt   3000
gtatcatgca gttttatcta ctaatcggct aatatcccgc caaaaacaaa aaaccccaaa   3060
gggatgaaag tttcatccat caaaggaaac aac                               3093
```

```
<210> SEQ ID NO 16
<211> LENGTH: 3099
<212> TYPE: DNA
<213> ORGANISM: Homo sapiens

<400> SEQUENCE: 16

attcactatc acaagaacag cacgggtaag acctgtcccc atgattcagt tacctcccac     60
tgggtccctc ccacaacgca tgggaattca ggatgagatt tgggtgggga cacaaccaaa    120
ccctatcatt ccacccatgg cccctcccaa atttcatgtc ctcacatttc aaaaccaatc    180
acaccatccc aacagtccct caaagtctta aatgatttca gcattaactc aaaagtccac    240
agtctaatgt ctcatctgag acaaggcaag tcctttccat ttatgagcct ataaaatcca    300
aagcaagtta gttacttcct agatacaatg ggggtacagg cattgggtaa atacagccat    360
tccaaatggg ataaattggt caaaacaaag aggctacagg cccatgagag tccaaaatcc    420
agtggggcag tcaaatctta aagctccaaa atgatctcct ttgactccac atctcacatc    480
caggtcacgc agatggaagg ggtgggttcc catggtcttg ggcagctctg cccctgtacc    540
tttgcagggt acagcctccc tctcagctgc tttcatgggc tggcattgag tgtctgcagc    600
ttttccaggt acacggtgca agctgtcggt ggatctacca ttctggggtc tggaggacct    660
```

-continued

```
cttctcacag ctccactagg tggtgcccca gtagggactg tgtgtggggt ctctgacccc    720
acatttccct tctgcactgc cctggcagag gatctccatg agggccctgc tcctgcagca    780
aacttctgac tgggcatcca ggcatttccg cacatcctct ttaatctagg cgaaggtttc    840
caaaccccaa ttcttgactt ctgtgcactc gcagtctcaa caccacatgg aagctgtcaa    900
ggcttggggc ttgcactccc cgaagctaca gcccaagctc taccttgcct cccgtcagtc    960
atggttggga gtggctggga tgcagggcac caagtcccta ggctgcacac agcatgagga   1020
ccccgggcct ggccaacaaa accatttttt cctgatacct ctggacctgt gatgggaggg   1080
gttgccataa agacctctga catgccctgg agacattttc cccattgtct tgggaattag   1140
catttggctc ctgttactca tgcaaatttc tgcagccagc ttgaatttct cctcagaaaa   1200
tgggaatttt tcttttctat cacattgtca ggctgcaaat tttccgaact tttatgctct   1260
gcttccctta taaaactgaa tgtctttaac agcacccaag tcacctcttg aatgctttgc   1320
tgcttagaaa tttctcctgc cagatactct aaatcatctc tctgaagttc aaagttctac   1380
aaatatctcg tgcaggggca aaatgccgcc agtatctttg ctaaaacata acaagagtcc   1440
cctttgctcc agttcccaac aagttcctca tttccgtctg agaccacctc agcctatgga   1500
ctttattgtc cacagtgcta tcagcatttt gggcaaagcc attcaacaag tctctaggaa   1560
gttccaaact ttcccacatt tgcctgtctt cttctgagcc ctccaaactg ttccaaaccc   1620
tgcctgttac ccagttccaa agtcacatac ccatttttga gtatctacgg cagcacccca   1680
ctctactggt accaatttag ccactgaagt agttggagaa cagaagtaat agactctggt   1740
ttacattgta aaagcttctc tgtggctgct gtgtgaagaa aatatatgag aatgaagccc   1800
caagatgaag cagggacaca gttgcagtgg ttagagtaag aaatgctgct ggctggcact   1860
gaagtgatag cctggaggtt tgtgtgtgca catgcatgtg tatgtgtttt acgatagtag   1920
gcccaacaga tactgtaatc cacacttgtt tttttttttt ttttgagaca gagtctcacc   1980
tgttgcctag actagaatgc agtggcacaa tcttggctca ctacaacctc cacctcccag   2040
gttcaaacaa tccttgtgct tcagcctccc gagtagttgg gattacaggt gtgtgccacc   2100
gtgcccagct atattttttg tatttttagc agagatggga ttttgccaca ttggccaggc   2160
tggtcttgaa ctcctggcct caagcaatcc tcccacctta gcctcccaaa gtgctgagcc   2220
accacacctg gccgcaactg atttttaatc atgaaatgac acatacattt aaaaaaccca   2280
atacctataa tattcctggc tagtactctt cacatctata tcatcaaaaa caaagaaagt   2340
atgtgaaact gacacagcca aggggagact aaggagacat aacaattaac tgtaatgtgg   2400
tattctggag gggatcctgg aacagaaaaa gacattaggc aaaaaactaa agaaatctga   2460
ataaaatgtg gatgtcagtt aataataatg tatcatatta gtccagtaat tgtaacaaat   2520
ataccacaat aatgaaagcc attaattata gggaaaatgg aggggttaat atgggtggct   2580
ggcttttgct atttctagca gctccatttt atctacaaaa gacaaacatt cattaagtcc   2640
caaaaaggta aagaatgaca aattaagcat gtatcttatt agtaagagta atataaagat   2700
gctcactcat atttataaat atttgacaat gatgttaagg ccagaaaaga gaaaaaaggg   2760
taggggcaaa aaacgcaaag agaaaggagt tagtatcttt tctcccgcac tcattagcta   2820
ttaaaagagg atgtttgttt aaagctgctc agagctggta aactaatgtt aagtcactaa   2880
cgggaattta aaaggtttca ttaagaactg cctgcactag attcctccac cctgagacat   2940
taaacaatca cgataaacct cctgagtggt aagaacgtgt ccatttaaaa acaggctata   3000
gattgtcatg cagttttatc tactaatcgg ctaatgcacc gccaaaaaca aacaaaaaaa   3060
```

cccaaaggga tgaaagtttc atccatcaaa ggaaacaac 3099

<210> SEQ ID NO 17
<211> LENGTH: 3099
<212> TYPE: DNA
<213> ORGANISM: Homo sapiens

<400> SEQUENCE: 17
attcactatc acgagaacag cacgggtaag acctgtcccc atgattcagt tacctcccac 60
tgggtccctc ccacaacgca tgggaattca ggatgagatt tgggtgggga cacaaccaaa 120
ccctatcatt ccacccatgg cccctcccaa atttcatgtc ctcacatttc aaaaccaatc 180
acaccatccc aacagtccct caaagtctta aatgatttca gcattaactc aaaagtccac 240
agtctaatgt ctcatctgag acaaggcaag tcctttccat ctatgagcct ataaaatcca 300
aagcaagtta attacttcct agatacaatg gggtacagg cattgggtaa atacagccat 360
tccaaatggg ataaattggt caaaacaaag aggctacagg cccatgagag tccaaaatcc 420
agtggggcag tcaaatctta aagctccaaa atgatctcct cttgactcca catctcacat 480
ccaggtcacg cagatggaag ggtgggttc ccatggtctt gggcagctct gcccctgtac 540
ctttgcaggg tacagcctcc ctctcagctg ctttcatggg ctggcattga gtgtctgcaa 600
cttttccagg tacacggtgc aagctgtcgg tggatctacc attctggggt ctggaggacc 660
tcttctcaca gctccactag gtggtgcccc agtagggact gtgtgtgggg tctctgaccc 720
cacatttccc ttctgcactg ccctggcaga ggatctccat gagggccctg cccctgcagc 780
aaacttctgc ctgggcatcc aggcatttcc gcacatcctc tttaatctag gcgaaggttt 840
ccaaacccca gttcttgact tctgtgcact cgcagtctca acaccacatg gaagctgtca 900
aggcttgggg cttgcactcc ccgaagctac agcccaagct ctaccttgcc tcctgtcagt 960
catggttggg agtggctggg atgcagggca ccaagtccct aggctgcaca cagcatgagg 1020
accccgggcc tggccaacaa aaccattttt tcctgatatc tctggacctg tgatgggagg 1080
ggttgccata aagacctctg acatgccctg gagacatttt ccccattgtc ttgggaatta 1140
gcatttggct cctgttactc atgcaaattt ctgcagccag cttgaatttc tcctcagaaa 1200
atgggaattt ttcttttcta tcacattgtc aggctgcaaa ttttccgaac ttttatgctc 1260
tgcttccctt ataaaactga atgtctttaa cagcacccaa gtcacctctt gaatgctttg 1320
ctgcttagaa atttctcctg ccagatactc taaatcatct ctctgaagtt caaagttcta 1380
caaatatctc gtgcaggggc aaaatgccgc cagtatcttt gctaaaacat aacaagagtc 1440
ccctttgctc cagttcccaa caagttcctc atttccgtct gagaccacct cagcctatgg 1500
actttattgt ccacagtgct atcagcattt tgggcaaagc cattcaacaa gtctctagga 1560
agttccaaac tttcccacat ttgcctgtct tcttctgagc cctccaaact gttccaaacc 1620
ctgcctgtta cccagttcca aagtcacata cccatttttg agtatctacg gcagcacccc 1680
actctactgg taccaattta gccactgaag tagttggaga acagaagtaa tagactctgg 1740
tttacattgt aaaagcttct ctgtggctgc tgtgtgaaga aaatatatga gaatgaagcc 1800
ccaagatgaa gcagggacac agttgcagtg gttagagtaa gaaatgctgc tggctggcac 1860
tgaagtgata gcctggaggt ttgtgtgtgc acatgcatgt gtatgtgttt tacgatagta 1920
ggcccaacag atactgtaat ccacacttgt tttttttttt tttttgagac agagtctcac 1980
ctgttgccta gactagaatg cagtggcaca atcttggctc actacaacct ccacctccca 2040

```
ggttcaaaca atccttgtgc ttcagcctcc cgagtagttg ggattacagg tgtgtgccac   2100

cgtgcccagc tatatttttt gtatttttag cagagatggg attttgccac attggccagg   2160

ctggtcttga actcctggcc tcaagcaatc ctcccacctt agcctcccaa agtgctgagc   2220

caccacacct ggccgcaact gatttttaat catgaaatga cacatacatt taaaaaaccc   2280

aatacctata atattcctgg ctagtactct tcacatctat atcatcaaaa acaaagaaag   2340

tatgtgaaac tgacacagcc aaggggagac taaggagaca taacaattaa ctgtaatgtg   2400

gtattctgga ggggatcctg gaacagaaaa agacattagg caaaaaacta aagaaatctg   2460

aataaaatgt ggatgtcagt taataataat gtatcatatt agtccagtaa ttgtaacaaa   2520

tatacccaat aatgaaagcc attaattata gggaaaatgg aggggttaat atgggtggct   2580

ggcttttgct atttctagca gctccatttt atctacaaaa gacaaacatt cattaagtcc   2640

caaaaaggta aagaatgaca aattaagcat gtatcttatt agtaagagta atataaagat   2700

gctcactcat atttataaat atttgacaat gatgttaagg ccagaaaaga gaaaaaaggg   2760

taggggcaaa aaacgcaaag agaaaggagt tagtatcttt tctcccgcac tcattagcta   2820

ttaaaagagg atgtttgttt aaagctgctc agagctggta aactaatgtt aagtcactaa   2880

cgggaattta aaaggtttca ttaagaactg cctgcactag attcctccac cctgagacat   2940

taaacaatca cgataaacct cctgagtggt aagaacgtgt ccatttaaaa acaggctata   3000

gattgtcatg cagttttatc tactaatcgg ctaatgcacc gccaaaaaca aacaaaaaaa   3060

cccaaaggga tgaaagtttc atccatcaaa ggaaacaac                          3099
```

<210> SEQ ID NO 18
<211> LENGTH: 9241
<212> TYPE: DNA
<213> ORGANISM: Homo sapiens

<400> SEQUENCE: 18

```
ctagaaaaca ctttgtcatt ttagaggtgt tatccaatgt tcgcgcaggc actggagtca     60

gagaaaatgg agttgaatcc tttctctgcc actctttgag gagaatctca ccatttatta    120

tgcactgtag aatacaacaa taaaatacag ccatgtacca cataacaaca tcttggtaaa    180

caacagactg catatatgat ggtggtcatc cagtaagcta aggttaattt attattattc    240

cctttttttt ttcttttttt tgagatgtag tcttactctg tcacccaggc tagagtgcaa    300

tggcaccatc ttggctcact gcaacctctg cctcctgggt tcaagcgaat ctcctgcctc    360

agcctccgaa gtagctggga attacaggca cccaccacat ctggctaatt ttttgtattt    420

ttagtaaaga tggggtttca ccatgttggc caggctgatc tcaaactcct gacctcaagt    480

gatctgcctg cctcggcctc ccaaagtgct gggaccatag gcctgagcca ctgtgcccgg    540

ccttgtttgc ttttttaaca gttaacagtg tgctcataga aactgctttg acatgactgc    600

aatcatgtgc ttcatagaaa cttaattaga ttataccact agagtcttca gatttttata    660

cttttttttt tgaaacggag tctcactctg tcaccaggct ggagtgcagt gccgcaatct    720

cagctcgccg caacctccgc ctcccaggtt caagtgattc tcctgcctca gcctcccgag    780

tagctgggat tacaagtgca cactaccacg cccagctaat ttttgcattt ttactagaca    840

gggtttcacc atgttggcta ggatagtttc accaggatct cttggcctca tgatcagcct    900

gcctcggcct cccaaagtgc tgggattaca ggtgtgagcc accgtgccca gcctatactt    960

cccttttttga ataccatttg gcgttttgaa gaattaacag ctttgtgaac gtggcagtgc   1020

ttgtgattca ggcttccact gagaccaagg ggagaacctg gttgcaggac aaacagacgg   1080
```

```
acagcgtgtg gcagtgttta aatgctcttc tgaaggctga tacgacagct ctctgtgcac   1140
tgattgtata cgcatcccaa gattatatta ttgttttcta ttgctatgtg tcacactttg   1200
ccaaacagga tgtggaaaat gaataagcgg ttttcttagg cacttcttaa cagacaattg   1260
gtcaaaatga actccattgc ttaagaaaca cataaacacc atttagtcac tgaatatagc   1320
tatatgtatg gttgctacta tggggaatct tgttttgcca attttctttg aaaattctgg   1380
cagaccaagg ttctttttgt ttacacaata cttgaaaaat aaaaatgaac aagccaacaa   1440
actaccaagt tttcacttac ataaatgtag ttacatacag aaaatgtgac tgtgaatttt   1500
ttctaggact tttaaactat aagcactatt tgcacgaaag agaaccaatc tatcaattac   1560
aaactcacat aattttacag attttttttt ccctacacag cacataaaac agaaggaatt   1620
tgaagccacc ctccaaacac aggggaagga ggctgtgtgt atatcctcat tgtctttcac   1680
attctaaggt ggttccactc agtgactgaa atccttaagt gttgtattag tcggcttggg   1740
ctaccataac agcagcttaa actgttgtta agccactcag acttaaacaa cagaaattta   1800
tttccttata gttctggagg ctggaagttc aaggtgccgg caaggctggt ttctggtgag   1860
acctctctcc ctgtcttgca gatggctgcc tcctccctgt gtcctcatag agcctgtcct   1920
ctgcttttac acttctggtg tcatcttcct tttttttttt tttttgagac agagtctcgc   1980
tctatcgccc aggctggagt gcagtggccc gatcgatctc ggctcactgc aacctctgcc   2040
tcccaggttc aagcaattct cctgcctcag cctcccgagt agctgggact acaggtgccc   2100
gccatcatgt ctggctaatt tttgtatttt tagtagagac agggtttcac catattggcc   2160
aggctggtct ccaactcctg accttgtcat ctgcctgcct cggcctccca aagtgctagg   2220
attacaggcg tgagccaccg cacccggcct ctttctcttc ttataaggac accagtccta   2280
ttagattagg gctccaccct catgacctca tttgacctta actattattt ctttaaagca   2340
cctatttcca aatatagtca ctttaggggt tagggcttca aaatatgaat ctgagggaga   2400
tcaattcagt aaatagcagt agtcattaac ggacaatata tacaaagata atttcgtgat   2460
tactgtcctt atgcataaat gtcctcagtg ttccactgcc tttatccaga tttactatca   2520
caaagacttt gctctgagaa aaatgtgatt tctttctttt tttttttttt ttgagacaga   2580
gtctcactct gtcacccagg ctggagtgca gtggtgcaat ctcggctcac tgcaatctcc   2640
gcctcccagg ttcacgccat tctcttgcct cagtctcccg agtagctggg cctacaggcg   2700
cccgccaccc tgcccagcta atttttgta tttttagtag agacggggtt tcaccatgtt   2760
agccaggatg gtctcaatct cctgacctcg tgatccacct gcctcagcct cccaaagtgc   2820
tgggattaca ggcatgagcc accgcgccca gcagattttt tttttttttt tttttttttg   2880
agatggagtc ttgctgtgtt gcccagcctg gagtgcagtg ttatgatttt ggctcactgc   2940
aacctctgtc taccatgttc aagcgattct cccacctctg cctcccgtgt agctgggatc   3000
acaggcacac gccaccacac ctagctactt tttgtatttt tagtagaaat ggggtttcac   3060
catgttggcc aggatggtcc cgaactcctg acctcaagtg atcctcctgc ctcggcctcc   3120
caaagtgctg ggattacagg tgtgagccac tgtgcctggc caaaaatgtg atttcttatt   3180
tcccacattg ccaattccat ttcaattaac tataatagct atgtctattg agcactcaag   3240
tgtattctag aaactgttcc tgattctggg gatatatcca tgaatcaact atagtccctg   3300
ttattaagta atctgtagtc tgactaaacc attagaaatt taaaaaatgg ctactttcaa   3360
agacatcttg gagttcagga gtcccacact gcgaaccata ttacctaata atccaacctg   3420
```

```
cttgtaattc acttatttaa ccaatattta ttgagtgcca actttgagcc taagatacag   3480
cagtaaacaa atggataaag tccctgtcct catgaaactt gtattctaat ggaagaaaca   3540
gaaaacaaac agatatagga tgtaatatca ggtagggata aatactttga attcaaacaa   3600
aagtatacgt agtcagggtt cgccaaagag acacagccaa tcggatacat agatatataa   3660
aagagggttt atgagttaga aagggctcac atgattacag aggctgagaa gtcccacagc   3720
agattgtctg caagctggag acccagggat actggtagca tggctcagtc caagtcccaa   3780
agcctcagaa tcaggaaagc tgatgatata attcttagcc caaaggcctt agaaccccag   3840
cggtgacgga aaggctgatg taggtcctgg agtcctgaga cccaacagcc tgggatcctg   3900
aaatccaagg gcaggaatgg aagcgtgtat tccagctcca agagagtaag accaatttgc   3960
ctttcttccg tttttgtttc aagccacctg cacattgagg gcggatggtt ccctcttagt   4020
ccattcagtc atatatcaat ctcttctgga aataccctca cagacacact aacaaataat   4080
gcctttccag ttctctaggt attctttaat ccagtcaagc tgacacctaa aattaaccat   4140
cacaaaagtt aaggagaaag aagacaactt gtaggggagg ctgctatgca agacagtgtg   4200
tgaaggaagg gctctctgaa gaggttaata tctgagcaga gacttgaatg aagtgaagaa   4260
gtgagccatg tgggtatggg gaatacaact tccaggtaga gaagacaagt gtggtgtgta   4320
tcagggtcag caaagaagcc atgtgacaga gaagggtggg ccagggagag acggataagt   4380
gatctaactc ctgaggaggt ggcctggcca ggagctagag catgaagatc tcgtaggact   4440
ttattctgca aggtgaaaag ccattgtatt agtctgttca caaacccgag actaggcaat   4500
ttacaaaaga aagagaggtt taatggactt acagttccac atggctgggg aggcctcaca   4560
atcatggcga aaggcaatga ggagcaagtc acgtcttacg tggatggcag gcaaagacaa   4620
agacagcttg tgcagagaaa ctccccctta tagagccatc agatcctgtt agacttattc   4680
actatcacaa gaacagcacg ggtaagacct gtccccatga ttcagttacc tcccactggg   4740
tccctcccac aacgcatggg aattcaggat gagatttggg tggggacaca accaaaccct   4800
atcattccac ccatggcccc tcccaaattt catgtcctca catttcaaaa ccaatcacac   4860
catcccaaca gtccctcaaa gtcttaaatg atttcagcat taactcaaaa gtccacagtc   4920
taatgtctca tctgagacaa ggcaagtcct ttccatttat gagcctataa aatccaaagc   4980
aagttagtta cttcctagat acaatggggg tacaggcatt gggtaaatac agccattcca   5040
aatgggataa attggtcaaa acaaagaggc tacaggccca tgagagtcca aaatccagtg   5100
gggcagtcaa atcttaaagc tccaaaatga tctcctttga ctccacatct cacatccagg   5160
tcacgcagat ggaaggggtg ggttcccatg gtcttgggca gctctgcccc tgtacctttg   5220
cagggtacag cctccctctc agctgctttc atgggctggc attgagtgtc tgcagctttt   5280
ccaggtacac ggtgcaagct gtcggtggat ctaccattct ggggtctgga ggacctcttc   5340
tcacagctcc actaggtggt gccccagtag ggactgtgtg tggggtctct gaccccacat   5400
ttcccttctg cactgccctg gcagaggatc tccatgaggg ccctgctcct gcagcaaact   5460
tctgactggg catccaggca tttccgcaca tcctctttaa tctaggcgaa ggtttccaaa   5520
ccccaattct tgacttctgt gcactcgcag tctcaacacc acatggaagc tgtcaaggct   5580
tggggcttgc actccccgaa gctacagccc aagctctacc ttgcctcccg tcagtcatgg   5640
ttgggagtgg ctgggatgca gggcaccaag tccctaggct gcacacagca tgaggacccc   5700
gggcctggcc aacaaaacca ttttttcctg atacctctgg acctgtgatg ggaggggttg   5760
ccataaagac ctctgacatg ccctggagac attttcccca ttgtcttggg aattagcatt   5820
```

```
tggctcctgt tactcatgca aatttctgca gccagcttga atttctcctc agaaaatggg   5880
aatttttctt ttctatcaca ttgtcaggct gcaaattttc cgaactttta tgctctgctt   5940
cccttataaa actgaatgtc tttaacagca cccaagtcac ctcttgaatg ctttgctgct   6000
tagaaatttc tcctgccaga tactctaaat catctctctg aagttcaaag ttctacaaat   6060
atctcgtgca ggggcaaaat gccgccagta tctttgctaa aacataacaa gagtcccctt   6120
tgctccagtt cccaacaagt tcctcatttc cgtctgagac cacctcagcc tatggacttt   6180
attgtccaca gtgctatcag cattttgggc aaagccattc aacaagtctc taggaagttc   6240
caaactttcc cacatttgcc tgtcttcttc tgagccctcc aaactgttcc aaaccctgcc   6300
tgttacccag ttccaaagtc acatacccat ttttgagtat ctacggcagc accccactct   6360
actggtacca atttagccac tgaagtagtt ggagaacaga agtaatagac tctggtttac   6420
attgtaaaag cttctctgtg gctgctgtgt gaagaaaata tatgagaatg aagccccaag   6480
atgaagcagg gacacagttg cagtggttag agtaagaaat gctgctggct ggcactgaag   6540
tgatagcctg gaggtttgtg tgtgcacatg catgtgtatg tgttttacga tagtaggccc   6600
aacagatact gtaatccaca cttgtttttt tttttttttt gagacagagt ctcacctgtt   6660
gcctagacta gaatgcagtg gcacaatctt ggctcactac aacctccacc tcccaggttc   6720
aaacaatcct tgtgcttcag cctcccgagt agttgggatt acaggtgtgt gccaccgtgc   6780
ccagctatat tttttgtatt tttagcagag atgggatttt gccacattgg ccaggctggt   6840
cttgaactcc tggcctcaag caatcctccc accttagcct cccaaagtgc tgagccacca   6900
cacctggccg caactgattt ttaatcatga aatgacacat acatttaaaa aacccaatac   6960
ctataatatt cctggctagt actcttcaca tctatatcat caaaaacaaa gaaagtatgt   7020
gaaactgaca cagccaaggg gagactaagg agacataaca attaactgta atgtggtatt   7080
ctggagggga tcctggaaca gaaaaagaca ttaggcaaaa aactaaagaa atctgaataa   7140
aatgtggatg tcagttaata ataatgtatc atattagtcc agtaattgta acaaatatac   7200
ccaataatga aagccattaa ttataggaa aatggagggg ttaatatggg tggctggctt    7260
ttgctatttc tagcagctcc attttatcta caaaagacaa acattcatta agtcccaaaa   7320
aggtaaagaa tgacaaatta agcatgtatc ttattagtaa gagtaatata aagatgctca   7380
ctcatattta taaatatttg acaatgatgt taaggccaga aaagagaaaa aagggtaggg   7440
gcaaaaaacg caaagagaaa ggagttagta tcttttctcc cgcactcatt agctattaaa   7500
agaggatgtt tgtttaaagc tgctcagagc tggtaaacta atgttaagtc actaacggga   7560
atttaaaagg tttcattaag aactgcctgc actagattcc tccaccctga gacattaaac   7620
aatcacgata aacctcctga gtggtaagaa cgtgtccatt taaaaacagg ctatagattg   7680
tcatgcagtt ttatctacta atcggctaat gcaccgccaa aaacaaacaa aaaaacccaa   7740
agggatgaaa gtttcatcca tcaaaggaaa caacagtcac cttggttccc atcccactca   7800
tatactgccg ccgtacatgt caatcagatg aacctgtgcg tatctcttaa cgacaattga   7860
cccacctttt taactgaagt gaagggggt tctgctccgc gaccacttcc tggatctctc    7920
ccttcaccct ctgtgttctt tcgggtgcac catcgggtca aagccgcagc aacgccgtct   7980
ctgtgtgatc gcatgtgccc ttctgcacac gaccttcccc cgagagtgac cagctaccgg   8040
acaggcacca aggagggcta ccgagcacct cccggaccgg cggctgcagg atcgcgagcg   8100
cctccgctag ggagaccgca cgttgcgcct gtgcttcctg cggtggcgcc ttctgcaagg   8160
```

-continued

```
agacctcgac cctgctccct ctccggggct ggatctgact ccttgacggt gattccagac   8220

gcgagaccca aactgacggc ttctagaaga ggggcgagcc cggccgcaag tctttcacgt   8280

agctaagtca tcgttgcttc cggcttctta ccgttctccc ctttgtaaac ggttacctcc   8340

cgaaaaccca ggctctcctc caacagtggt tctcaagcga ggcgatcttc cccgggaggg   8400

gatatttggc aaagtctggg ggcatttttg gttcactggg gctgctactt gcatccactg   8460

ggtagaggcg ggggatgcag ctacacaacc tgcgaagcac gggacagcac cctccccaac   8520

ccagacagaa ttagccggcc caaaacctca gtagtgccca ggctgagaaa ccctgcctta   8580

aacaaacaac aaagaaaggc caagtcccat aagtgggtca ccgcgccgag actggggtcc   8640

acgggacacc ccagccacgc caagccggga agtccccgcc tcctggagct gaacccgccc   8700

ctctcccaga ggtggagctg cggggggcgg gaacaggcac ggagaaaata aacaagacta   8760

aaaagtcctg agtagcgctg tgtggccgca aacctgaacc caccttttgc accacgcggg   8820

acccggcact cttcctgcca cccacccctg agagggctgc gcggccgacc ccagtactag   8880

aaaacactcg tcacctcact caagacgggt acgaaggcca acggacgcct tcctttagaa   8940

cgctcagcac acagagcaac ttctcacgcc tactctcaaa tggcgtactc caaactagca   9000

ctcccgacgt ccagctgtga acccagagcg gcggaaagcc cctgaaccca gcgcccgggc   9060

atgcgcagac gcgttgttgt ggtgggcgtg gctccctccg gacccggcgc cccgccctcc   9120

gccccgtgtc cgcatgcgcg actgagccgg gtggatggta ctgctgcatc cgggtgtctg   9180

gaggctgtgg ccgttttgtt ttcttggcta aaatcggggg agtgaggcgg gccggcgcgg   9240

c                                                                   9241
```

<210> SEQ ID NO 19
<211> LENGTH: 9236
<212> TYPE: DNA
<213> ORGANISM: Homo sapiens

<400> SEQUENCE: 19

```
ctagaaaaca ctttgtcatt ttagaggtgt tatccaatgt tcgcgcaggc actggagtca     60

gagaaaatgg agttgaatcc tttctctgcc actctttgag gagaatctca ccatttatta    120

tgcactgtag aatacaacaa taaaatacag ccatgtacca cataacaaca tcttggtaaa    180

caacagactg catatatgat ggtggtcatc cagtaagcta aggttaattt attattattc    240

cctttttttt ttcttttttt tgagatgtag tcttactctg tcacccaggc tagagtgcaa    300

tggcaccatc ttggctcact gcaacctctg cctcctgggt tcaagcgaat ctcctgcctc    360

agcctccgaa gtagctggga attacaggca cccaccacat ctggctaatt ttttgtattt    420

ttagtaaaga tggggtttca ccatgttggc caggctgatc tcaaactcct gacctcaagt    480

gatctgcctg cctcggcctc ccaaagtgct gggaccatag gcctgagcca ctgtgcccgg    540

ccttgtttgc ttttttaaca gttaacagtg tgctcataga aactgctttg acatgactgc    600

aatcatgtgc ttcatagaaa cttaattaga ttataccact agagtcttca gatttttata    660

cttttttttt tgaaacggag tctcactctg tcaccaggct ggagtgcagt gccgcaatct    720

cagctcgccg caacctccgc ctcccaggtt caagtgattc tcctgcctca gcctcccgag    780

tagctgggat tacaagtgca cactaccacg cccagctaat ttttgcattt ttactagaca    840

gggtttcacc atgttggcta ggatagtttc accaggatct cttggcctca tgatcagcct    900

gcctcggcct cccaaagtgc tgggattaca ggtgtgagcc accgtgccca gcctatactt    960

ccctttttga ataccatttg gcgttttgaa gaattaacag ctttgtgaac gtggcagtgc   1020
```

```
ttgtgattca ggcttccact gagaccaagg ggagaacctg gttgcaggac aaacagacgg   1080

acagcgtgtg gcagtgttta aatgctcttc tgaaggctga tacgacagct ctctgtgcac   1140

tgattgcata cgcatcccaa gattatatta ttgttttcta ttgctatgtg tcacactttg   1200

ccaaacagga tgtggaaaat gaataagcgg ttttcttagg cacttcttaa cagacaattg   1260

gtcaaaatga actccattgc ttaagaaaca cataaacacc atttagtcac tgaatatagc   1320

tatatgtatg gttgctacta tggggaatct tgttttgcca attttctttg aaaattctgg   1380

cagaccaagg ttctttttgt ttacacaata cttgaaaaat aaaaatgaac aagccaacaa   1440

actaccaagt tttcacttac ataaatgtag ttacatacag aaaatgtgac tgtgaatttt   1500

ttctaggact tttaaactat aagcactatt tgcacgaaag agaaccaatc tatcaattac   1560

aaactcacat aattttacag attttttttt ccctacacag cacataaaac agaaggaatt   1620

tgaagccacc ctccaaacac aggggaagga ggctgtgtgt atatcctcat tgtctttcac   1680

attctaaggt ggttccactc agtgactgaa atccttaagt gttgtattag tcggcttggg   1740

ctaccataac agcagcttaa actgttgtta agccactcag acttaaacaa cagaaattta   1800

tttccttata gttctggagg ctggaagttc aaggtgccgg caaggctggt ttctggtgag   1860

acctctctcc ctgtcttgca gatggctgcc tcctccctgt gtcctcatag agcctgtcct   1920

ctgcttttac acttctggtg tcatcttcct tttttttttt tttttgagac agagtctcgc   1980

tctatcgccc aggctggagt gcagtggccc gatcgatctc ggctcactgc aacctctgcc   2040

tcccaggttc aagcaattct cctgcctcag cctcccgagt agctgggact acaggtgccc   2100

gccatcatgt ctggctaatt tttgtatttt tagtagagac agggtttcac catattggcc   2160

aggctggtct ccaactcctg accttgtcat ctgcctgcct cggcctccca aagtgctagg   2220

attacaggcg tgagccaccg cacccggcct ctttctcttc ttataaggac accagtccta   2280

ttagattagg gctccaccct catgacctca tttgacctta actattattt ctttaaagca   2340

cctatttcca aatatagtca ctttaggggt tagggcttca aaatatgaat ctgagggaga   2400

tcaattcagt aaatagcagt agtcattaac ggacaatata tacaaagata atttcgtgat   2460

tactgtcctt atgcataaat gtcctcagtg ttccactgcc tttatccaga tttactatca   2520

caaagacttt gctctgagaa aaatgtgatt tctttctttt tttttttttt ttgagacaga   2580

gtctcactct gtcacccagg ctggagtgca gtggtgcaat ctcggctcac tgcaatctcc   2640

gcctcccagg ttcacgccat tctcttgcct cagtctcccg agtagctggg cctacaggcg   2700

cccgccaccc tgcccagcta atttttgta tttttagtag agacggggtt tcaccatgtt   2760

agccaggatg gtctcaatct cctgacctcg tgatccacct gcctcagcct cccaaagtgc   2820

tgggattaca ggcatgagcc accgcgccca gcagattttt tttttttttt tttttttttg   2880

agatggagtc ttgctgtgtt gcccagcctg gagtgcagtg ttatgatttt ggctcactgc   2940

aacctctgtc taccatgttc aagcgattct cccacctctg cctcccgtgt agctgggatc   3000

acaggcacac gccaccacac ctagctactt tttgtatttt tagtagaaat ggggtttcac   3060

catgttggcc aggatggtcc cgaactcctg acctcaagtg atcctcctgc ctcggcctcc   3120

caaagtgctg ggattacagg tgtgagccac tgtgcctggc caaaaatgtg atttcttatt   3180

tcccacattg ccaattccat ttcaattaac tataatagct atgtctattg agcactcaag   3240

tgtattctag aaactgttcc tgattctggg gatatatcca tgaatcaact atagtccctg   3300

ttattaagta atctgtagtc tgactaaacc attagaaatt taaaaaatgg ctactttcaa   3360
```

-continued

```
agacatcttg gagttcagga gtcccacact gcgaaccata ttacctaata atccaacctg   3420
cttgtaattc acttatttaa ccaatattta ttgagtgcca actttgagcc taagatacag   3480
cagtaaacaa atggataaag tccctgtcct catgaaactt gtattctaat ggaagaaaca   3540
gaaaacaaac agatatagga tgtaatatca ggtagggata aatactttga attcaaacaa   3600
aagtatacgt agtcagggtt cgccaaagag acacagccaa tcggatacat agatatataa   3660
aagagggttt atgagttaga aagggctcac atgattacag aggctgagaa gtcccacagc   3720
agattgtctg caagctggag acccagggat actggtagca tggctcagtc caagtcccaa   3780
agcctcagaa tcaggaaagc tgatgatata attcttagcc caaaggcctt agaaccccag   3840
cggtgacgga aaggctgatg taggtcctgg agtcctgaga cccaacagcc tgggatcctg   3900
aaatccaagg gcaggaatgg aagcgtgtat tccagctcca agagagtaag accaatttgc   3960
ctttcttccg tttttgtttc aagccacctg cacattgagg gcggatggtt ccctcttagt   4020
ccattcagtc atatatcaat ctcttctgga aataccctca cagacacact aacaaataat   4080
gcctttccag ttctctaggt attctttaat ccagtcaagc tgacacctaa aattaaccat   4140
cacaaaagtt aaggagaaag aagacaactt gtaggggagg ctgctatgca agacagtgtg   4200
tgaaggaagg gctctctgaa gaggttaata tctgagcaga gacttgaatg aagtgaagaa   4260
gtgagccatg tgggtatggg gaatacaact tccaggtaga gaagacaagt gtggtgtgta   4320
tcagggtcag caaagaagcc atgtgacaga gaagggtggg ccagggagag acggataagt   4380
gatctaactc ctgaggaggt ggcctggcca ggagctagag catgaagatc tcgtaggact   4440
ttattctgca aggtgaaaag ccattgtatt agtctgttca caaacccgag actaggcaat   4500
ttacaaaaga aagagaggtt taatggactt acagttccac atggctgggg aggcctcaca   4560
atcatggcga aaggcaatga ggagcaagtc acgtcttacg tggatggcag gcaaagacaa   4620
agacagcttg tgcagagaaa ctccccctta tagagccatc agatcctgtt agacttattc   4680
actatcacaa gaacagcacg ggtaagacct gtccccatga ttcagttacc tcccactggg   4740
tccctcccac aacgcatggg aattcaggat gagatttggg tggggacaca accaaaccct   4800
atcattccac ccatggcccc tcccaaattt catgtcctca catttcaaaa ccaatcacac   4860
catcccaaca gtccctcaaa gtcttaaatg atttcagcat taactcaaaa gtccacagtc   4920
taatgtctca tctgagacaa ggcaagtcct ttccatttat gagcctataa aatccaaagc   4980
aagttagtta cttcctagat acaatggggg tacaggcatt gggtaaatac agccattcca   5040
aatgggataa attggtcaaa acaaagaggc tacaggccca tgagagtcca aaatccagtg   5100
gggcagtcaa atcttaaagc tccaaaatga tctcctttga ctccacatct cacatccagg   5160
tcacgcagat ggaaggggtg ggttcccatg gtcttgggca gctctgcccc tgtacctttg   5220
cagggtacag cctccctctc agctgctttc atgggctggc attgagtgtc tgcagctttt   5280
ccaggtacac ggtgcaagct gtcggtggat ctaccattct ggggtctgga ggacctcttc   5340
tcacagctcc actaggtggt gccccagtag ggactgtgtg tggggtctct gaccccacat   5400
ttcccttctg cactgccctg gcagaggatc tccatgaggg ccctgctcct gcagcaaact   5460
tctgactggg catccaggca tttccgcaca tcctctttaa tctaggcgaa ggtttccaaa   5520
ccccaattct tgacttctgt gcactcgcag tctcaacacc acatggaagc tgtcaaggct   5580
tggggcttgc actccccgaa gctacagccc aagctctacc ttgcctcccg tcagtcatgg   5640
ttgggagtgg ctgggatgca gggcaccaag tccctaggct gcacacagca tgaggacccc   5700
gggcctggcc aacaaaacca ttttttcctg atacctctgg acctgtgatg ggaggggttg   5760
```

```
ccataaagac ctctgacatg ccctggagac attttcccca ttgtcttggg aattagcatt   5820
tggctcctgt tactcatgca aatttctgca gccagcttga atttctcctc agaaaatggg   5880
aatttttctt ttctatcaca ttgtcaggct gcaaattttc cgaactttta tgctctgctt   5940
cccttataaa actgaatgtc tttaacagca cccaagtcac ctcttgaatg ctttgctgct   6000
tagaaatttc tcctgccaga tactctaaat catctctctg aagttcaaag ttctacaaat   6060
atctcgtgca ggggcaaaat gccgccagta tctttgctaa aacataacaa gagtcccctt   6120
tgctccagtt cccaacaagt tcctcatttc cgtctgagac cacctcagcc tatggacttt   6180
attgtccaca gtgctatcag cattttgggc aaagccattc aacaagtctc taggaagttc   6240
caaactttcc cacatttgcc tgtcttcttc tgagccctcc aaactgttcc aaaccctgcc   6300
tgttacccag ttccaaagtc acatacccat ttttgagtat ctacggcagc accccactct   6360
actggtacca atttagccac tgaagtagtt ggagaacaga agtaatagac tctggtttac   6420
attgtaaaag cttctctgtg gctgctgtgt gaagaaaata tatgagaatg aagccccaag   6480
atgaagcagg gacacagttg cagtggttag agtaagaaat gctgctggct ggcactgaag   6540
tgatagcctg gaggtttgtg tgtgcacatg catgtgtatg tgttttacga tagtaggccc   6600
aacagatact gtaatccaca cttgtttttt tttttgaga cagagtctca cctgttgcct    6660
agactagaat gcagtggcac aatcttggct cactacaacc tccacctccc aggttcaaac   6720
aatccttgtg cttcagcctc ccgagtagtt gggattacag gtgtgtgcca ccgtgcccag   6780
ctatattttt tgtattttta gcagagatgg gattttgcca cattggccag gctggtcttg   6840
aactcctggc ctcaagcaat cctcccacct tagcctccca aagtgctgag ccaccacacc   6900
tggccgcaac tgatttttaa tcatgaaatg acacatacat ttaaaaaacc caatacctat   6960
aatattcctg gctagtactc ttcacatcta tatcatcaaa aacaaagaaa gtatgtgaaa   7020
ctgacacagc caaggggaga ctaaggagac ataacaatta actgtaatgt ggtattctgg   7080
aggggatcct ggaacagaaa aagacattag gcaaaaaact aaagaaatct gaataaaatg   7140
tggatgtcag ttaataataa tgtatcatat tagtccagta attgtaacaa atataccaca   7200
ataatgaaag ccattaatta tagggaaaat ggaggggtta atatgggtgg ctggcttttg   7260
ctatttctag cagctccatt ttatctgcaa aagacaaaca ttcattaagt cccaaaaagg   7320
taaagaatga caaattaagc atgtatctta ttagtaagag taatataaag atgctcactc   7380
ctatttataa atatttgaca atcatgttaa ggccacaaaa gagaaaaaag ggtaggggca   7440
aaaaacgcaa agagaaagga gttagtatct tttctcccgc actcattagc tattaaaaga   7500
ggatgtttgt ttaaagctgc tcagagctgg taaactaatg ttaagtcact aacgggaatt   7560
taaaaggttt cattaagaac tgcctgcact agattcctcc accctgagac attaaacaat   7620
cacgataaac ctcctgagtg gtaagaactt gtccatttaa aaacaggcta tagattgtat   7680
catgcagttt tatctactaa tcggctaata tcccgccaaa aacaaaaaac cccaaaggga   7740
tgaaagtttc atccatcaaa ggaaacaaca gtcaccttgg ttcccatctc actcatatac   7800
tgccgccgta catgtcaatc agatgaacct gtgcgtatct cttaatgaca attgacccac   7860
atttttgact gaagtgaaag ggggttctgc tccgcgacca cttcctggat ctccccctcc   7920
accctctgtg ttctttcggg tgcaccatcg ggtcaaagcc gcagcaacgc cgtctctgtg   7980
tgatcgcatg tgcccttctg cacacgacct tcccccgaga gtgaccagct accggacagg   8040
caccaaggag ggctaccgag cacctcccgg accggcggct gcaggatcgc gagcgcctcc   8100
```

```
gctagggaga ctgcacgttg cgcctgtgct tcctgcggtg gcgccttctg caaggagacc   8160
tcgaccctgc tccctctccg gggctggatc tgactccttg acggtgattc cagacgcgag   8220
acccaaactg acggcttcta gaagaggggc gagcccggcc gcaagtcttt cacgtagcta   8280
agtcatcgtt gcttccggct tcttaccgtt ctcccctttg taaacggtta cctcccgaaa   8340
acccaggctc tcctccaaca gtggttctca agcgaggcga tcttccccgg gaggggatat   8400
ttggcaaagt ctgggggcat ttttggttca ctggggctgc tacttgcatc cactgggtag   8460
aggcggggga tgcagctaca caacctgcga agcacgggac agcaccctcc ccaacccaga   8520
cagaattagc cggcccaaaa cctcagtagt gcccaggctg agaaaccctg ccttaaacaa   8580
acaacaaaga aaagccaagt cccataagtg ggtcaccgcg ccgagactgg ggtccacggg   8640
acaccccagc cacgccaagc cgggaagtcc ccgcctcctg gagctgaacc cgcccctctc   8700
ccagaggtgg agctgcgggg ggcgggaaca ggcacggaga aaataaacaa gactaaaaag   8760
tcctgagtag cgctgtgtgg ccgcaaacct gaacccacct tttgcaccac gcgggacccg   8820
gcacgcttcc tgccacccac ccctgagagg gctgcgcggc cgaccccagt actagaaaac   8880
actcgtcacc tcaatcaaga cgggtacgaa ggccaacgga cgccttcctt tagaacgctc   8940
agcacacaga gcaacttctc acgcctactc tcaaatggcg tactccaaac tagcactccc   9000
gacgtccagc tgtgaaccca gagcggcgga aagcccctga acccagcgcc cgggcatgcg   9060
cagacgcgtt gttgtggtgg gcgtggctcc ctccggaccc ggcgccccgc cctccgcccc   9120
gtgtccgcat gcgcgactga gccgcggggg tggtactgct gcatccgggt gtctgaagat   9180
ccgatgaaat aacatatgca aaatgattgg gtccgtgatt ggcattccag aaatgg       9236
```

<210> SEQ ID NO 20
<211> LENGTH: 9238
<212> TYPE: DNA
<213> ORGANISM: Homo sapiens

<400> SEQUENCE: 20

```
aaacgctcat gacagcaaag tctccaatgt tcgcgcaggc actggagtca gagaaaatgg     60
agttgaatcc tttctctgcc actctttgag gagaatctca ccatttatta tgcactgtag    120
aatacaacaa taaaatacag ccatgtacca cataacaaca tcttggtaaa caacagactg    180
catatatgat ggtggtcatc cagtaagcta aggttaattt attattattc cttgtttttt    240
tttttttttt tttttttttg agatgtagtc ttactctgtc acccaggcta gagtgcaatg    300
gcaccatctt ggctcactgc aacctctacc tcctgggttc aagcaaatct cctgcctcag    360
cctccaaagt agctgggatt acaggcaccc accacatctg gctaattttt tgtattttta    420
gtaaagatgg ggtttcacca tgttggccag gctgatctca aactcctgac ctcaagtgat    480
ctgcccgcct cggcctccca aagtgctgga accacaggcc tgagccactg tgcccagcct    540
tggttgcttt tttaacagat aacagtgtgc tcatagaaac tgctttgaca tgactgcaat    600
catgtgcttc atagaaactt aattagatta taccactaga gtcttcagat ttttatactt    660
tttttttttg aaacggagtc tcactctgtc accaggctgg agtgcagtgc cgcaatctcg    720
gctcactgca acctccgcct cccaggttca agcaattctc ctgcctcagc ctcccgagta    780
gctgggatta caagtgcgca ctaccacacc cagctaattt ttgcattttt acttgacagg    840
gtttcaccat gttggctagg atagtttcac caggatctct tggcctcatg atcagcctgc    900
ctcggcctcc caaagtgctg ggattacagg tgtgagccac cgtgcccagc ctatacttcc    960
ctttttgaat accatttggc gttttgaaga attaacagct ttgtgaacgt ggcagtgctt   1020
```

```
gtgattcagg cttccattga gaccaagggg agaacctggt tgcaggacaa acagacggac   1080
agcgtgtggc agtgtttaaa tgctcttctg aaggctgata cgacagctct ctgtgcactg   1140
attgcatacg catcccaaga ttatattatt gttttctact gctatgtgtc acactttgcc   1200
aaacaggatg tggaaaatga ataagcggtt ttcttaggca cttcttaaca gacaattggt   1260
caaaatgaac tccattgctt aagaaacaca taaacaccat ttagtcactg aacatagcta   1320
tatgtatggt tgttactatg ggaaatcttg ttttgccaat ttctttgaa aattctggca   1380
gaccaaggtt ctttttgttt acataatact tgaaaaataa aaatgaacaa gctaacaaac   1440
taccaagttt tcacttacat aaatgtagtt gcatacagaa aatgtgactg tgaattaatt   1500
tttctaggac ttttaaacta taagcactat ttgcacaaaa gagaaccaat ctatcaatta   1560
caaactcaca taattttaca gatttttttt ttcctacaca gcacataaaa cagaaggaat   1620
ttgaagccac cctccaaaca caggggaagg aggctgtgtg tatatcctca ttgtctttca   1680
cattctaagg tggttccact cagtgactga aatccttaag cgttgtatta gtctgcttgg   1740
gctaccataa cagcagctta aactgttgtt tagccactca gacttaaaca acagaaattt   1800
atttccttat agttctggag gctggaagtt caaggtgccg gcaaggttgg tttctggtga   1860
gacctctctc cctgtcttgc agatggctgc ctcctccctg tgtcctcata gagcctgtct   1920
tctgctttta cacttctggt gtcatcttcc tttttttttt tttttttttt ttttgagaca   1980
gagtctcgct ctatcgccca ggctggagtg cagtggcccg atcgatctcg gctcactgca   2040
acctctgcct cccaggttca agcaattctc ctgcctcagc ctcccaagta gctgggacta   2100
caggtgcccg ccatcatgcc tggctaattt ttgtattttt agtagagaca gggtttcacc   2160
atattggcca ggctggtctc gaactcctga ccttgtcatc tgcctgcctc ggcctcccaa   2220
agtgctagga ttacaggcgt gagccaccgc acccggcctc ttcctcttct tataaggaca   2280
ccagtcctat tagattaggg ctccaccctc ataacctcat ttgaccttaa ctattatttc   2340
tttaaagcac ctatttccaa atatagtcac tttaggggtt agggcttcaa aagatgaatc   2400
tgagggagct caattcagta aatagcagta gtcattaatg gacaatgtat acaaagataa   2460
tttcgtgatt actgtcctta tgcataaacg tcctcagtgt tccactgcgt ttatccagat   2520
ttagtatcac aaagactttg ctctgagaaa aatgtgattt tttttttttt tttttttttg   2580
agacggagtc tcgctctgtt acccaggctg gagtgcagtg gcgcgatctc ggctcactgc   2640
aagctccgcc tcccgggttc acgccattct cctgcctcag cctccggagt agctgggact   2700
acaggcgccc gccactacgc ccggctaact tttttgtatt tttagtagag acggggtttc   2760
accatgttag ccaggatggt ctcaatctcc tgacctcgtg atccacctgc ctcagcctcc   2820
caaagtgctg ggattacagg catgagccac cgcgcccagc agattttttt tttttttttt   2880
gagatggagt cttgctctgt tgcccaacct ggagtgcagt gttatgattt tggctcactg   2940
caacctctac catgttcaag cgattctccc acctctgcct cccgtgtagc tgggatcaca   3000
ggcacacgcc accacaccta gctacttttt gtatttttag tagaaatggg gtttcaccat   3060
gttggccagg atggtcccga actcctgacc tcaagtgatc ctcctgcctc ggcctccaaa   3120
gtgctgggat tacaggtgtg agccactgtg cctggccaaa aatgtgattt cttatttccc   3180
acattgccaa ttccatttca attaactata atagctatgt ctattgagca ctcaagcgta   3240
ttctagaaac tgttcctgat tctggggata tatccatgaa tcaactatag tccctgttat   3300
taagtaatcc gtagtctgac taaaccatta gaaattaaaa aaaaatggct actttcaaag   3360
```

```
acatcttgga gttcaggagt cccacactgc gaaccatatt acctaataat ccaacctgct   3420
tgtaattcac ttatttaacc aatatttatt gagtgccaac tttgagccta agatacagca   3480
gtaaacaaat gcataaagtc cctgtcccca tgaaacttgt attctaatgg aaaaaacaga   3540
aaacaaacag atataggatg taatatcagg tagggataaa tactttgaat tcaaacaaaa   3600
gtatacgtag tcagggttcc ccagagagac acagccaatc gatacataga tatataagag   3660
agggtttatg agttagaaag ggctcacatg attacagagg ctgagaagtc ccacaacaga   3720
ttgtctgcaa gctggagacc cagggatact ggtagcatgg ctcagtccaa gtcccaaagt   3780
ctcagaatca ggaaagctga tgatataatt cttagcccaa aggccttaga accccagcgg   3840
tgacggaaag gctgatgtag gtcctggcgt cctgagaccc aacagcctgg gatcctgaaa   3900
tccaagggca ggaatggaag cgtgtattcc agctccaaga gagtaagacc aatttgcctt   3960
tcttccgttt ttgttccaag ccaactgcac gttgagggcg gatggttccc tcttagccca   4020
ttcagtcata tatcaatctc ttctggaaat accctcacag acacactaac aaataatgcc   4080
tttccagttc tctaggtatt ctttaatcca gtcaagctga cacctaaaat taaccatcac   4140
aaaagttaag gagaaagaag acaacttgta ggagaggctg ctatgcaaga cagtgtgtga   4200
aggaagggct ctctgaagag gttaatatct gagcagagac ttgaatgaag tgaagaagtg   4260
agccatgtgg gtatggggaa tacaacttcc aggtagagaa gacaagtgtg gtgtgtatca   4320
cggtcagcaa agaagccatg tgacagagaa gggtgggcca gggagagacg gataagtgat   4380
ctaactcctg aggaggtggc ctggccagga gctagagcat gaggatctcg taggatttta   4440
ttctgcaagg tgaaaagcca ttgtattagt ctgttcacaa accccagact aggcaattta   4500
caaaagaaag agaggtttaa tggacttaca gttccacatg gctggggagg cctcacaatc   4560
atggcgaaag gcaatgagga gcaagtcacg tcttacgtgg atggcaggca aagacaaaga   4620
cagcttgtgc agagaaactc cccctatag agccatcaga tcctgttaga cttatcacta    4680
tcacgagaac agcacgggta agacctgtcc ccatgattca gttacctccc actgggtccc   4740
tcccacaacg catgggaatt caggatgaga tttgggtggg gacacaacca aaccctatca   4800
ttccacccat ggcccctccc aaatttcatg tcctcacatt tcaaaaccaa tcacaccatc   4860
ccaacagtcc ctcaaagtct taaatgattt cagcattaac tcaaaagtcc acagtctaat   4920
gtctcatctg agacaaggca agtcctttcc gtctatgagc ctataaaatc caaagcaagt   4980
taattacttc ctagatacaa tgggggtaca ggcattgggt aaatacagcc attccaaatg   5040
ggataaattg gtcaaaacaa agaggctaca ggcccatgag agtccaaaat ccagtggggc   5100
agtcaaatct taaagctcca aaatgatctc ctcttgactc cacatctcac atccaggtca   5160
tgcagatgga aggggtgggt tcccatggtc ttgggcagct ctgcccctgt acctttgcag   5220
ggtacagcct ccctctcagc tgctttcatg ggctggcatt gagtgtctgc aacttttcca   5280
ggtacacggt gcaagctgtc ggtggatcta ccattctggg gtctggagga cctcttctca   5340
cagctccact aggtggtgcc ccagtaggga ctgtgtgtgg ggtctctgac cccacatttc   5400
ccttctgcac tgccctggca gaggatctcc atgagggccc tgcccctgca gcaaacttct   5460
gcctgggcat ccaggcattt ccgcacatcc tctttaatct aggcgaaggt ttccaaaccc   5520
cagttcttga cttctgtgca ctcgcagtct caacaccaca tggaagctgt caaggcttgg   5580
ggcttgcact ccccgaagct acagcccaag ctctaccttg cctcctgtca gtcatggttg   5640
ggagtggctg ggatgcaggg caccaagtcc ctaggctgca cacagcatga ggaccccggg   5700
cctggccaac aaaaccattt tttcctgata tctctggacc tgtgatggga ggggttgcca   5760
```

-continued

```
taaagacctc tgacatgccc tggagacatt ttccccattg tcttgggaat tagcatttgg   5820
ctcctgttac tcatgcaaat ttctgcagcc agcttgaatt tctcctcaga aaatgggaat   5880
ttttcttttc tatcacattg tcaggctgca aatttttccga acttttatgc tctgcttccc   5940
ttataaaact gaatgtcttt aacagcaccc aagtcacctc ttgaatgctt tgctgcttag   6000
aaatttctcc tgccagatac tctaaatcat ctctctgaag ttcaaagttc tacaaatatc   6060
tcgtgcaggg gcaaaatgcc gccagtatct ttgctaaaac ataacaagag tccccttttgc   6120
tccagttccc aacaagttcc tcatttccgt ctgagaccac ctcagcctat ggactttatt   6180
gtccacagtg ctatcagcat tttgggcaaa gccattcaac aagtctctag gaagttccaa   6240
actttcccac atttgcctgt cttcttctga gccctccaaa ctgttccaaa ccctgcctgt   6300
tacccagttc caaagtcaca tacccatttt tgagtatcta cggcagcacc ccactctact   6360
ggtaccaatt tagccactga agtagttgga gaacagaagt aatagactct ggtttacatt   6420
gtaaaagctt ctctgtggct gctgtgtgaa gaaaatatat gagaatgaag ccccaagatg   6480
aagcagggac acagttgcag tggttagagt aagaaatgct gctggctggc actgaagtga   6540
tagcctggag gtttgtgtgt gcacatgcat gtgtatgtgt tttacgatag taggcccaac   6600
agatactgta atccacactt gtttttttttt ttttttgag acagagtctc acctgttgcc   6660
tagactagaa tgcagtggca caatcttggc tcactacaac ctccacctcc caggttcaaa   6720
caatccttgt gcttcagcct cccgagtagt tgggattaca ggtgtgtgcc accgtgccca   6780
gctatatttt ttgtattttt agcagagatg ggattttgcc acattggcca ggctggtctt   6840
gaactcctgg cctcaagcaa tcctcccacc ttagcctccc aaagtgctga gccaccacac   6900
ctggccgcaa ctgattttta atcatgaaat gacacataca tttaaaaaac ccaataccta   6960
taatattcct ggctagtact cttcacatct atatcatcaa aaacaaagaa agtatgtgaa   7020
actgacacag ccaaggggag actaaggaga cataacaatt aactgtaatg tggtattctg   7080
gaggggatcc tggaacagaa aaagacatta ggcaaaaaac taaagaaatc tgaataaaat   7140
gtggatgtca gttaataata atgtatcata ttagtccagt aattgtaaca aatataccca   7200
ataatgaaag ccattaatta tagggaaaat ggaggggtta atatgggtgg ctggcttttg   7260
ctatttctag cagctccatt ttatctacaa aagacaaaca ttcattaagt cccaaaaagg   7320
taaagaatga caaattaagc atgtatctta ttagtaagag taatataaag atgctcactc   7380
atatttataa atatttgaca atgatgttaa ggccagaaaa gagaaaaaag ggtaggggca   7440
aaaaacgcaa agagaaagga gttagtatct tttctcccgc actcattagc tattaaaaga   7500
ggatgtttgt ttaaagctgc tcagagctgg taaactaatg ttaagtcact aacgggaatt   7560
taaaaggttt cattaagaac tgcctgcact agattcctcc accctgagac attaaacaat   7620
cacgataaac ctcctgagtg gtaagaacgt gtccatttaa aaacaggcta tagattgtca   7680
tgcagtttta tctactaatc ggctaatgca ccgccaaaaa caaacaaaaa aacccaaagg   7740
gatgaaagtt tcatccatca aaggaaacaa cagtcacctt ggttcccatc ccactcatat   7800
actgccgccg tacatgtcaa tcagatgaac ctgtgcgtat ctcttaatga caattgaccc   7860
accttttttaa ctgaagtgaa ggggggttct gctccgcgac cacttcctgg atctctccct   7920
tcaccctctg tgttctttcg ggtgcaccat cgggtcaaag ccgcagcaac gccgtctctg   7980
tgtgatcgca tgtgcccttc tgcacacgac cttcccccga gagtgaccag ctaccggaca   8040
ggcaccaagg agggctaccg agcacctccc ggaccggcgg ctgcaggatc gcgagcgcct   8100
```

```
ccgctaggga gaccgcacgt tgcgcctgtg cttcctgcgg tggcgccttc tgcaaggaga   8160

cctcgaccct gctccctctc cggggctgga tctgactcct tgacggtgat tccagacgcg   8220

agacccaaac tgacggcttc tagaagaggg gcgagcccgg ccgcaagtct ttcacgtagc   8280

taagtcatcg ttgcttccgg cttcttaccg ttctcccctt tgtaaacggt tacctcccga   8340

aaacccaggc tctcctccaa cagtggttct caagcgaggc gatcttcccc gggaggggat   8400

atttggcaaa gtctgggggc atttttggtt cactggggct gctacttgca tccactgggt   8460

agaggcgggg gatgcagcta cacaacctgc gaagcacggg acagcaccct ccccaaccca   8520

gacagaatta gccggcccaa aacctcagta gtgcccaggc tgagaaaccc tgccttaaac   8580

aaacaacaaa gaaaggccaa gtcccataag tgggtcaccg cgccgagact ggggtccacg   8640

ggacacccca gccacgccaa gccgggaagt ccccgcctcc tggagctgaa cccgcccctc   8700

tcccagaggt ggagctgcgg ggggcgggaa caggcacgga gaaaataaac aagactaaaa   8760

agtcctgagt agcgctgtgt ggccgcaaac ctgaacccac cttttgcacc acgcgggacc   8820

cggcactctt cctgccaccc accccctgaga gggctgcgcg gccgacccca gtactagaaa  8880

acactcgtca cctcactcaa gacgggtacg aaggccaacg gacgccttcc tttagaacgc   8940

tcagcacaca gagcaacttc tcacgcctac tctcaaatgg cgtactccaa actagcactc   9000

ccgacgtcca gctgtgaacc cagagcggcg gaaagcccct gaacccagcg cccgggcatg   9060

cgcagacgcg ttgttgtggt gggcgtggct ccctccggac ccggcgcccc gccctccgcc   9120

ccgtgtccgc atgcgcgact gagccgggtg gatggtactg ctgcatccgg gtgtctggag   9180

gctgtggccg ttttgtttc ttggctaaaa tcgggggagt gaggcgggcc ggcgcggc     9238
```

<210> SEQ ID NO 21
<211> LENGTH: 1249
<212> TYPE: DNA
<213> ORGANISM: Homo sapiens

<400> SEQUENCE: 21

```
ctgatctaca taggaattgt tttcaagaca tttctgcatt cctctagtga cagggtgctc     60

actacctcat gagtatttca gtggacaact gtaatggtca ataaagtatc cactttccac    120

ctccctgcag ctcctggccc tggctttatt ctctggggct ccacacattc agtttacact    180

cagtggccag tggctgggac cattgtagaa aataaggaaa ctccaattcc ttccttcttt    240

tcttcctctt tcatctcttc ctccctctct acatccctct ctctcttcct tccttcctcg    300

acacttacca tgtaccagac cttctgccag gcacatggat gggagcacag gggaagttgg    360

ctgcagggtt agaactaagt cccaagcccc ctaaagctca tgccagggga ctggactgtc    420

cagtactgag ggatggggat gctgaggctg gtggccttcc tcaaatgcac tgtagtgccc    480

caggcagagt cctgggctgc cctgtgagga ggtgaccaga ggtagagcaa cttcacccta    540

aggctggatc aggatcccct ccaggttttt actagagcca aacccacatc tcctttctct    600

tctgccaccc ccccttaaaa tgcttagaaa cacatagatt taaatacaaa ttcaaatgta    660

agtaatttca actgtgtaac tatgaggagt cagttctacg tgggtcctat ctgtatcctc    720

cccagggctc agctccattc tttgctttca ttcattctca ttcaatacat tgttgttaag    780

agctcactgg gtgccctctc tgtcatgtag taaggtttta aaaagaaagc ctcttctgag    840

cttcagtttc cttattcata aaataggagt attgatccgt tccttgcttt tcttacaagg    900

atatgctgaa gatgactgaa gtacagagta aagaaggatt atgtttgggt gtcaaaggaa    960

tagaatgccc tctttcaaac tgagcacagc aggaacctgt aacaggaaca cagcaacttg   1020
```

```
ttgaatgaat gacaatattg gaaaacatac atttcctccc ctccccatca tagtccctct   1080

gcttccgtgt taactccata gagaggccag cacaaccagc cttgcagcct gagataaggc   1140

ctttggcggg tgtctcccct atcgctccct caagccctca agtaggtgtt ggagagaggg   1200

gtgatgcctg gtgctggtgg aacccctgca cagagacgga cacaggatg               1249
```

<210> SEQ ID NO 22
<211> LENGTH: 699
<212> TYPE: DNA
<213> ORGANISM: Homo sapiens

<400> SEQUENCE: 22

```
ctagagaggg aagtttttga aaattaaaca ctgtctaatt ttctgcaaag tttttattca     60

tgaattaaga gtatttccct tagtccatta ttcccaaggc aaatatggaa gtttgatcat    120

atgctaatca tactaaagct ggattctctt taagagattg agaaattaaa aggcaaaagc    180

tgatatatca tgtttagtta tactgtgagt cttataagaa gctgggaggc aaccccatta    240

actcaccaga atacagaact cagtctcaca acttaaatat aattcctctc aaaccttttc    300

ctcaaagtta aattctgaaa ataatcttgt gattaagaga agaaggctgt ccaccaatgg    360

acttatctgt tatttcttcc ttattgtgag cttaatggca tgacaaagca gaggcaaaga    420

ggcatacatc aattcttcaa agtaggaagt caaaaaggtc agagcttcca cagcatggca    480

acagctttgc agatgcccac atcgtgatag ttgaaatagc aaagcccagc aaaggttaaa    540

gctgaaaatg ccaaaagccc tgccttggca gctttctgcg aggcatcccc atgaacatag    600

tcagtaacaa cttgtccaag gccccagtga ccatgaagag tgagggctgc agccagggaa    660

tagtccgtcg cagagcaagg attcaaataa gcagccgga                           699
```

<210> SEQ ID NO 23
<211> LENGTH: 699
<212> TYPE: DNA
<213> ORGANISM: Homo sapiens

<400> SEQUENCE: 23

```
ctagagaggg aagtttttga aaattaaaca ctgtctaatt ttctgcaaag tttttattca     60

tgaattaaga gtatttccct ttgtccatta ttcccaaggc aaatatggaa atttgatcat    120

gtactaatca tactaaagct ggattctctt taagagattg agaaattaaa aggcaaaagc    180

tgatatgtca tgtttagtta tattgtgagt cttataagaa gctgggaggc aaccccatta    240

actcaccaga atacagaact cagtctcaca acttaaatat aattcctctc aaaccttttc    300

ctcaaagtta aattctgaaa ataatcttgt gattaagaga agaaggctgt ccaccaatgg    360

acttatctgt tatttcttcc ttattgtgag cttaatggca tgacaaagca gaggcaaaga    420

ggcatacatc aattcttcaa agtaggaagt caaaaaggtc agagcttcca cagcatggca    480

acagctttgc agatgcccac atcgtgatag ttgaaatagc aaagcccagc aaaggttaaa    540

gctgaaaatg ccaaaagccc tgccttggca gctttctgcg aggcatcccc atgaacatag    600

tcagtaacaa cttgtccaag gccccagtga ccatgaagag tgagggctgc agccagggaa    660

tagtccgtcg cagagcaagg attcaaataa gcagccgga                           699
```

<210> SEQ ID NO 24
<211> LENGTH: 699
<212> TYPE: DNA
<213> ORGANISM: Homo sapiens

<400> SEQUENCE: 24

```
ctagagaggg aagtttttga aaattaaaca ctgtctaatt ttctgcaaag tttttattca     60

tgaattaaga gtatttccct ttgtccatta ttcccaaggc aaatatggaa atttgatcat    120

gtactaatca taataaagct ggattctctt taagagattg agaaattaaa aggcaaaagc    180

tgatatatca tgtttagtta tattgtgagt cttataagaa gctgggaggc aaccccatta    240

actcaccaga atacagaact cagtctcaca acttagatat aattcctctc aaaccttttc    300

ctcaaagatt aaattctgaa aataatcttg tgattaagag aagaaggctg tccaccaatg    360

ggcttatctg ttatttcttc cttattgtga gcttaatggc atgacaaagc agaggcaaag    420

aggcatacat caattcttca aagtaggaag tcaaaaaggt cagagcttcc acagcatggc    480

aacagctttg cagatgccca catcgtgata gttgaaatag caaagcccag caaaggttaa    540

agctgaaaat gccaaaagcc ctgccttggc agctttctgc gaggcatccc catgaacata    600

atcagtaaca acttgttcaa ggccccagtg accatgaaga gtgagggctg cagccgggaa    660

tagtccgtcg cagagcaagg attcaaataa gcagccgga                           699
```

<210> SEQ ID NO 25
<211> LENGTH: 994
<212> TYPE: DNA
<213> ORGANISM: Homo sapiens

<400> SEQUENCE: 25

```
ttgtatctct ttttacagct acctcccatt tcccttctat ttcaagctag taacacagtt     60

ttcttttaaa ttcatttatt taaatgtaaa aataagtcta tttggagaaa aaaaattttt    120

aatagcatct ctggaatgcc agtatggcta aattcatgaa tgttgtcctc aaatgctgaa    180

atctgggaag catctggcca agctttgtgg acaggcctgc ctagtttgaa tcccaagagc    240

cactcattcc gagccacaaa acattggaat tcttggttca cttccctaac ctgaacttgt    300

cctctgtgaa atagggacat taatagctca ctcacagggc tgctgtgagg acatgtgttg    360

agctgagggt ctcgccaggg gagaccctgt gcagggagac tgttatcatg gtgatggatt    420

tctgcttcat tcatttcttt ttccagacag catcatatag aatgagttgt ggggtggcag    480

tcagcaggtt tgggtttatc ctctattctg ccacttatta cttaaaaaaa aaaacccaac    540

ttatatagta taagctatat ccagaaaagt gcaaatatca tacaagtacc atttgatgaa    600

tcttctgata tccccacata accaacaccc agaacctctt cttgtctcat tccaggataa    660

ccactaacct gacttctaac agcatcagtc agttttgtct gtttttgtac attatatatg    720

tgatggtttg aatgtgtccc ccaaatttca tgtgctagaa acttaatcct tcaattcata    780

tgttgatgct atttggagga agggcctttg ggaagtaatt aggattagat aaggtcatgg    840

ggtgaggtat gatggcactg gtgacttata agaagagaaa gagaaatctg agctggcatg    900

ctcttgccct ctcaccgtgt gatgacttct ccatgtcatg atgcagcaag aaggccctca    960

ccagatggtg gcaccatgct tttggacttc ccag                                994
```

<210> SEQ ID NO 26
<211> LENGTH: 1000
<212> TYPE: DNA
<213> ORGANISM: Homo sapiens

<400> SEQUENCE: 26

```
ttgtatctct ttttacagct acctcccatt tcccttctat ttcaagctag taacacagtt     60

ttcttttaaa ttcatttatt taaatgtaaa aataagtcta tttggagaaa aaaaattttt    120
```

```
aatagcatct ctggaaggcc agtatggcta aattcatgaa tgttgtcctc aaatgctgaa    180

atctgggaag catctggcca agctttgtgg acaggcctgc ctagtttgaa tcccaagagc    240

cactcattcc gagccacaaa acattggaat tcttggttca cttccctaac ctgaacttgc    300

cctctgtgaa atagggacat taatagctca ctcacagggc tgctgtgagg acatgtgttg    360

agctgagggt ctggtcaggg gagaccctgt gcagggagac tgttatcatg gtgatggatt    420

tctgcttcat tcatttcttt ttccagacag catcatatag aatgagttgt ggggtggcag    480

tcagcaggtt tgggtttatc ctctattctg ccacttatta cttaaaaaaa ccccaaaaaa    540

cccaacttat atagtataag ctatatccag aaaagtgcaa atatcataca agtaccattt    600

gatgaatctt ctgatatccc cacataacca acacccagaa cctcttcttg tctcattcca    660

ggataaccac taacctgact tctaacagca tcagtcagtt ttgtctgttt ttgtacatta    720

tatatgtgat ggtttgaatg tgtcccccaa atttcatgtg ctggaaactt aatccttcaa    780

ttcatatgtt gatgctattt ggaggaaggg cctttgggaa gtaattagga ttagataagg    840

tcatggggtg aggtatgatg gcactggtga cttataagaa gagaaagaga aatctgagct    900

ggcatgctct tgccctctca ctgtgtgatg acttctccat gtcatgatgc agcaagaagg    960

ccctcaccag atggtggcac catgcttttg gacttcccag                          1000
```

<210> SEQ ID NO 27
<211> LENGTH: 999
<212> TYPE: DNA
<213> ORGANISM: Homo sapiens

<400> SEQUENCE: 27

```
ttgtatctct ttttacagct acctcccatt tcccttctat ttcaagctag taactcagtt     60

ttcttttaaa ttcaattatt taaatgtaaa aataagtcta tttggagaaa aaaaatttta    120

atagcatctc tggaatgcca gtatggctaa attcatgaat gttgtcctca aatgctgaaa    180

tctgggaagc atctggccaa gctttgtgga caggcctgcc tagtttgaat cccaagagcc    240

acccagtcca agccacaaaa cattggaatt cttggttcac ttccctaacc tgaacttgcc    300

ctctgtgaaa tagggacact aatagctcac tcacagggct gctgtgagga catgtgttga    360

gctgagggtc tcgccagggg agaccctgtg cagggagact gttatcatgg tgatggattt    420

ctgcttcatt catttctttt tccagacagc atcatataga atgagttgtg gggtggcagt    480

cagcaggttt gggtttatcc tctattctgc cacttattac ttaaaaaaac cccaaaaaac    540

ccaacttata tagtataagc tatatccaga aaagtgcaaa tatcatacaa gtaccatttg    600

atgaatcttc tgatatcccc acataaccaa cacccagaac ctcttcttgt ctcattccag    660

gataaccact aacctgactt ctaacagcat cagtcagttt tgtctgtttt tgtacattat    720

atatgtgatg gtttgaatgt gtcccccaaa tttcatgtgc tggaaactta atccttcaat    780

tcatatgttg atggtttttg gaggaagggc ctttgggaag taattaggat tagataaggt    840

catggggtga ggtatgatgg cactggtgac ttataagaag agaaagagaa atctgagctg    900

gcatgctctt gccctctcac tgtgtgatga cttctccatg tcatgatgca gcaagaaggc    960

cctcaccaga tggtggcacc atgcttttgg acttcccag                           999
```

<210> SEQ ID NO 28
<211> LENGTH: 25
<212> TYPE: DNA
<213> ORGANISM: Artificial Sequence
<220> FEATURE:

```
<223> OTHER INFORMATION: Description of Artificial Sequence: Artificial
      primer

<400> SEQUENCE: 28

ggctaaatat tttgatgacc aagtt                                            25


<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Artificial
      primer

<400> SEQUENCE: 29

gcagccaact tcccctgtg                                                   19


<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Artificial
      primer

<400> SEQUENCE: 30

gctctacctt ggtcacctcc                                                  20


<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Artificial
      primer

<400> SEQUENCE: 31

aggtcacatc catttatccc actg                                             24


<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Artificial
      primer

<400> SEQUENCE: 32

agaagatggg ggaatctttt tcct                                             24


<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Artificial
      primer

<400> SEQUENCE: 33

ttgtgactgg gctagaaaga aggtg                                            25


<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Artificial
```

primer

<400> SEQUENCE: 34
tgttgcctgc atttgtacgt gag 23

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Artificial primer

<400> SEQUENCE: 35
ttctgtctgg gttggggagg g 21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Artificial primer

<400> SEQUENCE: 36
ggaggggtta atatgggtgg c 21

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Artificial primer

<400> SEQUENCE: 37
tttgtcctgg ttgcctgtgg tc 22

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Artificial primer

<400> SEQUENCE: 38
caaatcctgt tgactggtct cgg 23

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Artificial primer

<400> SEQUENCE: 39
aacggctcca tcacccctaa ag 22

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Artificial primer

<400> SEQUENCE: 40
cccactccta gataccaacc caag 24

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Artificial primer

<400> SEQUENCE: 41
ctttatgcac tgcctcgttg aatc 24

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Artificial primer

<400> SEQUENCE: 42
ttgactggtg tggttgctgt tg 22

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Artificial primer

<400> SEQUENCE: 43
gcagaaaggg gagttgatgc tg 22

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Artificial primer

<400> SEQUENCE: 44
ctgacaaagt tgagagccca ctg 23

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Artificial primer

<400> SEQUENCE: 45
ttaagcctac atccacatgc tgag 24

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Artificial primer

<400> SEQUENCE: 46
ccttggtctg ccagaatttt ca 22

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Artificial primer

<400> SEQUENCE: 47
gtttggcatc ataggagatt tggc 24

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Artificial primer

<400> SEQUENCE: 48
cctgtcccca tgattcagtt acc 23

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence: Artificial primer

<400> SEQUENCE: 49
acgtacaaat gcaggcaac 19

<210> SEQ ID NO 50
<211> LENGTH: 27
<212> TYPE: DNA
<213> ORGANISM: Artificial Sequence
<220> FEATURE:
<223> OTHER INFORMATION: Description of Artificial Sequence: Artificial primer

<400> SEQUENCE: 50 ccttttttg tttgtttttg gcggtgc 27

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Artificial primer

<400> SEQUENCE: 51
agcttactgg atgaccacca 20

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Artificial primer

<400> SEQUENCE: 52
gactgggggg aaaagcgcaa tac 23

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Artificial primer

<400> SEQUENCE: 53
gtattgcgct tttcccccca gtc 23

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: Artificial primer

<400> SEQUENCE: 54
tgacttgctc tcatcccaca tg 22

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Artificial primer

<400> SEQUENCE: 55
gggcttgaag caagtaaatg gaag 24

<210> SEQ ID NO 56
<211> LENGTH: 29
<212> TYPE: DNA
<213> ORGANISM: Artificial Sequence
<220> FEATURE:
<223> OTHER INFORMATION: Description of Artificial Sequence: Artificial primer

<400> SEQUENCE: 56
gctatcaata ttttcttggt tacagacac 29

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence: Artificial primer

<400> SEQUENCE: 57
gttcactgcc ataagtcttc agtgc 25

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Artificial primer

<400> SEQUENCE: 58
tggccgcact gaagacttat gg 22

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: Artificial primer

<400> SEQUENCE: 59
cagctgcatc tatgataatc cacc 24

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Artificial primer

<400> SEQUENCE: 60
atggacaagt ccgaggtgat ag 22

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Artificial primer

<400> SEQUENCE: 61
atcacctcgg acttgtccat tc 22

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence: Artificial primer

<400> SEQUENCE: 62
gcaatcagag atccaaaggc caac 24

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: Artificial primer

<400> SEQUENCE: 63
gttggccttt ggatctctga ttgc 24

<210> SEQ ID NO 64
<211> LENGTH: 26
<212> TYPE: DNA
<213> ORGANISM: Artificial Sequence
<220> FEATURE:
<223> OTHER INFORMATION: Description of Artificial Sequence: Artificial primer

<400> SEQUENCE: 64
gacatagtat accctggaat tgctgt 26

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence: Artificial primer

<400> SEQUENCE: 65
acagcaattc cagggtatac tatgtc 26

<210> SEQ ID NO 66
<211> LENGTH: 22
<212> TYPE: DNA
<213> ORGANISM: Artificial Sequence
<220> FEATURE:
<223> OTHER INFORMATION: Description of Artificial Sequence: Artificial primer

<400> SEQUENCE: 66
ctcccccgat tttagccaag aa 22

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Artificial primer

<400> SEQUENCE: 67
gttgtaaccg agtgctgggg attc 24

<210> SEQ ID NO 68
<211> LENGTH: 19
<212> TYPE: DNA
<213> ORGANISM: Artificial Sequence
<220> FEATURE:
<223> OTHER INFORMATION: Description of Artificial Sequence: Artificial primer

<400> SEQUENCE: 68
tgccggctcc gacggtatc 19

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence: Artificial primer

<400> SEQUENCE: 69
tcctgaacct gctctgtgaa gtgc 24

<210> SEQ ID NO 70
<211> LENGTH: 24
<212> TYPE: DNA
<213> ORGANISM: Artificial Sequence
<220> FEATURE:
<223> OTHER INFORMATION: Description of Artificial Sequence: Artificial primer

<400> SEQUENCE: 70
cgatacccag tttgtctgcc atgc 24

```
<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence: Artificial
      primer

<400> SEQUENCE: 71

agacagacta ccacatgaac ttac                                        24


<210> SEQ ID NO 72
<211> LENGTH: 25
<212> TYPE: DNA
<213> ORGANISM: Artificial Sequence
<220> FEATURE:
<223> OTHER INFORMATION: Description of Artificial Sequence: Artificial
      primer

<400> SEQUENCE: 72

tctgatcttt atcctccgtt ccctc                                       25


<210> SEQ ID NO 73
<211> LENGTH: 18
<212> TYPE: DNA
<213> ORGANISM: Artificial Sequence
<220> FEATURE:
<223> OTHER INFORMATION: Description of Artificial Sequence: Artificial
      primer

<400> SEQUENCE: 73

cgctgcctgc cctctga                                                18


<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Artificial
      primer

<400> SEQUENCE: 74

ctggaggctc tgagaggttg ag                                          22


<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Artificial
      primer

<400> SEQUENCE: 75

aagctgagtt ccccaatgct gagg                                        24


<210> SEQ ID NO 76
<211> LENGTH: 22
<212> TYPE: DNA
<213> ORGANISM: Artificial Sequence
<220> FEATURE:
<223> OTHER INFORMATION: Description of Artificial Sequence: Artificial
      primer

<400> SEQUENCE: 76

cactgcactt ggcaccattg ag                                          22
```

```
<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Artificial
      primer

<400> SEQUENCE: 77

ttccgaaggc tgcttttccc                                                20


<210> SEQ ID NO 78
<211> LENGTH: 26
<212> TYPE: DNA
<213> ORGANISM: Artificial Sequence
<220> FEATURE:
<223> OTHER INFORMATION: Description of Artificial Sequence: Artificial
      primer

<400> SEQUENCE: 78

gatattactg atgaccatcc tcatgg                                         26


<210> SEQ ID NO 79
<211> LENGTH: 22
<212> TYPE: DNA
<213> ORGANISM: Artificial Sequence
<220> FEATURE:
<223> OTHER INFORMATION: Description of Artificial Sequence: Artificial
      primer

<400> SEQUENCE: 79

ttgtggatgt tctggccaag tg                                             22


<210> SEQ ID NO 80
<211> LENGTH: 23
<212> TYPE: DNA
<213> ORGANISM: Artificial Sequence
<220> FEATURE:
<223> OTHER INFORMATION: Description of Artificial Sequence: Artificial
      primer

<400> SEQUENCE: 80

gctgtcacca ctctgactgc tac                                            23


<210> SEQ ID NO 81
<211> LENGTH: 25
<212> TYPE: DNA
<213> ORGANISM: Artificial Sequence
<220> FEATURE:
<223> OTHER INFORMATION: Description of Artificial Sequence: Artificial
      primer

<400> SEQUENCE: 81

aaggtcaact tggcgcagtt ggtgg                                          25


<210> SEQ ID NO 82
<211> LENGTH: 24
<212> TYPE: DNA
<213> ORGANISM: Artificial Sequence
<220> FEATURE:
<223> OTHER INFORMATION: Description of Artificial Sequence: Artificial
      primer

<400> SEQUENCE: 82

gtgagactga gttctgtatt ctgg                                           24


<210> SEQ ID NO 83
```

<211> LENGTH: 24
<212> TYPE: DNA
<213> ORGANISM: Artificial Sequence
<220> FEATURE:
<223> OTHER INFORMATION: Description of Artificial Sequence: Artificial primer

<400> SEQUENCE: 83
ccagaataca gaactcagtc tcac 24

<210> SEQ ID NO 84
<211> LENGTH: 24
<212> TYPE: DNA
<213> ORGANISM: Artificial Sequence
<220> FEATURE:
<223> OTHER INFORMATION: Description of Artificial Sequence: Artificial primer

<400> SEQUENCE: 84
ggcagacaaa ctgggtatcg ttgc 24

<210> SEQ ID NO 85
<211> LENGTH: 24
<212> TYPE: DNA
<213> ORGANISM: Artificial Sequence
<220> FEATURE:
<223> OTHER INFORMATION: Description of Artificial Sequence: Artificial primer

<400> SEQUENCE: 85
gggttaaagt cacatacaca gatg 24

<210> SEQ ID NO 86
<211> LENGTH: 26
<212> TYPE: DNA
<213> ORGANISM: Artificial Sequence
<220> FEATURE:
<223> OTHER INFORMATION: Description of Artificial Sequence: Artificial primer

<400> SEQUENCE: 86
atacagaact cagtctcaca acttag 26

<210> SEQ ID NO 87
<211> LENGTH: 22
<212> TYPE: DNA
<213> ORGANISM: Artificial Sequence
<220> FEATURE:
<223> OTHER INFORMATION: Description of Artificial Sequence: Artificial primer

<400> SEQUENCE: 87
gtgttgtaac cgagtgctgg gg 22

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Artificial primer

<400> SEQUENCE: 88
tctccacagc tccatcatgg g 21

<210> SEQ ID NO 89
<211> LENGTH: 23

<212> TYPE: DNA
<213> ORGANISM: Artificial Sequence
<220> FEATURE:
<223> OTHER INFORMATION: Description of Artificial Sequence: Artificial primer

<400> SEQUENCE: 89
ggctgtaaaa atggctgaag cag 23

<210> SEQ ID NO 90
<211> LENGTH: 22
<212> TYPE: DNA
<213> ORGANISM: Artificial Sequence
<220> FEATURE:
<223> OTHER INFORMATION: Description of Artificial Sequence: Artificial primer

<400> SEQUENCE: 90
gcatgacgtg ttctgcctct tg 22

<210> SEQ ID NO 91
<211> LENGTH: 23
<212> TYPE: DNA
<213> ORGANISM: Artificial Sequence
<220> FEATURE:
<223> OTHER INFORMATION: Description of Artificial Sequence: Artificial primer

<400> SEQUENCE: 91
ctatcagcat tctgatctca acg 23

<210> SEQ ID NO 92
<211> LENGTH: 27
<212> TYPE: DNA
<213> ORGANISM: Artificial Sequence
<220> FEATURE:
<223> OTHER INFORMATION: Description of Artificial Sequence: Artificial primer

<400> SEQUENCE: 92
gaatagcaga gaaaacctca gactgcc 27

<210> SEQ ID NO 93
<211> LENGTH: 23
<212> TYPE: DNA
<213> ORGANISM: Artificial Sequence
<220> FEATURE:
<223> OTHER INFORMATION: Description of Artificial Sequence: Artificial primer

<400> SEQUENCE: 93
gctccattct tgacaataca ggc 23

<210> SEQ ID NO 94
<211> LENGTH: 29
<212> TYPE: DNA
<213> ORGANISM: Artificial Sequence
<220> FEATURE:
<223> OTHER INFORMATION: Description of Artificial Sequence: Artificial primer

<400> SEQUENCE: 94
gcttatacta tataagttgg gttttttgg 29

<210> SEQ ID NO 95
<211> LENGTH: 24
<212> TYPE: DNA

<213> ORGANISM: Artificial Sequence
<220> FEATURE:
<223> OTHER INFORMATION: Description of Artificial Sequence: Artificial primer

<400> SEQUENCE: 95
gtttgaatcc caagagccac tcat 24

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Artificial primer

<400> SEQUENCE: 96
tccactttcc acctccctgc 20

<210> SEQ ID NO 97
<211> LENGTH: 23
<212> TYPE: DNA
<213> ORGANISM: Artificial Sequence
<220> FEATURE:
<223> OTHER INFORMATION: Description of Artificial Sequence: Artificial primer

<400> SEQUENCE: 97
ttgtcggtgc tgatctcagt gga 23

<210> SEQ ID NO 98
<211> LENGTH: 18
<212> TYPE: DNA
<213> ORGANISM: Artificial Sequence
<220> FEATURE:
<223> OTHER INFORMATION: Description of Artificial Sequence: Artificial primer

<400> SEQUENCE: 98
aggtccctcc tccagcac 18

<210> SEQ ID NO 99
<211> LENGTH: 25
<212> TYPE: DNA
<213> ORGANISM: Artificial Sequence
<220> FEATURE:
<223> OTHER INFORMATION: Description of Artificial Sequence: Artificial primer

<400> SEQUENCE: 99
acatgatgca catctacgtg ttcgc 25

<210> SEQ ID NO 100
<211> LENGTH: 24
<212> TYPE: DNA
<213> ORGANISM: Artificial Sequence
<220> FEATURE:
<223> OTHER INFORMATION: Description of Artificial Sequence: Artificial primer

<400> SEQUENCE: 100
cagacaaact gggtatcgtt gctg 24

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence: Artificial primer

<400> SEQUENCE: 101
cgatacccag tttgtctgcc atgc 24

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Artificial primer

<400> SEQUENCE: 102
agacctttgg agcaggagtg 20

<210> SEQ ID NO 103
<211> LENGTH: 23
<212> TYPE: DNA
<213> ORGANISM: Artificial Sequence
<220> FEATURE:
<223> OTHER INFORMATION: Description of Artificial Sequence: Artificial primer

<400> SEQUENCE: 103
ctgctcacct tgctgatctt ccc 23

<210> SEQ ID NO 104
<211> LENGTH: 23
<212> TYPE: DNA
<213> ORGANISM: Artificial Sequence
<220> FEATURE:
<223> OTHER INFORMATION: Description of Artificial Sequence: Artificial primer

<400> SEQUENCE: 104
ttatgtgcac agtgcggtgt tgg 23

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Artificial primer

<400> SEQUENCE: 105
caggtacttg gctcccccga c 21

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Artificial primer

<400> SEQUENCE: 106
aggggtgggt agggaatatg 20

<210> SEQ ID NO 107
<211> LENGTH: 24
<212> TYPE: DNA
<213> ORGANISM: Artificial Sequence
<220> FEATURE:

<223> OTHER INFORMATION: Description of Artificial Sequence: Artificial primer

<400> SEQUENCE: 107
acccagcaag ctgaagttgt agcc 24

<210> SEQ ID NO 108
<211> LENGTH: 25
<212> TYPE: DNA
<213> ORGANISM: Artificial Sequence
<220> FEATURE:
<223> OTHER INFORMATION: Description of Artificial Sequence: Artificial primer

<400> SEQUENCE: 108
ccaggttgtt aagcattgct gtacc 25

<210> SEQ ID NO 109
<211> LENGTH: 22
<212> TYPE: DNA
<213> ORGANISM: Artificial Sequence
<220> FEATURE:
<223> OTHER INFORMATION: Description of Artificial Sequence: Artificial primer

<400> SEQUENCE: 109
gcatgacgtg ttctgcctct tg 22

<210> SEQ ID NO 110
<211> LENGTH: 23
<212> TYPE: DNA
<213> ORGANISM: Artificial Sequence
<220> FEATURE:
<223> OTHER INFORMATION: Description of Artificial Sequence: Artificial primer

<400> SEQUENCE: 110
gagattaaaa atcctgtgct cca 23

<210> SEQ ID NO 111
<211> LENGTH: 24
<212> TYPE: DNA
<213> ORGANISM: Artificial Sequence
<220> FEATURE:
<223> OTHER INFORMATION: Description of Artificial Sequence: Artificial primer

<400> SEQUENCE: 111
cttggtcatc aaaatattta gcct 24

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Artificial primer

<400> SEQUENCE: 112
agcttactgg atgaccacca 20

<210> SEQ ID NO 113
<211> LENGTH: 27
<212> TYPE: DNA
<213> ORGANISM: Artificial Sequence
<220> FEATURE:
<223> OTHER INFORMATION: Description of Artificial Sequence: Artificial -continued

```
      primer

<400> SEQUENCE: 113

agcacagttc cgggaagttg gctgcag                                        27


<210> SEQ ID NO 114
<211> LENGTH: 23
<212> TYPE: DNA
<213> ORGANISM: Artificial Sequence
<220> FEATURE:
<223> OTHER INFORMATION: Description of Artificial Sequence: Artificial
      primer

<400> SEQUENCE: 114

agcacagggg aagttggctg cag                                            23
```

MOLECULAR STRUCTURE OF RHD NEGATIVE

The present invention relates to a nucleic acid molecular structure representing the Rhesus genes locus comprising the RHD, SMP1 and RHCE genes and/or the Rhesus box(es), preferably the hybrid Rhesus box, the upstream Rhesus box and/or the downstream Rhesus box. Furthermore, the invention relates to a process for the specific detection of the common RHD negative haplotypes. The invention further relates to the detection of RHD positive haplotypes in D-negative individuals. Various mutations in the RHD gene have been identified that allow for the development of diagnostic tools. The invention also relates to oligonucleotides, that specifically hybridize to the hybrid box, preferably the breakpoint or breakpoint region or to the upstream and downstream Rhesus boxes. Additionally, the invention relates to kits comprising or employing the above recited compounds of the invention.

Several documents are cited throughout the text of this specification; the disclosure content of each of the documents cited herein (including any manufacturer's specifications, instructions, etc.) is hereby incorporated by reference.

The Rhesus D antigen (ISBT 004.001; RH1) is the most important blood group antigen determined by a protein. Anti-D remains the leading cause of hemolytic disease of the newborn (Filbey, Acta Obstet Gynecol Scand, 74:687, 1995; Bowman, J, Semin Perinatol 21:39, 1997). Depending on the population, 3% to 25% of whites lack the antigen D (Mourant, The distribution of the human blood groups and other polymorphisms, London, Oxford University Press, 1976). Anti-D immunizations can occur readily in D-negative recipients (Urbaniak, Transfusion 21:64, 1981).

The antigens of the RH blood group are carried by proteins coded by two genes, RHD and RHCE, that are located at chromosomal position 1p34.1-1p36 (Cherif-Zahar, Hum. Genet. 86: 398, 1991; MacGeoch, Cytogenet. Cell Genet. 59:261, 1992) probably within less than a 450,000 base pair (bp) distance (Carritt, Hum. Mol. Genet. 6:843, 1997). Both genes encompass ten exons and their structures are highly homologous. The relative orientation of the genes, their distance, and the possibility of interspersed other genes were unknown (Flegel, Transfus. Med. 8:281, 1998). Very recently, Okuda et al. (Okuda, Biochem. Biophys. Res. Commun. 263: 378, 1999) reported a sequence of about 11,000 bp, which was thought to represent the DNA segment between RHD and RHCE.

In whites, the vast majority of D-negative haplotypes is due to a deletion of the RHD gene: This deletion spans the whole RHD gene, because RHD-specific sequences ranging from exon 1 to the 3' untranslated region are absent (Gassner, Transfusion 37:1020, 1997). The exact extent of the deletion was uncertain, leaving open the possibility that neighboring genes were also affected.

The identification of the RHD gene as the molecular basis of the D antigen allowed RhD phenotype prediction by DNA typing (Flegel, Transfus. Med. 8:281, 1998; Lo, Lancet 341: 1147, 1993). However, since the structure of the prevalent D-negative haplotype is unknown, a specific detection of the RHD deletion remained impossible and the discrimination of $RHD^{+}/RHD^{+}$ homozygous from $RHD^{+}/RHD^{-}$ heterozygous individuals relied on indirect methods. This discrimination is of clinical interest in particular, because in D-negative mothers with an anti-D, the risk of an affected child is 100% with a $RHD^{+}/RHD^{+}$ father, but only 50% with a $RHD^{+}/RHD^{-}$ father.

Several indirect approaches have been applied to determine the zygosity: (i) a simple guess based on the phenotype is correct in about 95% of cases, (ii) determination of the D antigen density which can be confounded by factors such as the presence of the C antigen, and (iii) several methods involving the parallel quantitative amplification of RHD- and RHCE-specific sequences (Cossu, Electrophoresis 17:1911, 1996; Doscher, Infusionsther. Transfusionsmed. 26(suppl 1):31, 1999 (abstr.)). These elaborate techniques may not be practical in routine laboratories. In addition, several investigators identified polymorphisms in the RHCE gene or neighboring sequences genetically linked to the lack of the RHD gene (Carritt, Hum. Mol. Genet. 6:843, 1997; Huang, Am. J. Hum. genet. 58: 133, 1996; Fujiwara, Hum. genet. 104:301, 1999; Onda, Gene 159:225, 1995). This indirect approach relied on the linkage disequilibrium associating the RHD deletion with a polymorphism.

Furthermore, the utility of the RHD PCR is limited by the incomplete knowledge of presumably rare RHD positive alleles in RhD-negative. RHD positive alleles in RhD negative are caused by RHD-CE-D hybrid genes (Huang, Blood 88:2326-33, 1996; Faas, Transfusion 37:38-44, 1997, Faas, Transfusion 36:506-11, 1996), nonsense-mutations (Avent, Blood 89:2568-77, 1997), frameshifts (Andrews, Blood 92:1839-40, 1998; Cherif-Zahar Br. J. Haematol. 102:1263-70, 1998), or pseudogenes (Singleton, Blood 95:12-8, 2000). Such alleles are frequent in Africans (Faas, Transfusion 37:38-44, 1997, Singleton, Blood 95:12-18, 2000) and Asians (Okuda, J. Clin. Invest. 100:373-9, 1997) but rare in whites. Nevertheless, recent analyses (Avent, Blood 89:2568-77, 1997; Flegel, Transfus. Med. 8:281-302, 1998) suggested that even for whites these alleles are likely the leading cause of incorrect Rh phenotype prediction. Several observations in whites (Avent, Blood 89:2568-77, 1997; Hyland, Blood 84:321-4, 1994) indicated that these alleles clustered in the Cde and cdE haplotypes.

The most direct approach for analyzing the RHD locus on the molecular level would be PCR amplification spanning the RHD deletion site. Such an assay has, so far, not been available because the structure of the RHD locus in RhD positives and RhD negatives was incompletely understood.

Accordingly, the technical problem underlying the present invention was to provide means and methods for a reliable, nucleic acid based analysis of the Rhesus D locus. These means and methods should be, inter alia, suitable for the detection and/or discrimination of $RHD^{+}/RHD^{+}$ and $RHD^{+}/RHD^{-}$ individuals.

The solution to said technical problem is achieved by providing the embodiments characterized in the claims.

Thus, the invention relates to a nucleic acid molecular structure representing the Rhesus genes locus comprising the RHD, SMP1, and RHCE genes and/or the Rhesus boxes, preferably the hybrid Rhesus box, the upstream Rhesus box and/or the downstream Rhesus box, the sequences of which are shown in FIGS. 8 to 10.

In the context of the present invention, the term "nucleic acid molecular structure" is defined as a linear DNA-segment that comprises, in its broadest meaning, the combination of the above mentioned genes, namely the RHD, SMP1 and RHCE genes, arranged in this 5' to 3' order and/or Rhesus boxes that co-determine said Rhesus gene locus. DNA sequences that give rise to the molecular structure of the invention include the following: The nucleotide sequence structure consists of a Rhesus box 5' flanking region, the hybrid Rhesus box or two Rhesus boxes with intervening RHD gene, and the Rhesus box 3' flanking region.

The following sequences represent preferred embodiments contained in the nucleic acid molecular structure of the invention.

The Rhesus box 5' flanking region is represented in the genomic clone HS465N24 (GenBank accession number AL031432.1), bases 1 to 120,156.

The hybrid Rhesus box is represented in GenBank accession number AL252313 bases 33 to 9,180.

The two Rhesus boxes with intervening RHD gene consists of the upstream Rhesus box, represented in GenBank accession number AL252311 bases 34 to 9,175, the RHD gene and the downstream Rhesus box represented in GenBank accession number AL252312 bases 23 to 9,177 (see FIGS. 8 to 10).

The Rhesus box 3' flanking region consists of a small DNA segment between the downstream or hybrid Rhesus box and the SMP1 gene, the SMP1 gene and the RHCE gene.

The RHD gene consists of a RHD 5' region homologous to genomic clone HS469D22 (GenBank accession number AL031284.9) bases 56,012 to 51,472; also represented by a nucleotide segment dubbed "stuffer fragment" (GenBank accession number AB029152) bases 7,716 to 11,005; the RHD promoter (GenBank accession number AJ252314) bases 1 to 1,246 (see FIG. 11) and the RHD gene defined by the RHD cDNA (GenBank accession number X63097) bases 1 to 1,371 and by its intron sequences.

The small DNA segment preferably comprises 15 nucleotides between the downstream or hybrid Rhesus box and the SMP1 gene and is represented in AL252312 by bases 9,178 to 9,192.

The SMP1 gene is defined by the SMP1 cDNA represented in GenBank accession number AF0811282 and by its intron sequences.

The RHCE gene is defined by the RHCE cDNA represented in GenBank accession number X63095 and by its intron sequences and further represented in part by the genomic clone HS469D22 (GenBank accession number AL031432.1) bases 1 to 51,471 and the RHCE 5' flanking region represented by genomic clone HS469D22 bases 51,472 to 84,811.

Whereas the upstream Rhesus box is located 5' of the RHD gene, the downstream Rhesus box is located between the RHD and SMP1 genes in this structure of the present invention. Alternatively, the term "nucleic acid molecular structure" relates to DNA segments solely comprising the referenced Rhesus boxes. This term, in a further alternative, relates to DNA segments comprising the RHD, SMP1 and RHCE genes and two Rhesus boxes, namely the upstream Rhesus box and the downstream RHD box. Comprised by this term are also, in a further alternative, DNA segments that comprise the hybrid Rhesus box, the SMP1 gene and the RHCE gene. In another alternative, the term relates to DNA segments comprising the SMP1 gene and the hybrid Rhesus box. This term in a further alternative relates to DNA segments comprising the upstream Rhesus box, RHD, downstream Rhesus box and SMP1.

This term in another alternative relates to DNA segments comprising the downstream Rhesus box and SMP1. For a better understanding of the claimed subject-matter, it is referred to FIGS. 1 and 7, infra.

In accordance with the present invention, the term "nucleic acid molecular structure" comprises also any feasible derivative of the above referenced nucleic acid structure to which a nucleic acid probe may hybridize. In other words, the structure of the invention may be prepared by synthetic or semi-synthetic means and thus consist of or comprise peptide nucleic acid. Said term also bears the meaning of a nucleic acid molecule.

In accordance with the present invention, the term "Rhesus box" describes upstream and downstream DNA segments that flank the RHD gene on the 5' and 3' end. The three Rhesus boxes are defined by their nucleotide sequences. The hybrid Rhesus box is represented in one embodiment in GenBank accession number AL252313 bases 33 to 9,180. The two Rhesus boxes with intervening RHD gene consists of the upstream Rhesus box, represented in one embodiment in GenBank accession number AL252311 bases 34 to 9,175 and the downstream Rhesus box represented in one embodiment in GenBank accession number AL252312 bases 23 to 9,177. As exemplified in the appended examples the Rhesus boxes are preferably approximately 9000 bp long, having 98.6% identity and identical orientation. According to the present invention the upstream and downstream Rhesus boxes are at least 95% homologous. The length of these Rhesus boxes may vary. It is expected that the length of these Rhesus boxes may vary, because, among other structural features, multiple repetitive elements, some of them are organized in tandem arrays, are known to be prone to (array) elongation and deletion events. If such events occur the length of the Rhesus boxes may shrink to less than 1,000 nucleotides length or extend to more than 20,000 nucleotides length.

In accordance with the present invention the term "identity" refers to the determination of sequence identity using suitable alignment programs, such as BLAST.

As has been pointed out above, the diagnostic analysis of RHD negatives on the molecular level has so far been hampered by the fact, that the overall structure of the RHD/RHCE loci was unknown. It has now been surprisingly found, that the two genes, RHD and RHCE, have opposite orientation and face each other with their 3' ends. In accordance with the present invention it has further been found that the RHD gene is surrounded by two highly homologous Rhesus boxes. The physical distance between RHD and RHCE is about 30,000 bp and is filled with a Rhesus box and the SMP1 gene. The breakpoints of the RHD deletion in the prevalent RHD negative haplotypes are located in the 1,463 bp identity region of the Rhesus boxes. Similar RHD deletion events may involve any other region within the highly homologous Rhesus boxes. Hence, a region of a breakpoint comprising an RHD deletion other than the common RHD deletion may be anticipated to occur anywhere within the Rhesus boxes as defined above.

The opposite orientation of the two RH genes explains the different character of hybrid genes in the MNS and RH blood group: The glycophorin genes encoding the MNS antigens occur in the same orientation (Onda, Gene 159:225, 1995), and many recombinations may be explained as unequal crossing over resulting in single hybrid genes (Blumenfeld, Hum. Mutat. 6:1999, 1995). Based on the surprising findings referred to above, the events on the molecular level that lead to RHD negatives can now be more fully understood. In the RH locus, the inversely oriented sequences are unlikely to trigger unequal crossing over, and if this event occurred, no functional hybrid gene would result. The conclusion that unequal crossing over at the RH gene locus is unlikely may explain that most RH hybrid genes are of RHD-CE-D or RHCE-D-CE type and involve stretches of homologous DNA positioned in cis as noted previously (Wagner, Blood 91:2157, 1998). Currently, the RH gene system is the only well investigated gene locus where the two genes have opposite orientation, rendering it a model system for the evolution of neighboring, oppositely oriented genes that are frequent throughout genomes.

Figure 4:
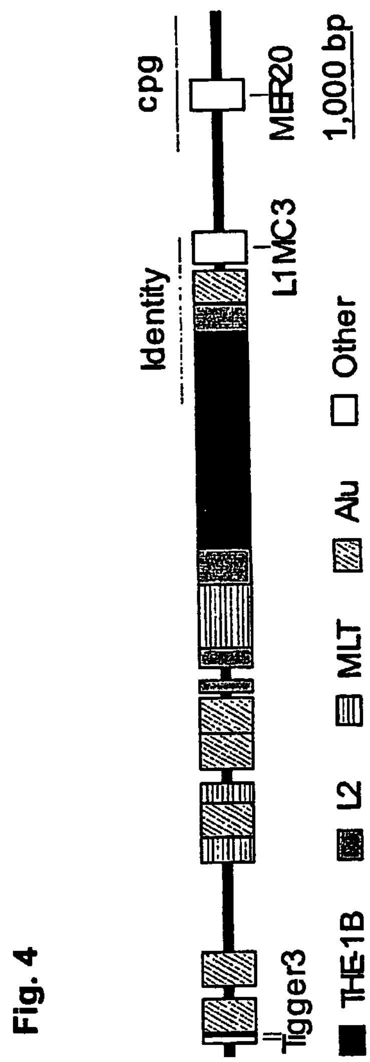
Figure 7:
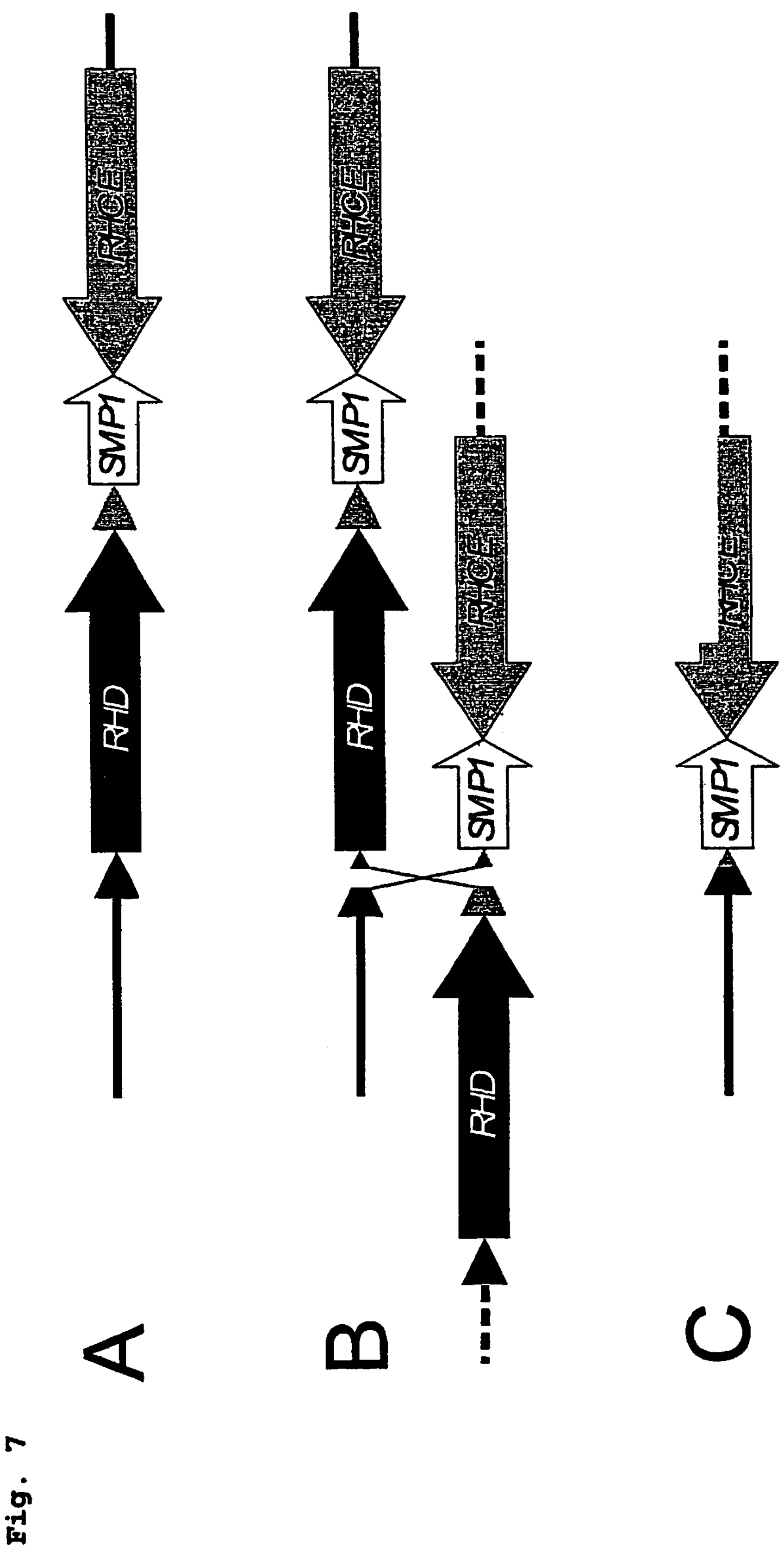

Based on the structure of the RH gene locus (FIG. 1), a parsimonious model for the RHD gene deletion event is proposed (FIG. 7). Although the applicant does not wish to be bound to theory, the following is believed with regard to the generation of RhD negative. The RHD deletion may be explained by unequal crossing over triggered by the highly homologous Rhesus boxes embracing the RHD gene. The hybrid-type Rhesus box of RHD-negatives arises, when a crossover leading to a deletion event involving a breakpoint region within the identity region of the upstream and downstream Rhesus boxes takes place. Thus, the hybrid RHD box is characterized by a 5' portion derived from the upstream RHD box fused to a 3' portion from the downstream RHD box. In one preferred embodiment the breakpoint region is 903 bp long. The sequence of this preferred hybrid Rhesus box is depicted in FIG. 5. In the specific embodiments described in the examples, said 903 bp breakpoint region in the Rhesus boxes is located in a 1,463 bp stretch of 99.9% homology resembling a THE-1B human transposable element and a L2 repetitive DNA element (FIG. 4). Interestingly, the >60,000 bp DNA segment that is deleted in the RHD negative haplotype consisted only of and contained all sequences that are duplicated in the RHD positive haplotype.

The findings of the present invention referred to herein above allow for the establishment of a number of easy to do or refined methods for the analysis of the genotype of an individual with regard to the RH gene locus. Examples of such methods are provided herein below.

While the molecular mechanism resulting in the prevalent RHD negative haplotype is now apparent, it is less clear how the much older duplication event gave rise to the structure of the RH genes in RHD positives. The duplication of the Rhesus box and the RH genes probably occurred as a single event, because the overall homology of the two Rhesus boxes is very similar to that of the RH genes. Without being bound by theory, it is tempting to speculate that the RHD duplication originate in causal connection with the insertion of the near full-length THE-1B transposon-like human element in duplicate. However, the open reading frame of the THE-1B element probably was non-functional at the time of the duplication.

In a preferred embodiment of the present invention, said nucleic acid molecular structure is representative of the common RHD negative haplotypes.

According to the present invention, the term "is representative of" relates to a nucleic acid molecular structure comprising all sequential and structural features to relate said structure to a group of molecular structures sharing said features. In the above preferred embodiment, said features give rise to the common RHD negative haplotype. In the present context this means preferably the deletion of the RHD gene encompassing the whole RHD gene and its 5' region, which are located between the upstream Rhesus box and the downstream Rhesus box.

In the present context this could also mean, for example, that all structures sharing a nonsense mutation, missense mutation, splice site mutation, partial deletion, partial insertion, partial inversion or a combination thereof within the RHD gene, which terminates or obliterates the expression of a protein product of the RHD gene, are representative of the RHD negative haplotype.

The term "haplotype" relates to a series of linked alleles within a defined region on a single maternal or paternal chromosome.

The term "common RHD negative haplotype" refers to any RhD antigen negative haplotype that comprises a hybrid Rhesus box. Preferably the DNA segment encompassing the whole RHD gene and its 5' region, which are located between the upstream Rhesus box and the downstream Rhesus box, is deleted.

In another embodiment, the invention relates to a nucleic acid molecular structure, dubbed Rhesus box, which is flanking the breakpoint region of the RHD deletion in the common RHD negative haplotypes.

In accordance with the present invention the term "breakpoint region of the RHD deletion" describes a distinct DNA segment that is involved in an RHD deletion. As has been pointed out above, said deletion may be the result of an unequal crossing over event involving both the upstream and downstream Rhesus boxes, deleting interspersed sequences and finally giving rise to a nucleic acid molecular structure (the referenced Rhesus boxes for a better delimitation from the upstream and downstream Rhesus box also referred to as hybrid Rhesus box) wherein the 5' portion of the upstream RHD box is in close spatial proximity to the 3' portion of the downstream RHD box. As mentioned above and depicted in FIGS. 7 and 4 this region can preferably be 903 bp long and be located in a 1,463 bp stretch within the Rhesus boxes, having 99.9% homology in this segment. In another preferred alternative said region is located downstream from said 903 bp fragment but is still contained within the 1463 bp stretch. Preferably, said fragment is 556 to 560 bp long. The actual breakpoint may vary such that the contribution of the upstream Rhesus box and the downstream Rhesus box are different in different individuals. However, in accordance with the present invention, the breakpoint in any case occurs in the upstream and downstream Rhesus boxes.

The hybrid Rhesus box is particularly useful for the analysis of RHD-negative haplotypes. For example, oligonucleotides may be employed that hybridize to nucleic acid sequences comprising the breakpoint which arose as a result of the RHD deletion. It is to be understood that such oligonucleotides need to hybridize to a significant portion preferably encompassing 20 nucleotides, that is located 5' and 3' of the region of the actual breakpoint in order to be indicative of a deletion event. For example, when such an oligonucleotide is hybridized under stringent conditions such as 0.2×SSC, 0.1 SDS at 65° C. and the probe would be 943 nucleotides long, then the hybridizing region should include portions that hybridize 3' as well as 5' of the breakpoint.

For example, a Rhesus box or a part thereof encompassing the region of the breakpoint is amplified. Thereafter the amplification product is assayed in a sequence specific way by hybridization to an oligonucleotide of about six or more nucleotides length.

Preferably, a stretch of DNA representative of a Rhesus box or part thereof encompassing the region of the breakpoint is amplified using two primers. One primer may be located in the Rhesus box 5' of the identity region and is specific for both the upstream Rhesus box and the hybrid Rhesus box. The other primer may be located in the Rhesus box 3' of the identity region and is specific for both the downstream Rhesus box and the hybrid Rhesus box. In this application, the presence of an amplification product of the expected size is indicative of the presence of a hybrid Rhesus box and hence, of the RHD deletion.

Another possible combination of primers is the following: One primer may be located in the Rhesus box 5' of the identity region and is specific for both the upstream Rhesus box and the hybrid Rhesus box. The other primer may be located in the Rhesus box 3' of the identity region. In this application, the presence of a hybrid Rhesus box is determined by examining the specificity of the parts of the amplification product pertaining to a DNA stretch of the Rhesus box 3' of the identity region. This may for example be effected by hybridization with an oligonucleotide that hybridizes to the hybrid Rhesus box and to the downstream Rhesus box but not to the upstream Rhesus box, or by digestion with a restriction enzyme that cuts the hybrid Rhesus box and the downstream Rhesus box but does not cut the upstream Rhesus box, or by digestion with a restriction enzyme that does not cut the hybrid Rhesus box and the downstream Rhesus box but cuts the upstream Rhesus box, or by nucleotide sequencing.

Another possible combination of primers is the following: One primer may be located in the Rhesus box 5' of the identity region. The other primer may be located in the Rhesus box 3' of the identity region and is specific for both the downstream Rhesus box and the hybrid Rhesus box. In this application, the presence of a hybrid Rhesus box is determined by examining the specificity of the parts of the amplification product pertaining to a DNA stretch of the Rhesus box 5' of the identity region. This may for example be effected by hybridization with a nucleotide that hybridizes to the hybrid Rhesus box and to the upstream Rhesus box but not to the downstream Rhesus box, or by digestion with a restriction enzyme that cuts the hybrid Rhesus box and the upstream Rhesus box but does not cut the downstream Rhesus box, or by digestion with a restriction enzyme that does not cut the hybrid Rhesus box and the upstream Rhesus box but cuts the downstream Rhesus box, or by nucleotide sequencing.

The hybrid Rhesus box may also serve as a diagnostic tool for the presence of the RHD deletion when analyzed by an anti-DNA antibody specific for one or more embodiments of the hybrid box, a fragment or derivative thereof such as an scFvFab or $F(ab')_2$ fragment or an aptamer etc. Thus, antibodies, fragments or derivatives thereof or such aptamers can be generated by the person skilled in the art according to conventional technology (see, for example, Harlow and Lane, "Antibodies, A Laboratory Manual", CSH Press 1988, Cold Spring Harbor).

In a preferred embodiment, the invention relates to a nucleic acid molecular structure representative of an RHD negative haplotype comprising an RHD gene deletion involving the upstream Rhesus box, the downstream Rhesus box, or both.

The invention further relates to a nucleic acid molecular structure that is flanking the Rhesus box in the common RHD negative haplotypes. These structures or sequences can be used to derive primers for amplification reactions such as long range PCR for the molecular analysis of the RHD locus.

For example, a stretch of DNA representative of a Rhesus box and parts of their flanking regions or parts thereof encompassing the region of the breakpoint is amplified using two primers. One primer may be located in the 5' flanking region of the Rhesus box. Alternatively, this primer may be located in the Rhesus box 5' of the identity region and is specific for both the upstream Rhesus box and the hybrid Rhesus box. The other primer may be located in the Rhesus box 3' flanking region. Alternatively, this primer may be located in the Rhesus box 3' of the identity region and is specific for both the downstream Rhesus box and the hybrid Rhesus box. In this application the presence of an amplification product of the expected size is indicative of the presence of a hybrid Rhesus box and hence, of the RHD deletion.

Another possible combination of primers is the following: One primer may be located in the 5' flanking region of the Rhesus box. The other primer may be located in the Rhesus box 3' of the identity region. In this application, the presence of a hybrid Rhesus box is determined by examining the specificity of the parts of the amplification product pertaining to a DNA stretch of the Rhesus box 3' of the identity region. This may for example be effected by hybridization with an oligonucleotide that hybridizes to the hybrid Rhesus box and to the downstream Rhesus box but not to the upstream Rhesus box, or by digestion with an restriction enzyme that cuts the hybrid Rhesus box and the downstream Rhesus box but does not cut the upstream Rhesus box, or by digestion with a restriction enzyme that does not cut the hybrid Rhesus box and the downstream Rhesus box but cuts the upstream Rhesus box, or by nucleotide sequencing.

Another possible combination of primers is the following: One primer may be located in the Rhesus box 5' of the identity region. The other primer may be located in the 3' flanking region of the Rhesus box. In this application, the presence of a hybrid Rhesus box is determined by examining the specificity of the parts of the amplification product pertaining to a DNA stretch of the Rhesus box 5' of the identity region. This may for example be effected by hybridization with an oligonucleotide that hybridizes to the hybrid Rhesus box and to the upstream Rhesus box but not to the downstream Rhesus box, or by digestion with an restriction enzyme that cuts the hybrid Rhesus box and the upstream Rhesus box but does not cut the downstream Rhesus box, or by digestion with a restriction enzyme that does not cut the hybrid Rhesus box and the upstream Rhesus box but cuts the downstream Rhesus box, or by nucleotide sequencing.

In a preferred embodiment the nucleic acid molecular structure is representative of RHD positive haplotypes.

The term "RHD positive haplotype" refers to any haplotype that comprises DNA sequences specific for the RHD gene.

In a preferred embodiment the invention relates to a nucleic acid molecular structure representative of the common RHD positive haplotype.

In another preferred embodiment the nucleic acid molecular structure is derived from a sample comprising an RHD positive haplotype that is serologically classified RhD negative.

In the context of the invention, the term "serologically classified RhD negative" describes a sample that has been tested for the presence of RhD antigen using, e.g., routine serological assays wherein the result of such assays was negative.

In a particularly preferred embodiment the sample that is classified RhD negative is obtained from a Caucasian population.

In another more preferred embodiment the nucleic acid molecular structure comprises a partial RHD deletion.

One alternative for explaining that an allele routinely diagnosed RHD positive gives rise to a RhD-negative phenotype is the deletion of a part of the RHD gene or the substitution of a part of the RHD gene by the corresponding DNA segments derived from the RHCE gene not detected by standard diagnostic methods such as PCR.

In a preferred embodiment said deletions or substitutions comprise RHD exons 3 to 7 or 4 to 7 giving rise to a CcddEe phenotype, or 1 to 9.

In a most preferred embodiment said substitution comprises a RHD-CE(3-7)-D hybrid gene, a RHD-CE(4-7)-D hybrid gene giving rise to a CcddEe phenotpye or a RHCE (1-9)-D(10) hybrid gene, all of which correlate with a RhD negative phenotype.

In another most preferred embodiment the nucleic acid molecular structure of the present invention comprising an RHD-CE-D hybrid allele, which is representative of a Cde$^s$ haplotype but also occurs in other Rhesus haplotypes, carrying a 5' breakpoint region located in intron 3, the sequence of which breakpoint region is shown in FIG. 12, and/or a 5' breakpoint region located in intron 7, the sequence of which breakpoint region is shown in FIG. 13, or both breakpoint regions.

Cde$^s$, also known as r'$^s$, is a RH haplotype resembling Cde that was initially characterized as expressing antigen e$^s$ instead of antigen e, expressing antigen c, and expressing reduced and altered antigen C (Issitt, P. D. *Aplied Blood Group Serology*, Miami: Montgomery Scientific Publications, 1985, page 239). The molecular structure underlying this haplotype has recently been elucidated (Blunt, T., Daniels, G., and Carritt, B. Serotype switching in a partially deleted *RHD gene. Vox Sang.* 67:397-401, 1994; Faas, B. H. W., Becker, E. A. M., Wildoer, P., Ligthart, P. C., Overbeeke, M. A. M., Zondervan, H. A., von dem Borne, A. E. G. K., and van der Schoot, C. E. Molecular background of VS and weak C expression in blacks. *Transfusion* 37:38-44, 1997; Daniels, G. L., Faas, B. H., Green, C. A., Smart, E., Maaskant-van Wijk, P. A., Avent, N. D., Zondervan, H. A., von dem Borne, A. E., and van der Schoot, C. E. The VS and V blood group polymorphisms in Africans: a serologic and molecular analysis. *Transfusion* 38:951-958, 1998.): The Cde$^s$ haplotype contains a RHD-CE-D hybrid gene encoding for an antigen C immunoreactivity, in which exons 4 to 7 derived from RHCE and exon 3 has a RHD like structure but possesses a RHCE specific Thr at codon 152.

Several additional RHD positive alleles occurring in RhD negative individuals have previously been partly or fully characterized (Table 10). Three of these ten published RHD alleles represented RHD-CE-D hybrid alleles in which the RHCE specific stretch encompassed at least exons 4 to 7. For each of these three hybrid RHD alleles, alleles were found whose patterns would be compatible (Table 10). Out of the seven RhD negative patterns observed in the present study, six were compatible with such type of hybrid RHD allele. Seven out of ten published RHD alleles represented deletions, nonsense mutations or a pseudogene. None of these alleles occurred in this study, which may indicate that they are rare in whites. In another embodiment, the invention provides for the detection or determination of the RHD allele previously described as RHD exon 9 negative (Gassner, Transfusion 37:1020ff, 1997), preferably representing an hybrid RHD-CE(9)-D hybrid allele, by its lack of RHD specific sequences in parts of intron 7 and intron 8. The specific steps carried out in this method may be any of the steps referred to in the further methods of the invention described in the specification, alone or in any combination.

In a particularly preferred embodiment the nucleic acid molecular structure of the present invention wherein the RHD-CE-D hybrid of the present invention encodes a polypeptide having antigen C reactivity.

Antigen C is a blood group antigen belonging to the RH blood group system known in the art and designated as 004.002 according to the ISBT nomenclature. A description is contained in many textbooks on immunohematology, e.g. Reid, M. E. and Lomas-Francis, C. *The Blood Group Antigen Facts Book*, San Diego: Academic Press, 1997.

Furthermore, in a preferred embodiment of the invention the nucleic acid molecular structure of the invention or a nucleic acid molecule being derived from the RHD gene comprises a single nucleotide substitution within the coding region of the RHD gene or within a 5' or 3' splice site.

The term "a nucleic acid molecule derived from the RHD gene" is intended to mean that this nucleic acid molecule originates from the RHD gene but carries a mutation, deletion, insertion, substitution or duplication within the coding region, any of the splice sites or a non-coding region. Preferably, said nucleic acid molecule gives rise to an aberrant polypeptide.

In a further preferred embodiment said nucleotide substitution gives rise to a stop-codon at codon 16.

In a more preferred embodiment said substitution gene gives rise to an RHD(W16X) mutation.

In an additional more preferred embodiment said substitution is a G→A substitution at nucleotide position 48.

In a further preferred embodiment of the invention said nucleotide substitution gives rise to a stop codon at codon 330.

In a more preferred embodiment of the invention said substitution gives rise to a RHD(Y330X) mutation.

In an even more preferred embodiment of the invention said substitution is a C→G substitution at nucleotide position 985.

In another preferred embodiment of the invention said substitution gives rise to a missense mutation at codon 212.

In another preferred embodiment of the invention said substitution gives rise to a RHD(G212V) missense mutation.

In a more preferred embodiment of the invention said substitution is a G→T substitution at nucleotide position 635.

In a different preferred embodiment of the invention said substitution gives rise to a mutation within a 4 nucleotide sequence, a 6-nucleotide sequence or an 8-nucleotide sequence comprising the consensus splice site at the exon 8/intron 8 boundary.

In another more preferred embodiment of the invention said substitution give rise to a RHD(G1153(+1)A) mutation.

In an additional more preferred embodiment of the invention said substitution is a substitution at the 5' splice site intron 8 from AGgt to AGat.

In a further more preferred embodiment the nucleic acid molecular structure of the invention or a nucleic acid molecule being derived from the RHD gene correlates with a RhD-negative phenotype.

In another preferred embodiment of the invention said substitution gives rise to a mutation within a 4-nucleotide, a 6-nucleotide sequence or an 8-nucleotide sequence comprising the consensus splice site of the exon 3/intron3 boundary.

In a further preferred embodiment of the invention said substitution gives rise to a RHD(G486(+1)A) mutation.

In an additional more preferred embodiment of the invention said substitution is a substitution at the 5' splice site intron 3 from ACgt to ACat.

In a further preferred embodiment of the invention said substitution gives rise to a mutation within a 4-nucleotide sequence, a 6-nucleotide sequence or an 8-nucleotide sequence comprising the consensus splice site of exon 9/intron 9 boundary.

In another preferred embodiment said substitution gives rise to a RHD(K409K) mutation.

In an additional more preferred embodiment of the invention said substitution is a substitution at the 5' splice site intron 9 from AGgt to AAgt.

In a more preferred embodiment of the invention the nucleic acid molecular structure of the invention or a nucleic acid molecule being derived from the RHD gene correlates with a $D_{el}$-phenotype.

In summary and referring to the above, RHD positive alleles can harbour single nucleotide substitutions leading to termination or reduction of the D-antigen expression. Using the improved detection methods disclosed in the present invention four RHD positive alleles in RhD negatives were found that had not been described previously. Two alleles, RHD(W16X) and RHD(Y330X) harbored stop codons preventing the expression of the full RhD protein. In three alleles, splice site mutations were found that may prevent correct splicing and RhD expression.

These alleles typed D positive in all RHD PCR methods tested, and a correct antigen D prediction necessitates a specific detection of these alleles or of polymorphisms linked to these alleles.

Previously, the discrimination of RHD homozygotes from RHD heterozygotes was difficult. The prevalent RHD negative allele could not be detected specifically (Flegel, Transfus. Med. 8:281, 1998; Cossu, Electrophoresis 17:1911, 1996). The above defined mutation found in accordance with the present invention provides the basis for the detection of the prevalent RHD negative haplotypes, and hence true RHD genotyping is now feasible.

The invention also relates to a process to specifically detect a RHD negative haplotype in a sample by utilizing any structural feature or nucleotide sequence or both of the above-described nucleic acid molecular structure or combinations thereof with techniques known in the art, preferably amplification reactions, such as polymerase chain reaction (PCR), more preferably by PCR-RFLP, PCR-SSP or long-range PCR.

The described PCR-RFLP and long-range PCR methods utilize either Rhesus box sequences or Rhesus box flanking sequences. By utilizing the same DNA stretches or combinations thereof, other methods, like PCR-SSO or biochips, can be developed or applied.

In one preferred embodiment of the present invention said process to specifically detect a common RHD negative haplotype comprises the following steps:

(a) isolating the DNA from a blood sample or blood donor;
(b) hybridizing at least two oppositely oriented primers under stringent conditions to the DNA so as to carry out a PCR;
(c) amplifying the target sequence;
(d) separating the amplification products on a gel; and
(e) analyzing the amplicons.

Said sample may or may be derived from blood, serum, sputum, feces or other body fluid. The sample to be analyzed may be treated as to extract, inter alia, nucleic acids. The isolation of DNA from preferably EDTA- or citrate agglutinated blood samples can be carried out by a modified salting out methods, following the standard techniques as described in Gassner, Transfusion 37: 1020, 1997. The primers are preferably oligonucleotides that either occur naturally or in a purified restriction digest or are produced synthetically. The primers are preferably single stranded for a maximum of efficiency in the method of the present invention, and are preferably oligodeoxyribonucleotides. Purification of said primers is generally envisaged, prior to their use in the methods of the present invention, said purification comprising High Performance Liquid Chromatography (HPLC) or Polyacrylamide gel electrophoresis (PAGE), all technologies that are well known to the skilled artisan. Amplification methods such as PCR or LCR are well known in the art and described, for example in Flegel, Transfusion Medicine 8 (1998), 281-302; Maaskant, Transfusion 38 (1998), 1015-1021 and Legler, Transfusion (1996), 426-31.

According to the present invention a preferred method to detect the RHD deletion is performing PCR-RFLP using the expand high fidelity PCR-system and non-specific primers binding 5' of the end of the Rhesus box identity region as well as primers specific for the downstream Rhesus box and binding 3' of the end of the Rhesus box identity region. The PCR conditions involve preferably annealing at 65° C., extension for 10 min at 68° C. Thereafter, PCR amplicons are digested with PstI for 3 h at 37° C. and fragments resolved using 1% agarose gel. Additional preferred methods are further described in examples 10 and 11.

Another embodiment of the invention relates to a process to specifically detect a common RHD negative haplotype comprising the detection of the hybrid Rhesus box.

The detection of the hybrid Rhesus box provides the practitioner with an unambiguous result as regards the nature of the corresponding RHD allele. If the hybrid Rhesus box is detected, then the RHD gene is deleted. Detection of the hybrid Rhesus box is preferentially effected by using an oligonucleotide that specifically hybridizes to a region comprising the breakpoint. The oligonucleotide used for hybridization must directly hybridize to that breakpoint and, in addition, hybridize to at least 943 nucleotides 5' and 3' of the breakpoint. Hybridization occurs preferably under stringent conditions such as 0.2×SSC, 0.1% SDS at 65° C. The actual breakpoint within the hybrid Rhesus box may vary due to the exact nature of the putative crossover event. Accordingly, the hybrid Rhesus box may also be detected using a number of overlapping or non-overlapping oligonucleotides used for hybridization. The hybrid Rhesus box may also be detected using other protocols such as restriction analysis (preferably in combination with Southern blot analysis), or PCR technology, as described herein above.

Furthermore, another embodiment of the invention relates to a process to specifically detect a common RHD negative haplotype comprising assessing the nucleic acid molecular structure comprising the hybrid Rhesus box and the flanking regions thereof.

In accordance with the present invention, assessment of the molecular nucleic acid structure comprises analysis steps such as gel electrophoresis using either agarose gels or polyacrylamide gels, treatment with restriction-enzymes, blotting techniques, such as Southern or Northern blotting or related techniques, such as fluorescence-guided detection of hybridization and other techniques known in the art.

The present invention also relates to a process to specifically detect a RHD negative haplotype in a sample comprising the step of detecting any of the breakpoint regions mentioned in the present invention.

In a preferred embodiment the invention relates to the above-mentioned process wherein said detection or assessment comprises the determination of the length of a nucleic acid molecule comprising the hybrid Rhesus box or parts thereof.

Again, this preferred embodiment of the method of the invention utilizes standard separation techniques, such as gel electrophoresis or chromatography or standard techniques of nucleotide sequencing as known to a skilled artisan. Preferably the present invention utilizes a commercially available sequencing kit and an automatic sequencing machine from Applied Biosystems (ABI 373A or ABI 377), as further described in Example 5, for this purpose.

Another preferred embodiment of the invention relates to the above-mentioned process wherein said detection or assessment is effected by using PCR-RFLP, PCR-SSP or long-range PCR or a probe specifically hybridizing to the hybrid Rhesus box, preferably to the breakpoint or breakpoint region depicted in FIG. 4 or 5 or FIG. 12 or 13, or hybridizing to the upstream or downstream Rhesus box, preferably by Southern blot analysis, gel electrophoresis, biochip-analysis, molecular weight determination or fluorescence.

According to the present invention the term "hybridizing to" relates to stringent or non-stringent conditions. The setting of conditions is well within the skill of the artisan and to be determined according to protocols described, for example, in Sambrook, loc. cit. or Hames and Higgins, "Nucleic acid hybridization, a practical approach", IRC Press, Oxford (1985). The detection of specifically hybridizing sequences will usually require stringent hybridizing and washing conditions such as 0.2×SSC, 0.1% SDS at 65° C. Non-stringent hybridization conditions for the detection of homologous and not exactly complementary sequences may be set at 6×SSC, 1% SDS at 50° C. or 65° C. As is well known, the length of the probe and the composition of the nucleic acid to be determined constitute further parameters of the hybridization conditions.

Furthermore, the invention relates to a vector comprising the nucleic acid molecular structure or the nucleic acid molecule of the invention.

The vector may be used for propagation and/or expression or may be designed for gene transfer or targeting purposes. Methods of producing such vectors are well known in the art. The same holds true for cloning the nucleic acids of the mutation into said vectors, as well as the propagation of vectors in suitable hosts, etc.

The vector may particularly be a plasmid, a cosmid, a virus or a bacteriophage used conventionally in genetic engineering that comprise the nucleic acid molecule of the invention. Expression vectors derived from viruses such as retroviruses, vaccinia virus, adeno-associated virus, herpes viruses, or bovine papilloma virus, may be used for delivery of the nucleic acid molecules or vector of the invention into targeted cell populations. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1989). Alternatively, the polynucleotides and vectors of the invention can be reconstituted into liposomes for delivery to target cells. The vectors containing the nucleic acid molecules of the invention can be transferred into the host cell by well-known methods, which vary depending on the type of cellular host. For example, calcium chloride transfection is commonly utilized for prokaryotic cells, whereas calcium phosphate treatment or electroporation may be used for other cellular hosts; see Sambrook, supra.

Such vectors may comprise further genes such as marker genes which allow for the selection of said vector in a suitable host cell and under suitable conditions. Preferably, the nucleic acid molecule of the invention is operatively linked to expression control sequences allowing expression in prokaryotic or eukaryotic cells. Expression of said polynucleotide comprises transcription of the polynucleotide into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers, and/or naturally-associated or heterologous promoter regions. Possible regulatory elements permitting expression in prokaryotic host cells comprise, e.g., the PL, lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Beside elements which are responsible for the initiation of transcription such regulatory elements may also comprise transcription termination signals, such as the SV40-poly-A site or the tk-poly-A site, downstream of the nucleic acid molecule. Furthermore, depending on the expression system used leader sequences capable of directing the polypeptide to a cellular compartment or secreting it into the medium may be added to the coding sequence of the polynucleotide of the invention and are well known in the art. The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including an C- or N-terminal identification peptide imparting desired characteristics, e.g., stabilization or simplified purification of expressed recombinant product. In this context, suitable expression vectors are known in the art such as Okayama-Berg cDNA expression vector pcDV1 (Pharmacia), pCDM8, pRc/CMV, pcDNA1, pcDNA3 (In-vitrogene), or pSPORT1 (GIBCO BRL).

Preferably, the expression control sequences will be eukaryotic promoter systems in vectors capable of transforming or transfecting eukaryotic host cells, but control sequences for prokaryotic hosts may also be used.

As mentioned above, the vector of the present invention may also be a gene transfer or targeting vector. Gene therapy, which is based on introducing therapeutic genes into cells by ex-vivo or in-vivo techniques is one of the most important applications of gene transfer. Suitable vectors and methods for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813; Isner, Lancet 348 (1996), 370-374; Muhlhauser, Circ. Res. 77 (1995), 1077-1086; Wang, Nature Medicine 2 (1996), 714-716; WO94/29469; WO 97/00957 or Schaper, Current Opinion in Biotechnology 7 (1996), 635-640, and references cited therein. The polynucleotides and vectors of the invention may be designed for direct introduction or for introduction via liposomes, or viral vectors (e.g. adenoviral, retroviral) into the cell. Preferably, said cell is a germ line cell, embryonic cell, or egg cell or derived therefrom, most preferably said cell is a stem cell.

Additionally, the invention relates to a non-human host transformed with the vector of the invention.

Appropriate hosts comprise transgenic animals, cells such as bacteria, yeast cells, animal, preferably mammalian cells, fungal cells or insect cells. Transformation protocols including transfection, microinjection, electroporation, etc., are also well known in the art.

Further, the invention relates to a method of producing a protein product of the RHD gene comprising culturing the host of the invention under suitable conditions and isolating the protein product of the RHD gene.

It is preferred that the protein product of the RHD gene is exported into the culture medium where it can be collected according to conventions/methods. The term "culturing" as used in accordance with the present invention also comprises the raising of transgenic animals. Using appropriate vectors constructions and optionally appropriate feeds, the antigen may, e.g., be isolated from milk of, e.g. transgenic cows.

The invention additionally relates to a protein product of the RHD gene encoded by the nucleic acid molecule of the invention or produced by the method of the invention.

Preferably, the protein is in the same way post translationally modified and has the same chemical structure as naturally occurring antigen. Accordingly, said protein, when produced by the method of the invention, is preferably produced in human cells.

Furthermore, the invention relates to an oligonucleotide hybridizing under stringent conditions to a portion of the nucleic acid molecular structure or the nucleic acid molecules of the invention, wherein said portion comprises said (missense) mutation or said stop codon or to the complementary portion thereof or hybridizing to a breakpoint of the gene conversion identified here in the above.

In this embodiment of the invention, it is understood that the oligonucleotides hybridizes directly to the mutated sequence or to the breakpoint. The setting of stringent hybridization conditions is well described, for example, in Sambrook et al, "Molecular Cloning, A Laboratory Handbook" CSH Press, Cold Spring Harbor 1989 or Hames and Higgins, "Nucleic acid hybridization, a practical approach", IRL Press, Oxford (1985). Thus, the detection of the specifically hybridizing sequences will usually require hybridization and washing conditions such as 0.2×SSC, 0.1% SDS at 65°. As is well known, the length of the probe and the composition of the nucleic acid to be determined constitute further parameters of the stringent hybridization conditions. Preferably, the oligonucleotide is a deoxynucleotide. It is further preferred that the oligonucleotide comprises 12 to 50 nucleotides and more preferably 15 to 24 nucleotides. The hybridization to the breakpoint may be under stringent or non-stringent conditions. An example of non-stringent hybridization conditions is hybridization and washing at 50° C. in 4×SSC, 0.1% SDS.

Further, the invention relates to an antibody or an aptamer specifically binding to the protein product of the RHD gene of the invention.

The antibody may be tested and used in any serologic technique well known in the art, like agglutination techniques in tubes, gels, solid phase and capture techniques with or without secondary antibodies, or in flow cytometry with or without immunofluorescence enhancement.

The antibody of the invention may be a monoclonal antibody or an antibody derived from or comprised in a polyclonal antiserum. The term "antibody", as used in accordance with the present invention, further comprises fragments of said antibody such as Fab, $F(ab')_2$, Fv or scFv fragments; see, for example, Harlow and Lane, "Antibodies, A Laboratory Manual" CSH Press 1988, Cold Spring Harbor, N.Y. The antibody or the fragment thereof may be of natural origin or may be (semi) synthetically produced. Such synthetic products also comprise non-proteinaceous as semi-proteinaceous material that has the same or essentially the same binding specificity as the antibody of the invention. Such products may, for example, be obtained by peptidomimetics.

The term "aptamer" is well known in the art and defined, e.g., in Osborne et al., Curr. Opin. Chem. Biol. I (1997), 5-9 or in Stall and Szoka, Pharm. Res. 12 (1995), 465-483.

Furthermore, the invention relates to a method for testing for the presence of a nucleic acid molecule encoding a mutant Rhesus D antigen or of a nucleic acid molecule carrying a deletion of the RHD gene as characterized by the nucleic acid molecular structure or the nucleic acid molecule of the invention in a sample comprising hybridizing the oligonucleotide of the invention under stringent conditions to nucleic acid molecules comprised in the sample obtained from a human and detecting said hybridization.

Preferably, the method of the invention further comprises digesting the product of said hybridization with a restriction endonuclease or subjecting the product of said hybridization to digestion with a restriction endonuclease and analyzing the product of said digestion.

This preferred embodiment of the invention allows by convenient means, the differentiation between an effective hybridization and a non-effective hybridization. For example, if the wild type RHD gene comprises an endonuclease restriction site, the hybridized product will be cleavable by an appropriate restriction enzyme whereas a mutated sequence will yield no double-stranded product or will not comprise the recognizable restriction site and, accordingly, will not be cleaved. Alternatively, the hybridizing oligonucleotide may only hybridize to the mutated sequence. In this case, only a hybrid comprising the mutated sequence, but not the wild type sequence, will be cleaved by the appropriate restriction enzyme. The analysis of the digestion product can be effected by conventional means, such as by gel electrophoresis which may be optionally combined by the staining of the nucleic acid with, for example, ethidium bromide. Combinations with further techniques such as Southern blotting are also envisaged.

Detection of said hybridization may be effected, for example, by an anti-DNA double-strand antibody or by employing a labeled oligonucleotide. Conveniently, the method of the invention is employed together with blotting techniques such as Southern or Northern blotting and related techniques. Labeling may be effected, for example, by standard protocols and includes labeling with radioactive markers, fluorescent, phosphorescent, chemiluminescent, enzymatic labels, etc.

The invention also relates to a method to simultaneously detect the presence of RHDΨ and any of the RHD molecular structures of the invention comprising hybridizing the oligonucleotide of the invention and at least an other oligonucleotide hybridizing to a RHDΨ structure under stringent conditions to nucleic acid molecules comprised in the sample obtained from a human and detecting said hybridization.

The present invention further relates to a method for testing simultaneously for the presence of RHDΨ and any of the RHD molecular structures of the present invention in a sample comprising determining the nucleic acid sequence of at least a portion of the nucleic acid molecular structure or nucleic acid molecule of the present invention, said portion encoding said (missense) mutation, said stop codon or a breakpoint of said hybrid gene and determining of at least a portion of a RHDΨ structure.

The invention additionally relates to a method for testing for the presence of a nucleic acid molecule encoding a mutant Rhesus D antigen or of a nucleic acid molecule carrying a deletion of the RHD gene as characterized by the nucleic acid molecular structure or the nucleic acid molecule of the invention in a sample comprising determining the nucleic acid sequence of at least a portion of the nucleic acid molecular structure or the nucleic acid molecule of the invention, said portion encoding said (missense) mutation, said stop codon or a breakpoint of said hybrid gene.

Preferably, the method of the invention further comprises, prior to determining said nucleic acid sequence, amplification of at least said portion of said nucleic acid molecular structure.

Moreover, the invention relates to a method for testing simultaneously for the presence of RHDΨ and any of the RHD molecular structures of the present invention in a sample comprising carrying out an amplification reaction using a set of primers that amplifies at least a portion of said sequence wherein at least one of the primers employed in said amplification reaction is the oligonucleotide of the present invention and at least a primer amplifying (e.g. by specifically hybridizing to) a RHDΨ structure and analysing the amplified product(s).

RHDΨ is a RHD allele detected in D negatives that has been characterized by Singleton et al. (Singleton, B. K., Green, C. A., Avent, N. D., Martin, P. G., Smart, E., Daka, A., Narter-Olaga, E. G., Hawthorne, L. M., and Daniels, G. The presence of an RHD pseudogene containing a 37 base pair duplication and a nonsense mutation in africans with the Rh D-negative blood group phenotype. Blood 95(1):12-18, 2000).

Furthermore, the invention relates to a method for testing for the presence of a nucleic acid molecule encoding a mutant Rhesus D antigen or of a nucleic acid molecule carrying a deletion of the RHD gene as characterized by the nucleic acid molecular structure or the nucleic acid molecule of the invention in a sample comprising carrying out an amplification reaction using a set of primers that amplifies at least a portion of said sequence wherein at least one of the primers employed in said amplification reaction is the oligonucleotide of the invention.

Moreover, in a further embodiment the method of the invention wherein at least one of the primers employed in said amplification reaction is the oligonucleotide of the invention.

Preferably, amplification is effected by polymerase chain reaction (PCR). Other amplification methods such as ligase chain reaction may also be employed.

In a preferred embodiment of the method of the invention said PCR is PCR-RFLP, PCR-SSP or long-range PCR.

Additionally, in another preferred embodiment of the invention the molecular weight of the amplification product is analyzed. Said analysis of the molecular weight utilizes standard techniques, such as agarose gel electrophoresis, SDS-PAGE, mass spectrometry such as MALDI-TOF for this purpose, which are well known to the person skilled in the art.

In one preferred embodiment of the method of the invention, said method detects RHD positive alleles comprising the following steps:

(a) isolating DNA from a blood sample or blood donor;
(b) hybridizing at least two oppositely oriented primers under stringent conditions to the DNA so as to carry out a PCR;
(c) amplifying the target sequence;
(d) separating the amplification products on a gel; and
(e) analyzing the amplicons.

With regard to specific conditions to be applied in the various steps, it is referred to the corresponding description herein above.

In a preferred embodiment the RHD positive alleles are derived from a serologically RhD negative population. In another preferred embodiment the RhD-negative sample is selected from a Caucasian population.

The method of the invention will result in an amplification of only the target sequence, if said target sequence carries the or at least one mutation. This is because the oligonucleotide will, under preferably stringent hybridization conditions, not hybridize to the wild type sequence (with the consequence that no amplification product is obtained) but only to the mutated sequence. Naturally, primer oligonucleotides hybridizing to one or more as one, such as two mutated sequences may be employed in the method of the invention. The latter embodiment may be favorable in cases where combinations of mutations are tested for. It is important to note that not all or none of said mutations are necessarily missense mutations. This may be true for cases where other types of mutations occur in combination with the above missense mutations or with the above gene conversion.

Preferably, in the method of the invention said amplification or amplification reaction is or is effected by the polymerase chain reaction (PCR). Other amplification methods such as ligase chain reaction may also be employed.

Further, the invention relates to a method for testing for the presence of a protein product of the RHD gene of the invention in a sample comprising assaying a sample obtained from a human for specific binding to the antibody or aptamer or phage of the invention.

Testing for binding may, again, involve the employment of standard techniques such as ELISAs; see, for example, Harlow and Lane, "Antibodies, A Laboratory Manual" CSH Press 1988, Cold Spring Harbor.

In another preferred embodiment the invention relates to a method for testing for the presence of a protein product of the RHD gene encoding the nucleic acid molecular structure or the nucleic acid molecule of the invention, comprising utilizing direct agglutination methods, indirect antiglobulin tests, monoclonal anti-D antibodies and adsorption/elution techniques.

Thus, the embodiment may comprise direct agglutination with two monoclonal anti-D antibodies, alternatively indirect antiglobulin tests using a gel matrix comprising an oligoclonal anti-D antibody, in a further alternative using monoclonal anti-Rhesus antibodies in another alternative adsorption of polyclonal anti-D antibodies to red cells and elution using a chloroform technique. Further description of the methods is given in example 18.

Preferably, in the method of the invention said sample is blood, serum, plasma, fetal tissue, saliva, urine, mucosal tissue, mucus, vaginal tissue, fetal tissue obtained from the vagina, skin, hair, hair follicle or another human tissue.

Furthermore, the method of the invention preferably comprises the step of enrichment of fetal cells. This enrichment may be achieved by using appropriate antibodies, lectins or other reagents specifically binding fetal cells or by any technique attempting the differential separation of maternal and fetal cells, like by density gradients. Also preferably, in said method fetal DNA or mRNA from maternal tissue like peripheral blood, serum or plasma may be extracted, advantageously according to conventional procedures.

In an additional preferred embodiment of the method of the invention, said nucleic acid molecule or proteinaceous material from said sample is fixed to a solid support.

Preferably, said solid support is a chip.

The advantages of chips are well known in the art and need not be discussed herein in detail. These include the small size as well as an easy access of computer based analysis of analytes.

Furthermore, the present invention relates to the use of the nucleic acid molecular structure or the nucleic acid molecule of the invention for the analysis of a negative or a positive Rhesus D phenotype.

The analysis can be effected, for example, on the basis of the methods described herein above.

The invention also relates to the use of the nucleic acid molecular structure or the nucleic acid molecule of the invention, the vector of the invention or the protein product of the RHD gene of the invention for the assessment of the affinity, avidity and/or reactivity of monoclonal anti-D or anti-C antibodies or of polyclonal anti-D or anti-C antisera or of anti-globulin or of anti-human-globulin antisera or of preparations thereof.

Anti-C is a monoclonal antibody or polyclonal antiserum binding to antigen C.

The invention also relates to the use of cells, preferably red blood cells, from probands carrying the nucleic acid molecular structure or the nucleic acid molecule of the invention for the assessment of the affinity, avidity and/or reactivity of monoclonal anti-D or anti-C antibodies or of polyclonal anti-D or anti-C antisera or of anti-globulin or of anti-human-globulin antisera or of preparations thereof.

Said preparations can be provided according to techniques well known in the art. Said preparations may comprise stabilisators such as albumins, further sodium azide, salt ions, buffers etc. The formulation of the preparation may have an influence on the binding characteristics of the antibodies, as is well known in the art.

For example, in a first step, the Rhesus D gene of a carrier or of a blood donor and its allelic status is analyzed and it is determined whether said gene comprises a mutation that was found in accordance with the present invention. In a second step, said mutation is correlated to a certain RhD antigen density on the surface of red blood cells. Conveniently, said correlation can be established by data provided in the present invention (such as mutations per se) and techniques that are well known in the art (see, e.g. Jones et al. 1996, Flegel and Wagner, 1996). In a third step, the features of an antibody or an antiserum such as reactivity, sensitivity, affinity, avidity, and/or specificity are determined with suitable blood group serological techniques preferably using red blood cells that were molecularly and with respect to the RhD antigen surface density characterized as described in step 2. Such data can be used, for example, in quality controls, standardization, etc.

The invention will be most useful for the characterization, standardization and quality control of monoclonal and polyclonal antisera, preferably anti-D monoclonals or antisera. Further, for example, anti-globulin and anti-human-globulin antisera can be characterized on the basis of the teachings of the present invention. An appropriately characterized anti-D monoclonal antibody can be conveniently used in RhD diagnostics. For example, a suitably characterized monoclonal antibody will be useful in determining the D antigen density on the surface of blood cells. Cut-off values for monoclonal antibodies useful in diagnosis can thus be established. This is important for the quality control of antibodies used in RhD diagnosis.

Thus, the invention also relates to a method for the characterization of monoclonal antibodies or polyclonal antisera or of a preparation thereof, said method comprising (a) testing the nucleic acid of sample of a proband for the presence of a breakpoint or mutation as defined in accordance with the invention;
(b) correlating, on the basis of the mutation or deletion status and the allelic status of the RHD gene, the nucleic acid with the density of the protein product of the RHD gene on the surface of red blood cells of said proband;
(c) reacting said monoclonal antibodies or polyclonal antisera or said preparation thereof with a cell carrying the protein product of the RHD gene on its surface;
(d) characterizing said monoclonal antibodies or polyclonal antisera or said preparation thereof on the basis of the results obtained in step (c).

As regards the term “allelic status”, this term describes the possibilities that the RHD alleles in a proband are present in a homozygous, heterozygous or hemizygous state. Also comprised by this term is the possibility that the two alleles carry two different mutations (including the conversion) defined herein above.

In a preferred embodiment of the method of the invention, said characterization comprises the determination of reactivity, sensitivity, avidity, affinity, specificity and/or other characteristics of antibodies and antisera.

Furthermore preferred is a method wherein said cell carrying the protein product of the RHD gene on its surface is a red blood cell.

The invention also relates to a method for determining whether a patient in need of a blood transfusion is to be transfused with RhD negative blood from a donor comprising the step of testing a sample from said patient for the presence of one or more nucleic acid molecular structures or nucleic acid molecules of the invention, wherein a positive testing for two different of said nucleic acid molecular structures or nucleic acid molecules is indicative of the need for a transfusion with Rh negative blood. Alternatively, a positive testing indicating the concomitant presence of two identical copies of one of said nucleic acid molecular structures or nucleic acid molecules is indicative of the need for a transfusion with Rh negative blood.

Alternatively, a negative testing for the presence of the nucleic acid molecular structure or nucleic acid molecule representative of the common RHD negative haplotype with or without a negative testing for one or more nucleic acid molecular structures or nucleic acid molecules representative of the other RHD negative nucleic acid molecular structures or nucleic acid molecules of this invention permits the transfusion of blood that is typed as RhD positive. The invention has important implications for devising a transfusion therapy in humans. For example, it can now be conveniently tested whether the patient actually needs a transfusion with a RhD negative blood or whether such precautions need not be taken.

The invention also relates to a method for determining whether blood of a donor is suitable for transfusion to a patient in need thereof who should not be exposed to antigen C comprising the step of testing a sample from said donor for the presence of the nucleic acid molecular structure of the present invention wherein a positive testing for the nucleic acid molecular structure of the present invention precludes the transfusion of the donor’s blood.

Furthermore, the invention relates to a method for determining whether blood of a donor may be used for transfusion to a patient in need thereof comprising the step of testing a sample from said donor for the presence of one or more of said nucleic acid molecular structures or nucleic acid molecules of the invention, wherein a negative testing for the nucleic acid molecular structures representative of the common RHD negative haplotype with or without a negative testing for one or more nucleic acid molecular structures or nucleic acid molecules representative of the other RHD negative haplotypes of this invention excludes the transfusion the donor’s blood to a patient that is typed as RhD negative.

The invention also relates to a method for determining whether the blood of a donor may be transfused to a patient typed as RhD negative comprising the step of testing a sample from said donor for the presence of one or more nucleic acid molecular structures or nucleic acid molecules of the invention, wherein a positive testing for two different of said nucleic acid molecular structures or nucleic acid molecules is indicative of the possibility to transfuse the donor’s blood to a patient typed as RhD negative.

Alternatively, a positive testing indicating the concomitant presence of two identical copies of one of said nucleic acid molecular structures or nucleic acid molecules is indicative of the possibility to transfuse this donor’s blood to a patient that is typed as RhD negative.

The samples referred to in the above recited methods may be samples that are referred to throughout the specification, such as blood, serum, etc.

As regards the guidelines for transfusing a patient on the basis of any of the above recited methods, the utmost care must be taken that suboptimal transfusion policy is avoided. The risk factor is always to be considered by the physician in charge. In all cases, the potential risk for the patient is to be minimized.

The invention also relates to a method for assessing of the risk of a RhD negative mother of conceiving or carrying an RhD positive fetus or of the risk of a mother having an anti-D titer of conceiving or carrying a fetus at risk to develop hemolytic disease of the newborn comprising assessing a sample obtained from the father of the fetus for the presence of one or more of said nucleic acid molecular structures or nucleic acid molecules of the invention, wherein a negative testing for nucleic acid molecular structures or nucleic acid molecules representative of the common RHD negative haplotype with or without a negative testing for one or more nucleic acid molecular structures or nucleic acid molecules representative of the other RHD negative haplotypes of this invention is indicative for a high risk of conceiving an RhD positive fetus.

In a preferred embodiment of the method of the present invention said nucleic acid molecular structure carries mutations or deletions.

The invention also relates to a method for determining whether the father is RhD negative comprising the step of testing a sample from the father for the presence of one or more nucleic acid molecular structures or nucleic acid molecules of the invention, wherein a positive testing for two different of said nucleic acid molecular structures or nucleic acid molecules is indicative of the father being RhD negative.

Alternatively, a positive testing indicating the concomitant presence of two identical copies of one of said nucleic acid molecular structures or nucleic acid molecules representative of RHD negative haplotypes is indicative of the father being RhD negative.

Furthermore, the invention relates to a method for assessing the possibility or likelihood of a man being the father of a child by assaying a sample obtained from said man for the presence of one or more of said nucleic acid molecular structures or nucleic acid molecules of the invention, wherein the test results are used to determine the homozygosity for, the heterozygosity for or the absence of any nucleic acid molecular structures or nucleic acid molecules representative of the RHD negative haplotype of the present invention used to infer the possibility or likelihood of said man being the father of the child.

The preparation may be a diagnostic or pharmaceutical preparation.

The pharmaceutical composition of the present invention may further comprise a pharmaceutically acceptable carrier and/or diluent. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Furthermore, the pharmaceutical composition of the invention may comprise further agents such as interleukins or interferons depending on the intended use of the pharmaceutical composition.

The invention also relates to a method of treating a pregnant woman being Rhesus D negative wherein the fetus does not carry two nucleic acid molecular structures or nucleic acid molecules of the invention or is not homozygous for any nucleic acid molecular structure or nucleic acid molecule of the invention, comprising administering anti-D to said woman.

Pregnant women may be currently treated with an anti-D prophylaxis, when a Rhesus negative mother carries a RhD positive fetus. The invention allows the discrimination of an anti-D prophylaxis requirement depending on the status of the mother's and/or the fetus' possessing a RhD protein of the invention. One or more of the RhD proteins of the invention may be prone to immunization of their carriers and, hence, would be indicative for the therapy of the mother. Similarly, one or more RhD proteins of the invention, when carried by the fetus, may be known to be of low immunogenicity to the mother and, hence, would be indicative for the omission of anti-D prophylaxis in difference to current clinical therapy.

The administration can be effected by standard routes and doses which can be defined by the attending physician; Mollison, 1993. Preferably, a monoclonal anti-D or combinations/mixtures of monoclonal anti-Ds is/are administered in doses of 50 μg to or exceeding 500 μg anti-D antibody/antisera for intravenous or intramuscular administration (Bowman, 1998). For the quality control of these anti-D antibodies/antisera, the results and methods provided by the present invention may be advantageously employed.

The invention also relates to the use of a phage, aptamer, monoclonal antibody or a polyclonal antisera or a preparation thereof as characterized in the present invention for determination of the protein product of the RHD gene.

In a preferred embodiment of said use, said determination of the protein product of the RHD gene is effected in connection with blood group typing.

Furthermore, the invention relates to a preparation comprising the antibody or aptamer or phage of the invention.

The present invention also relates to a method of identifying an antibody $V_H$ or $V_L$ chain or a combination thereof or an aptamer specifically binding to a protein product of the RHD gene of the invention comprising (a) contacting the protein product of the RHD gene of the invention with a phage library displaying $V_H$ or $V_L$ chains or combinations thereof on the surface of the phage or with aptamers;
(b) identifying phage or aptamers that bind to said protein product of the RHD gene; and optionally
(c) repeating steps (a) and (b) one or more times.

The preparation of phage library and the screening/identification of desired antibody (chains) per se is well known in the art and reviewed, for example, in Winter et al., Annu. Rev. Immunol. 12 (1994), 433-455 and references cited therein. Also, aptamers can be prepared and cloned in phage according to conventional protocols. Whereas single $V_H$ or $V_L$ chains may be identified by the method of the invention as binding to the protein product of the RHD gene of the invention, it is preferred to identify $V_H$-$V_L$ combinations expressed by the phage because this situation resembles the situation of natural antibody binding. By repeating steps (a) and (b) one or more times, better binding specificities may be identified. Protocols for the optimization of binding properties such as affinities, including elution steps for removing bound phage, are well established in the art. For example, once a $V_H$ chain with a convenient binding capacity has been found, $V_L$ chains may be identified that significantly improve the binding capacity of the antibody, e.g. by replacing the $V_L$ chain that was associated with the $V_H$ chain in the first selection step with a more suitable $V_L$ chain.

The invention also relates to a method of identifying a monoclonal antibody specifically binding to a protein product of the RHD gene of the invention comprising (a) contacting the protein product of the RHD gene of the invention with one or more monoclonal antibodies;
(b) identifying monoclonal antibodies that bind to said protein product of the RHD gene; and optionally
(c) repeating steps (a) and (b) one or more times.

The invention also relates to a method of identifying an antibody $V_H$ or $V_L$ chain or a combination thereof or an aptamer specifically binding to a protein product of the RHD gene of the invention comprising (aa) contacting said protein product of the RHD gene and
(ab) a normal D polypeptide
  wherein the normal D polypeptide is present in a molar mass that is higher, equal or less than the protein product of the RHD gene of (aa) with a phage library displaying $V_H$ or $V_L$ chains or combinations thereof on the surface of the phage or with aptamers;
(b) identifying phage or aptamers that bind to said protein product of the RHD gene of (a); and optionally
(c) repeating steps (a) and (b) one or more times.

Particularly preferred in step (ab) is that the molar mass of the normal D polypeptide is higher than that of the protein product of the RHD gene of (aa).

In the case that only one round of selection is employed for the identification (i.e. when step (c) does not apply), it is preferred that the number of protein product of the RHD gene of (aa) is in molar excess over the number of phage particles. The preferred embodiments of the method of identifying an antibody $V_H$ or $V_L$ chain or of a combination thereof or of an aptamer described hereinbefore equally apply to this embodiment of the invention.

The invention also relates to a method of identifying a monoclonal antibody specifically binding to a protein product of the RHD gene of the invention comprising (aa) contacting the protein product of the RHD gene and
(ab) a normal D polypeptide
  wherein the normal D polypeptide is present in a molar mass that is higher, equal or less than the protein product of the RHD gene of (aa) with one or more monoclonal antibodies;
(b) identifying monoclonal antibodies that bind to said protein product of the RHD gene of (aa); and optionally
(c) repeating steps (a) and (b) one or more times.

Preferably, the protein product of the RHD gene is exposed on the surface of a cell. An appropriate surface is the surface of an erythrocyte. However, other host cells may be transfected with a vector suitable for expression of the protein product of the RHD gene of the invention and express the same on their surface. Antibodies may also bind to recombinant proteins of or parts of proteins of D antigen and purified proteins.

It is further preferred that the polypeptide or host cell is affixed to a solid support. Suitable examples for solid supports are microtiter plates or beads.

In an additionally preferred antibody, subsequent to step (b) or (c), the following step is carried out:

(d) identifying the amino acid sequence of the $V_H$ or $V_L$ chains and/or identifying the nucleic acid sequences encoding said amino acid sequence.

The identification of the amino acid/nucleic acid sequences can be effected according to conventional protocols; see, e.g., Sambrook et al., loc. cit.

Hence and in summary, the present invention provides means and methods for the detection of RHD haplotypes, comprising common RHD negative haplotypes, as described above, as well as presumably rare RHD positive alleles in serologically RhD negative populations. Latter alleles, harbouring RHD sequences and therefore determined as RHD-positive, can comprise either RHD/RHCE hybrid genes, stop codons, splice site mutations or gene deletions, that terminate or reduce the RhD antigen expression. Carrying out the improved detection methods of the invention, it was surprisingly found, that several samples, determined as RhD negative in routine serology, could be identified having RHD positive alleles. Furthermore, some of those samples were even RhD antigen positive when performing a detection assay based on adsorption and elution, indicating that the molecular basis for the RHD positive alleles in RhD negatives is more heterogenous than anticipated. Advantageously, the disclosure content of the present invention now provides new and practicable nucleic acid amplification techniques to determine whether RHD specific sequences cause RhD positive or RhD negative phenotypes.

In a particularly preferred embodiment the method of present invention, wherein, in the case that only one round of selection is employed for the identification, the number of protein molecules of the RHD gene of (a) is in molar excess over the number of phage particles.

Moreover, the present invention relates to the use of cells, preferably red blood cells comprising the protein product of the RHD gene of the present invention or produced by the method of the present invention, from probands for the assessment of the affinity, avidity and/or reactivity of monoclonal anti-D or anti-C antibodies of the present invention or of polyclonal anti-D or anti-C antisera or of anti-globulin or of anti-human-globulin antisera or of preparations thereof.

Furthermore, the invention relates to the use of SMP1 polymorphisms to determine specific RH(RHD-RHCE)-haplotypes genetically linked to said polymorphisms.

Basis for this embodiment of the present invention is provided by the unique structure of the RH locus comprising three genes: RHD, RHCE, and SMP1. The nucleotide sequence of the latter gene has been deposited in the Genbank as putative member of an 18 kDa small membrane protein family. Its function is as yet unknown. It shows homology to an open reading frame on chromosome 21 (Reboul, Genome res. 9:242, 1999). Its position between both RH genes implies that any polymorphism of the SMP1 gene would be tightly linked to a specific RH haplotype, and it might be anticipated that functionally relevant mutations of the SMP1 gene may cause selection pressure for or against specific RH haplotypes. Such factors might explain some previously unresolved issues of RH haplotype distribution, like the high frequency of RH negatives in Europe. Screening for polymorphisms in SMP1 is therefore of high interest for the understanding of the RH locus as well as for diagnostic applications thereof.

According to the present invention the term "polymorphism" relates to the existence in a population of more than one genetic structure or a gene of a haplotype or of a DNA segment. Nevertheless, sometimes such a genetic polymorphism does not always result in a differing phenotype, but may only be detected at the genetic level.

In another preferred embodiment the invention relates to a method to detect specific RH(RHD-RHCE)-haplotypes comprising the determination of SMP1-polymorphisms in the SPM1 gene by utilizing any structural feature or nucleotide sequence or both of the RH locus or combinations thereof with techniques known in the art, preferably by PCR-RFLP, PCR-SSP or long-range PCR.

Furthermore, the invention relates to a kit comprising (a) the oligonucleotide of the invention; and/or
(b) the antibody of the invention;
(c) the aptamer of the invention; and/or
(d) the phage of the invention;
(e) a pair of primers useful for carrying out the amplification reaction of the invention.

Parts of the kit can be packaged individually in vials or in combination in containers or multicontainer units. The kit of the present invention may be advantageously used for carrying out the method of the invention and could be, inter alia, employed in a variety of applications referred to above. The manufacture of the kits follows preferably standard procedures which are known to people skilled in the art.

The present invention also relates to a process to determine the presence of an antigen C encoded by a RHD gene comprising the step of detecting any of the breakpoint regions mentioned in the present invention.

Finally, the invention relates to a process to determine the presence of an antigen C comprising the steps of the processes of the present invention.

The disclosure content of the documents as cited in this specification is herewith incorporated by reference.

The figures show

FIG. 1 Schematic structure of the RH gene locus. The positions and orientations of the genes and the Rhesus boxes are indicated by open arrows and triangles, respectively (Panel A). The exons are shown as vertical bars and their exon number is indicated. The two RH genes have opposite orientation, face each other with their 3' ends, and are separated by about 30,000 bp. A third gene, SMP1, has the same orientation as RHD and is positioned in between RHD and RHCE. The RHD gene is flanked on both sides by the two highly homologous Rhesus boxes (b). All exons are shorter than 200 bp with the exception of the RHD and SMP1 3' terminal exons. Data used to establish this structure (Panel B) include the extension of genomic sequences represented in the cDNAs (horizontal arrows), identities and homologies to genomic clones (bar a: identity with dJ465N24; b: homology of RHD to dJ469D22; c: homology of RHD 3' part to dJ465N24; d: identity with dJ469D22). The positions of three bridging PCR reactions are indicated. The correct position of a nucleotide stretch previously reported by Okuda et al. (Okuda, Biochem. Biophys. Res. Commun. 263:378, 1999) as "spacer" sequence between RHD and RHCE is indicated by the bar labeled s.

Figure 2:
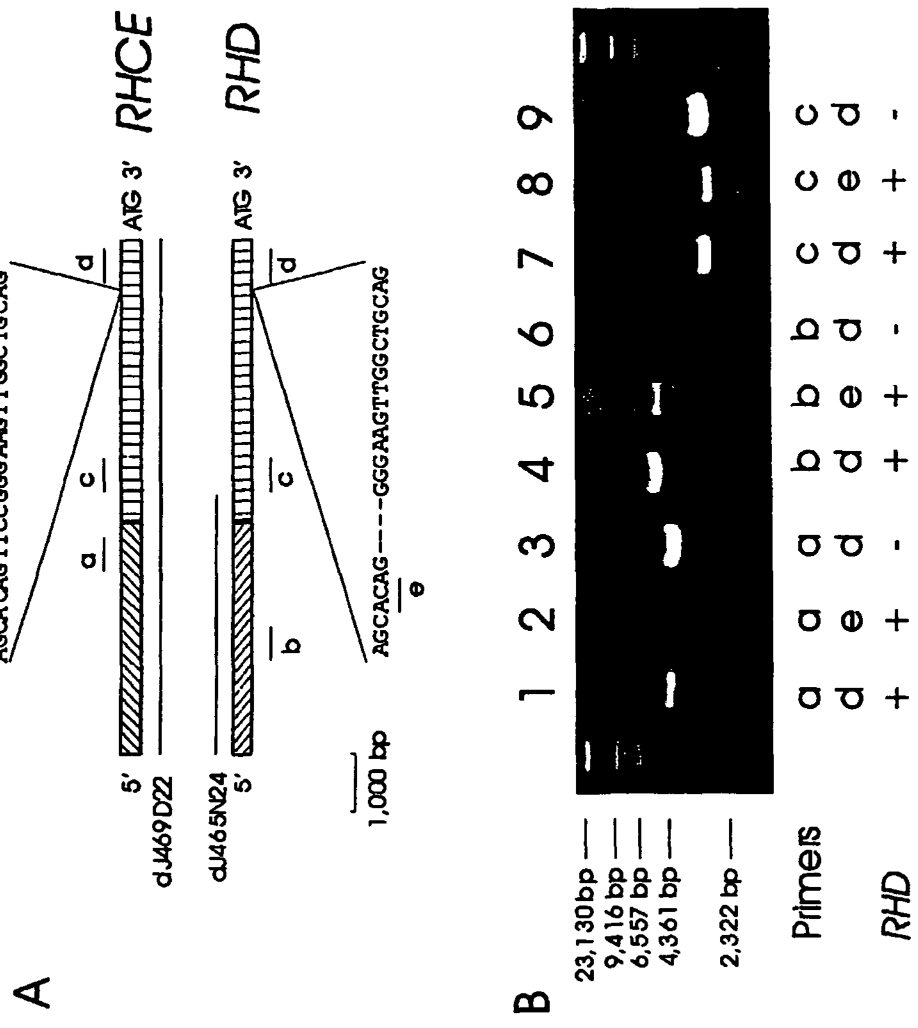

FIG. 2 Chromosomal organization of the DNA regions located 5' to the RHD and RHCE genes. The proposed structure of the RHCE and RHD 5' flanking regions is depicted (Panel A). A total of 4,941 bp immediately 5' of the ATG start codons are homologous between the RHCE and RHD genes (vertically hatched bars). No homology is present further beyond this homology region (diagonally hatched bars). Two genomic clones, dJ469D22 and dJ465N24, were utilized for primer design. DJ469D22 comprises the full length of the depicted RHCE region, whereas dJ465N24 extends only 466 bp into the homology region. The positions of several PCR primers are indicated (a, rey14a; b, rend32; c, rey15a; d, re014; e, re011d). This proposed structure is supported by several PCR reactions (panel B). Forward priming was done with primer a (RHCE specific, lane 1-3), primer b (RHD specific, lane 4-6), and primer c (RHCE and RHD homology region, lane 7-9). Amplicons were lacking for primer a with RHD specific reverse primer e (lane 2) and for primer b with RHD negative DNA (lane 6). The other seven PCR reactions yielded amplicons of the predicted sizes in accordance with the genomic structure shown in panel A. (SEQ ID NOs.:113-114)

FIG. 3 Chromosomal organization of the SMP1 gene. The SMP1 gene has seven exons. The positions and approximate sizes of the introns are shown. The start of the published cDNA (GenBank accession number AF081282) is separated by 15 nucleotides from the downstream Rhesus box. Exon 1 contains only 5' untranslated sequence, the SMP1 start codon is located in exon 2. Exon 7 contains 16 codons and 1,656 bp 3' untranslated sequences and is contiguous with the 3' untranslated sequence of RHCE exon 10. (SEQ ID NOs.:1-14)

FIG. 4 Chromosomal organization of the Rhesus boxes. The physical extension of the upstream Rhesus box (5' to RHD) is 9,145 bp (black bar). About 63% of the boxes' nucleotide sequence consists of repetitive DNA; the types of the repeat families are indicated. The overall homology between the upstream and downstream Rhesus box is 98.6%, but within an 1,463 bp identity region (horizontal arrows), there is only a single 4 bp insertion (double vertical line). A CpG-island (double-headed arrow) is located at the 3' end and is in the downstream Rhesus box (3' to RHD) adjacent to the SMP1 promoter.

FIG. 5 RHD gene deletion in the Rh negative haplotypes. Three 3,100 bp segments of the Rhesus boxes are shown. The upper line indicates the nucleotide sequence of the upstream Rhesus box in D-positives, the lower line the nucleotide sequence of the downstream Rhesus box in D-positives. The middle line gives the nucleotide sequence of the single Rhesus box carried by Rh negatives. Asterisks denote identical nucleotides. The RHD deletion occurred in a 903 bp segment of absolute identity that was part of a 1,463 bp identity region. The positions of primers rez7 and rnb31 is shown (m indicates mismatch). PstI restriction sites are indicated by carets (^). The three Rhesus boxes are deposited at EMBL under accession numbers AJ252311 (upstream Rhesus box), AJ252312 (downstream Rhesus box), and AJ252313 (hybrid Rhesus box). (SEQ ID NOs.:15-17)

Figure 6:
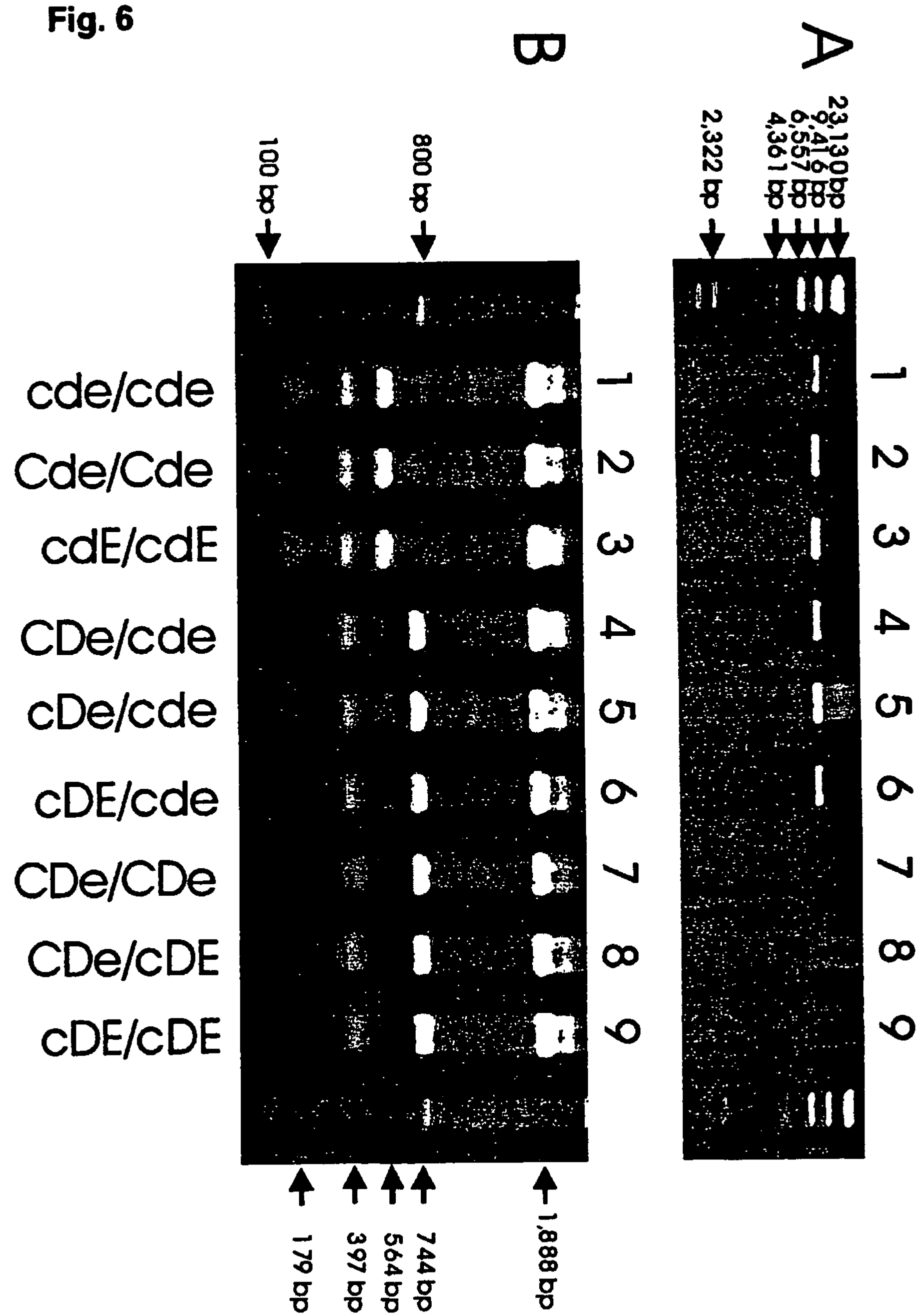

FIG. 6 Two technical procedures for specific detection of the RHD deletion in the common RHD negative haplotypes. A long-range PCR amplification with primers located in non-Rhesus box sequences (Panel A) and PCR-RFLP with primers located in the Rhesus boxes are shown (Panel B). The deduced genotypes are indicated. The primers of the long-range PCR were located 5' of the upstream Rhesus box (primer rez4) and in SMP1 exon 1 (primer sr9). RHD negative haplotypes were detected specifically (Panel A, lane 1-6). DNA homozygous for the RHD gene was negative, because the PCR cannot amplify the 70,000 bp DNA stretch of the RHD gene. For the PCR-RFLP method, the PCR amplicons (primer rez7 and rnb31) were digested with PstI. In D-negatives, there are three PstI sites in the amplicon (see FIG. 5) resulting in fragments of 1,888 bp, 564 bp, 397 bp, and 179 bp (lane 1 to 3). The downstream Rhesus box of D-positives lacks one PstI-site resulting in fragments of 1,888 bp, 744 bp, and 397 bp (lane 7 to 9). $RHD^{+}/RHD^{-}$ heterozygotes show both fragments of 744 and 564 bp (lane 4 to 6). The 564 bp fragment appears weaker because heterodimers are not cut by PstI. Primer rnb31 does not amplify the upstream Rhesus box of D-positives.

FIG. 7 Model of the proposed mechanism causing the prevalent RHD negative haplotypes in whites. The physical structure of the RHD and RHCE gene locus is depicted (panel A). An unequal crossing over between the upstream and downstream Rhesus boxes can be triggered by their high homology (panel B). The breakpoint region in the Rhesus boxes was found to be of 100% homology for 903 bp (see FIG. 5). Resolving the crossed over chromosome yields the RH gene structure of the extant RHD negative haplotype (panel C).

FIG. 8 DNA sequence of the hybrid Rhesus box of RHD negatives. (SEQ ID NO.:18)

FIG. 9 DNA sequence of the upstream Rhesus box of D-positives. (SEQ ID NO.:19)

FIG. 10 DNA sequence of the downstream Rhesus box of D-positives. (SEQ ID NO.:20)

FIG. 11 DNA sequence of the RHD promoter. The last three nucleotides represent codon 1 of the RHD gene. (SEQ ID NO.:21)

FIG. 12. $Cde^s$ breakpoint region in RHD intron 3. The nucleotide sequence of a part of the intron 3 of $Cde^s$, RHD and RHCE 2,938 to 3,636 bp 3' of the exon 3/intron 3 junction is shown. The human DNA sequence from clone RP3-469D22 on chromosome 1p35.1-36.13 containing the 5' part of the gene for RHCE (GenBank accession number AL031284) was taken as reference; numbers indicate the position in this sequence relative to the first base of intron 3 in the RHCE gene. The corresponding RHD gene sequence derives from GenBank accession number AL139426. Nucleotides indicating RHD or RHCE origin of the $Cde^s$ sequences are highlighted. A 154 bp DNA stretch comprising the breakpoint region of $Cde^s$ is indicated by asterisks. (SEQ ID NOs.:22-24)

FIG. 13. $Cde^s$ breakpoint region in RHD intron 7. The nucleotide sequence of a part of the intron 7 of $Cde^s$, RHD and RHCE about 2,726 to 3,719 3' of the exon 7/intron 7 junction is shown. The human DNA sequence from clone RP3-469D22 on chromosome 1p35.1-36.13 containing the 5' part of the gene for RHCE (GenBank accession number AL031284) was taken as reference; numbers indicate the position in this sequence relative to the first base of intron 7 in the RHCE gene. The corresponding RHD gene sequence derives from GenBank accession number AL139426. Nucleotides indicating RHD or RHCE origin of the $Cde^s$ sequences are highlighted. A 666 bp DNA stretch comprising the breakpoint region of $Cde^s$ is indicated by asterisks. (SEQ ID NOs.: 25-27)

Figure 14:
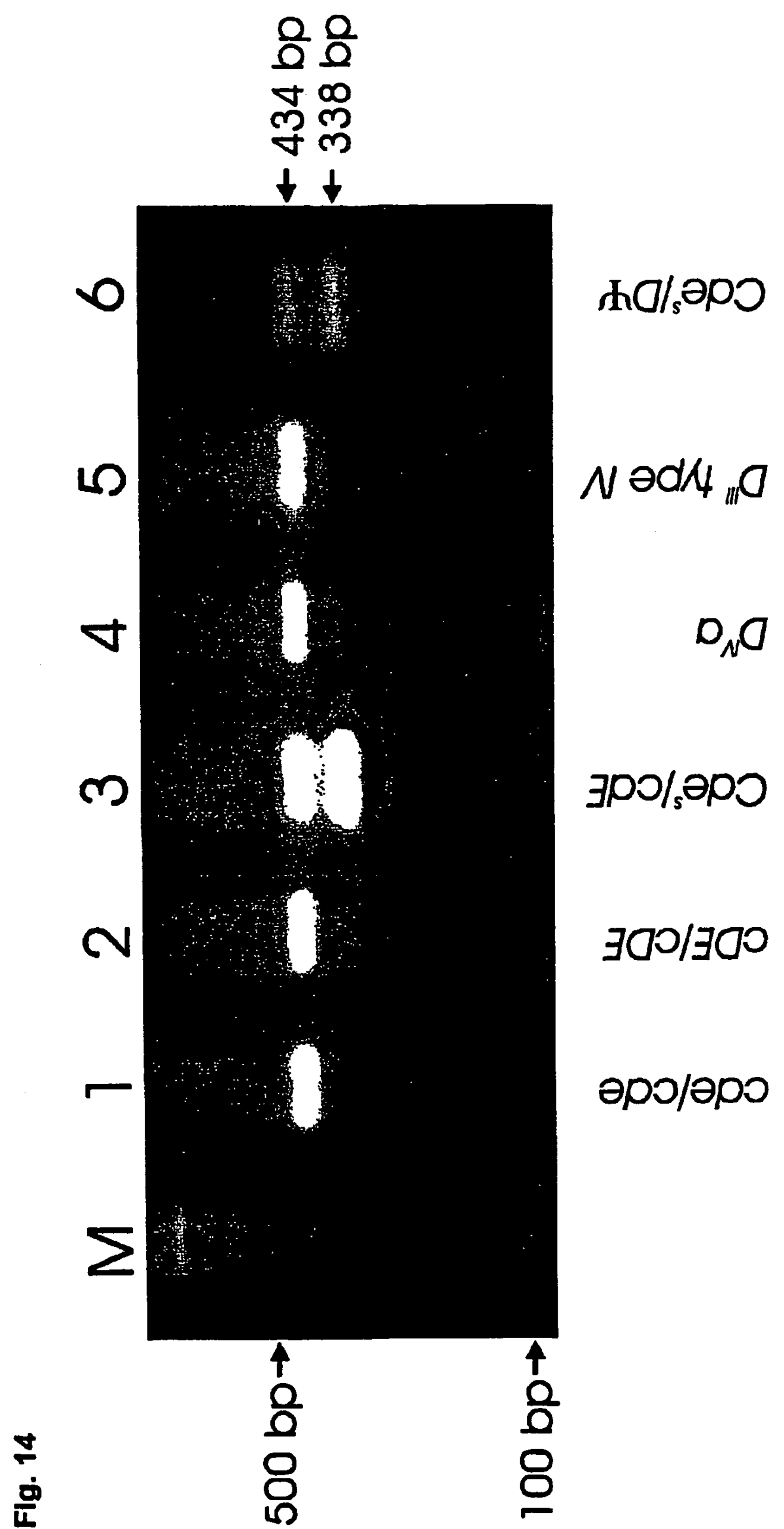

FIG. 14. Specific detection of $Cde^s$ by PCR-SSP. A PCR-SSP detecting the 3' breakpoint region of $Cde^s$ in intron 7 is shown. Both, a RHD negative sample (lane 1, ccddee) and a normal RHD positive sample (lane 2, ccD.EE) yield the 434 bp control product only, which is derived from the HGH gene. In contrast, a $Cde^s$ sample (CcddEe, lane 3) yields the 338 bp specific product, which is derived from the breakpoint region in intron 7, and in addition the 434 bp control fragment. This reaction is specific for $Cde^s$; the two partial D phenotypes $D^{IVa}$ (lane 4) and $D^{III}$ type IV (lane 5) do not yield a specific product. The reaction also detects $Cde^s$ specifically, if $Cde^s$ occurs in trans to other RHD alleles, like in a RHDΨ/$Cde^s$ sample (lane 6).

Figure 15:
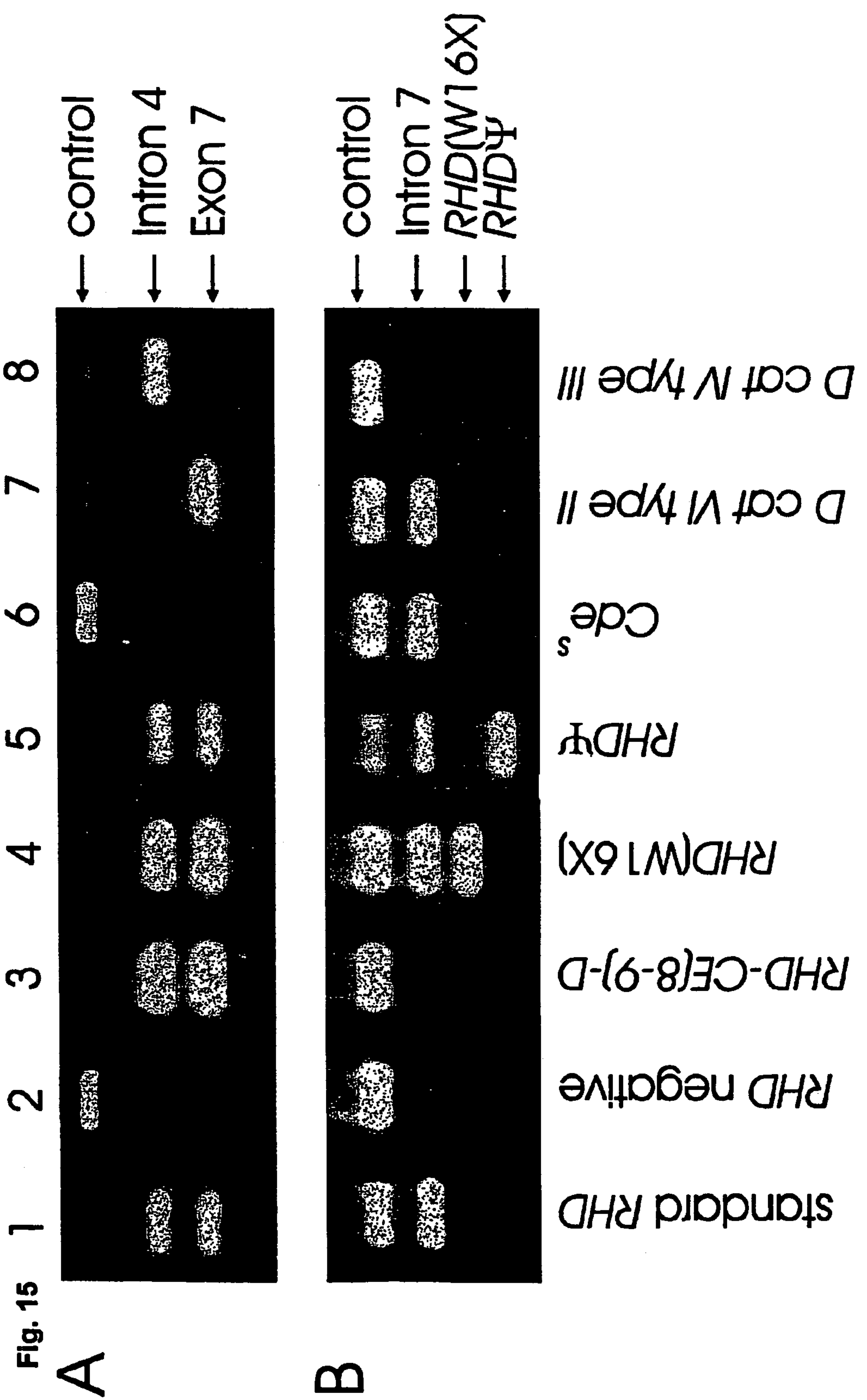

FIG. 15. RHD PCR-SSP for routine DNA typing. The PCR is performed as a modular system consisting of two multiplex reactions, an intron 4/exon 7 multiplex PCR-SSP (Panel A) and an intron 7 PCR enhanced by specific detection of RHD (W16X) and RHDΨ (Panel B). Results are shown for a normal D positive sample (lane 1), a normal D negative sample (lane 2), several rare D negative samples (lanes 3 to 6) and major D positive RHD variants (lanes 7 and 8). Standard D positive and D negative samples and D categories IV and VI are recognized in reaction A. RHD-CE(8-9)-D is detected in reaction B by the absence of the intron 7 band. The presence of RHD(W16X) and RHDΨ is also detected in reaction B. Band size is Panel A, control, 434 bp (HGH gene); intron 4, 226 bp; exon 7, 123 bp; Panel B, control, 659 bp (chromosome 1 genomic sequence about 90,000 bp 5' of Rhesus box); intron 7, 390 bp; RHD(W16X), 248 bp; RHDΨ, 154 bp. The internal control amplicons, which were devised to be larger than the specific amplicons, may be suppressed because of competition, if a specific product is amplified.

The examples illustrate the invention:

Example 1

Blood Samples and DNA Isolation

EDTA- or citrate-anticoagulated blood samples were collected from white blood donors and characterized as D negative in routine typing including an antiglobulin test with anti-D (Wissenschaftlicher Beirat der Bundesärztekammer; Paul-Ehrlich-Institut. Richtlinien zur Blutgruppenbestimmung and Bluttransfusion (Hämotherapie). Köln: Deutscher Ärzte-Verlag; 1996; Wagner, Infusionsther Transfusionsmed 22:285-90, 1995). If necessary, samples were collected at random for specific CcEe phenotypes. A total of 314 ccddee, 433 Ccddee, 271 ccddEe, 19 CcddEe, 24 CCddee, 1 CcddEE and 6 ccddEE samples were tested. DNA was isolated by a modified salting-out procedure as described in Gassner et al., Transfusion 37; 1020, 1997.

Example 2

Molecular Work-Up

All samples were tested by PCR-SSP for the presence of four different RHD specific polymorphisms located in the RHD promoter, intron 4, exon 7 and the 3' untranslated region of exon 10. 48 samples with at least one positive PCR reaction were detected (Table 5). Those samples were further investigated for the presence of RHD specific polymorphisms in exon 3, exon 4, exon 5, exon 6, exon 7, intron 7 and exon 9. Twenty-six samples showed one of eight distinct PCR patterns involving a mixture of positive and negative reactions (Table 6). Twenty-two samples were positive for all RHD specific polymorphisms investigated and were assigned to eight RHD alleles by RHD specific sequencing of the ten RHD exons from genomic DNA (Table 7). For each PCR pattern and each RHD allele, one sample was serologically investigated. The phenotypes were determined to represent weak D, partial D, and $D_{el}$, or confirmed as serologically D negative by adsorption/elution (Table 6 and 7).

Example 3

DNA Database Searches and Analysis

The GenBank and the chromosome 1 database of the Sanger Center were searched with cDNA sequences representative of RHD (RhXIII, accession number X63097) and RHCE (RhVI, X63095) using the BLAST program. The 84,810 bp genomic clone dJ469D22 (GenBank accession number AL031284), the 129,747 bp genomic clone dJ465N24 (GenBank accession number AL031432) and the 2,234 bp SMP1 cDNA (GenBank accession number AF081282) were identified. dJ469D22 represented a major fragment of the RHCE gene, starting 33,340 bp 5' of the RHCE start codon and ending 1,142 bp 3' of exon 9. In dJ465N24, an internal stretch of 1,418 bp located between position 120,158 and 121,568 was 96% homologous to the 3' end of the RHD cDNA. The 3' end of the SMP1 cDNA was complementary to the 3' end of the RHCE cDNA with an overlap of 58 bp.

Example 4

PCR

If not mentioned otherwise, PCR reactions were done with 60° C. annealing, 10 min extension at 68° C. and denaturation at 92° C. using the expand long template or the expand high fidelity PCR systems (Boehringer Mannheim, Mannheim, Germany) and the listed primers (Table 1). Three PCR reactions were used to bridge gaps in the 3' flanking regions of the RH genes. PCR 1 was done using primers rea7 and rend31 (PCR 2, rend32, sf1c; PCR 3, rea7, sf3). The structure of the 5' flanking regions was confirmed with PCR amplifications involving sense primers rend32, rey14a, rey15a and antisense primers re011d and re014. Intron 9 size was estimated to be about 9,000 bp based on PCR amplifications using rb10b and rr4 for RHD (re96 and rh7 for RHCE).

Example 5

Nucleotide Sequencing

Nucleotide sequencing was performed with a DNA sequencing unit (Prism BigDye terminator cycle-sequencing ready reaction kit; ABI 373A, Applied Biosystems, Weiterstadt, Germany).

Example 6

Characterizing the RH Gene Locus

A physical structure of the RH genes' locus was derived (FIG. 1). This structure was deduced from the following considerations: (i) 3' flanking regions. The 3' flanking region of RHD was highly homologous to the 3' part of dJ465N24 (FIG. 1B, region c). This homology continued beyond the end of the RHD cDNA and extended for at least 8,000 bp as proven by the fact that it was possible to obtain PCR amplicons (FIG. 1B, PCR 1). Sequences homologous to the 3' part of dJ465N24 were neighboring to the 5' region of the SMP1 gene (FIG. 1B; PCR 2). The 3' end of the SMP1 gene occurred immediately adjacent to the RHCE gene as indicated by the complementarity of the 3' ends of the respective cDNAs and confirmed by PCR (FIG. 1B, PCR 3). Further details of the RHD 3' flanking region (Rhesus box) and the SMP1 gene are described below. (ii) 5' flanking regions. dJ469D22 comprised 33,340 bp 5' flanking region of RHCE. For RHD, a 466 bp homology between the 3' end of dJ465N24 and dJ469D22 indicated that dJ465N24 might represent the 5' flanking sequence of RHD. This assumption was proven by PCR (FIG. 2). (iii) Analysis of YAC 38A-A10. DNA from the YAC 38A-A10 (UK HGMP resource centre, Cambridge, UK) was isolated after a single growth phase by standard methods. It was confirmed that this YAC contained RH DNA. Furthermore, shotgun cloning experiments indicated that some of its insert probably derived from the X chromosome (data not shown). This YAC had been known to contain RHCE exons 2 to 10 and RHD exons 1 to 10 (Carritt, Hum. Mol. Genet. 6:843, 1997) and was thus expected to contain the DNA segments interspersed between RHD and RHCE. The presence of DNA segments representative of different parts of the RH locus in this YAC was observed (Table 2). The results were concordant with the proposed structure of the RH locus shown in FIG. 1, Panel A.

Example 7

Identification of RHD Specific Sequences in the RHD Promoter

About 2,000 bp RHD promoter sequence was established by chromosomal walking (GenomeWalker kit, Clontech, Heidelberg, Germany). D-positive and D-negative samples were amplified using primers re04 and re11d (Table 1) and RHD- and RHCE-specific sequences established for 1,200 bp 5' of the start codon by sequencing with internal primers. A short deletion in the RHD gene was identified and used to develop the RHD-specific primer re011d. The 1,200 bp sequence including the RHD promoter has been deposited at EMBL under accession no. AJ252314.

Example 8

Characterization of Rhesus Boxes

Two DNA segments of about 9,000 bp, located 5' and 3' of the RHD gene, were highly homologous, had identical orientation, and were designated "Rhesus boxes" (FIG. 4). The Rhesus boxes were amplified and sequenced using internal primers in two overlapping fragments using PCR primer pairs rez4/rend31 and rend32/re011d (upstream Rhesus box), rea7/rend31 and rend32/sr9 (downstream Rhesus box), and rez4/rend31 and rend32/sr9 (hybrid Rhesus box of RHD-negative). The upstream Rhesus box (5' of RHD) was about 9,142 bp long and ended about 4,900 bp 5' of the RHD start codon. The downstream Rhesus box (3' of RHD) was 9,145 bp long and started 104 bp after the RHD stop codon. The Rhesus boxes exactly embraced the part of RHD with homology to RHCE. The central portion of both Rhesus boxes contained an almost complete remnant of a transposon-like human element (THE-1B). The single open reading frame usually found in the THE-1B element was, however, abolished due to several nucleotide aberrations occurring in both Rhesus boxes in parallel, including a nonsense mutation in codon 4. While there was overall 98.6% homology between both Rhesus boxes, a 1,463 bp "identity region" located between positions 5,701 and 7,163 was completely identical with the single exception of a 4 bp T insertion in a poly T tract.

Example 9

Evaluation of the Genomic Structure of SMP1

The genomic structure of the SMP1 gene was evaluated by PCR using internal primers and nucleotide sequencing (FIG. 3). The sizes of the SMP1 introns were estimated by PCR amplicons obtained with primers rend32, sr9, sf1c, sf1, sm19, sr45, sr47, sr47c, sr5, sr5c, sr55, sr55c, sr3, sr3 kp, rea7. The positions of the intron/exon junctions and the absence of additional introns were determined by nucleotide sequencing. Six introns could be identified. Exon 1 contained 5' untranslated sequences only and was separated from the Rhesus box by 15 bp. The long 3' untranslated sequence of exon 7 overlapped with RHCE exon 10. The total gene size was estimated to be 20,000 bp resulting, in conjunction with the downstream Rhesus box, in a distance between RHD and RHCE of about 30,000 bp (FIG. 1).

Example 10

Localization of the RHD Gene Deletion in the RHD Negative Haplotypes

It was reasoned that the homology of the two Rhesus boxes may have been instrumental for the mechanism of the RHD deletion in the common RHD negative haplotypes. The nucleotide sequence of the Rhesus box in RHD negative DNA was determined (FIG. 5). The single Rhesus box detected in RHD negatives had a hybrid structure. The 5' end of this Rhesus box represented a upstream Rhesus box, the 3' end a downstream Rhesus box. It was determined that the 903 bp breakpoint region of the RHD deletion was located in the identity region of the Rhesus boxes (FIG. 4, arrow pointing to left).

Example 11

Specific Detection of the RHD Deletion by PCR

Two PCR based methods were developed for specific detection of the RHD gene deletion occurring in the prevalent RHD negative haplotypes (FIG. 6). Long-range PCR-SSP was performed using the expand long template PCR system with buffer 3 and primers rez4 (5' of upstream Rhesus box) and sr9 (SMP1 exon 1). Annealing was at 60° C. and extension 20 min at 68° C. PCR amplicons were resolved using a 1% agarose gel. PCR-RFLP was performed using the expand high fidelity PCR system and primers rez7 (non-specific, 5' of Rhesus box identity region) and rnb31 (specific for downstream Rhesus box, 3' of Rhesus box identity region). Annealing was at 65° C. and extension 10 min at 68° C. PCR amplicons were digested with PstI for 3 hrs at 37° C. and fragments resolved using a 1% agarose gel.

These techniques allowed the ready and direct detection of the common RHD negative haplotypes, even if they are in trans to RHD positive haplotypes. PCR-RFLP was further applied to a larger number of samples (Table 3). As expected, all 33 samples with known genotype were correctly typed. In 68 additional samples representative of the most common phenotypes, the results were consistent with the known haplotype frequencies in the population.

Example 12

RHD PCR-SSP

The PCR-SSP reactions (Table 4) were adapted and extended from a previously described RHD exon specific PCR-SSP method (Gassner, Transfusion 37:1020-6, 1997) and were triggered to work under identical thermocycling conditions. Concentrations of specific primers were 0.2 μM for all reactions with the exception of exon 6 (0.1 μM), intron 7 (0.4 μM) and exon 9 (0.4 μM). For most samples intron 4/exon 7 was tested as multiplex reaction containing 0.2 μM of exon 7 (primer set ga71/ga72) and 0.1 μM of intron 4 primers. Each reaction contained a set of HGH primers (Gassner, Transfusion 37:1020-6, 1997) as an internal control in concentrations of 0.05 μM for promoter, intron 4, and exon 7 with ga71/ga72; 0.075 μM for exon 10; 0.1 μM for intron 7; 0.15 μM for exon 3, exon 4, exon 7 with rb26/re71, and exon 9; 0.2 μM for exon 5 and exon 6. $Mg^{2+}$ concentration was 0.4 μM for intron 7 and for all other reactions 0.15 μM. For exon 6, 20% solution Q (Qiagen, Hilden, Germany) was added.

Example 13

Improved RHD PCR-SSP for Routine DNA Typing

Based on the alleles detected in this study and described previously, we devised an improved RHD PCR-SSP for routine DNA typing that included the specific detection of RHDΨ and alleles detected in this study, like RHD(W16X) in a single PCR tube. Reaction A contained primers ga71 and ga72 at 0.3 μM, rb12 and re41 at 0.1 μM, and HGH primers at 0.1 μM. Mg2+ was at 0.175 μM. Reaction B contained primers RhPsiF and RhPsiB at 0.5 μM, re11d and RhX1f1 at 0.3 μM, re721 and rb9 at 0.2 μM and as control primers rend9b1 and rend 9b2 at 0.2 μM. Primer sequences were ga71, gttgtaaccgagtgctggggattc (SEQ ID NO.:67); ga72, tgccggctccgacggtatc (SEQ ID NO.:68); rb12, tcctgaacctgctctgtgaagtgc (SEQ ID NO.:69); re41, cgatacccagtttgtctgccatgc (SEQ ID NO.:70); RhPsiF, agacagactaccacatgaacttac (SEQ ID NO.: 71); RhPsiB, tctgatctttatcctccgttccctc (SEQ ID NO.:72); re11d, agaagatgggggaatctttttcct (SEQ ID NO.:32); RhX1f1, cgctgcctgcccctctga (SEQ ID NO.:73); re721, ctggaggctctgagaggttgag (SEQ ID NO.:74); rb9, aagctgagttccccaatgctgagg (SEQ ID NO.:75); rend9b1, cactgcacttggcaccattgag (SEQ ID NO.:76); rend9b2, ttccgaaggctgcttttccc (SEQ ID NO.:77).

The PCR reactions could be performed in two tubes (FIG. 15), tested five polymorphisms and were expected to have a false-positive rate of less than 1:10,000 (Table 11).

Example 14

PCR Reactions for $Cde^s$

A hybrid exon 3 with a N152T substitution occurring in the $Cde^s$ haplotype was detected by a PCR-SSP reaction using specific primers Rh152Tb and ga31 at 0.3 μM. The L245V substitution observed in $Cde^s$ was detected with specific primers Rh223Vf and Rh245Vb at 0.2 μM. HGH primer concentrations were 0.1 μM. The other PCR conditions were identical as described in the previous paragraph. Primers sequences were Rh152Tb, gatattactgatgaccatcctcatgg (SEQ ID NO.:78); Rh223Vf, ttgtggatgttctggccaagtg (SEQ ID NO.: 79); and Rh245Vb, gctgtcaccactctgactgctac (SEQ ID NO.: 80). The $Cde^s$ haplotype, that is frequent in Africans (Faas, Transfusion 37:38-44, 1997; Singleton, Blood 95:12-8, 2000), possesses a hybrid exon 3 harboring the RHCE specific N152T substitution (Faas, Transfusion 37:38-44, 1997). This hybrid exon is expected to be typed as RHD positive by the RHD exon 3 specific PCR that detected an A at position 383 (codon 128) and was used in the population survey. Since pattern 4 and pattern 8 were compatible with the known data about the $Cde^s$ haplotype, the presence of a hybrid exon 3 was evaluated in the two samples by sequencing the 3' part of exon 3 and by a PCR-SSP specific for an exon 3 hybrid indicative of $Cde^s$. The pattern 4 sample possessed a normal RHD exon 3, while the pattern 8 sample had a hybrid exon 3 as predicted for a $Cde^s$ haplotype. Also, the T at position 410 (A137V substitution) typical for the $Cde^s$ haplotype (Daniels, Transfusion 38:951-8, 1998) and also present in D category III type IV was detected. The identity of pattern 8 and $Cde^s$ was further corroborated by a PCR-SSP detecting G at position 733 (L245V substitution).

Example 15

5' Breakpoint Region of Cde$^s$ in Intron 3

Based on its cDNA, Cde$^s$ had been characterized as an RHD-CE(3-7)-D hybrid gene, in which the 5' part of exon 3 derived from RHD and the 3' part of exon 3 including codon 152 derived from RHCE. We noted that a similar hybrid exon 3 with a N152T substitution was found in D category III type IV (Wagner, F. F., Frohmajer, A., Ladewig, B., Eicher, N. I., Lonicer, C. B., Müller, T. H., Siegel, M. H., and Flegel, W. A. Weak D alleles express distinct phenotypes. *Blood* 95:2699-2708, 2000) and in D category IVa (Rouillac, C., Colin, Y., Hughes-Jones, N. C., Beolet, M., D'Ambrosio, A.-M., Cartron, J. P., and Le Van Kim, C. Transcript analysis of D category phenotypes predicts hybrid Rh D-CE-D proteins associated with alteration of D epitopes. *Blood* 85:2937-2944, 1995), two aberrant RHD alleles in which exons 4 to 7 derived from RHD. We reasoned that the N152T substitution might have antedated the substitution of RHD exons 4 o 7 in Cde$^s$. In this case, the 5' breakpoint region was expected to be located in intron 3 rather than exon 3 as predicted from the cDNA. We hence evaluated the presence of RHD specific polymorphisms in Cde$^s$ intron 3.

To evaluate the presence of the EcoRV-site at nucleotide position 752 (RHD specific) and 2872 (RHCE specific) and of the PvuII-site at nucleotide position 1777 (RHCE specific), the 5' part of intron 3 of RHD and RHCE was amplified using primers rb3 and rb33 and digested with EcoRV or PvuII. To evaluate the presence of the SacI-site at nucleotide position 7797 (RHCE specific) and of the Alw44I-site at nucleotide position 8550 (RHD specific), the 3' part of intron 3 of RHD and RHCE was amplified using primers rb34 and rb5 and digested with SacI or Alw44I. Primer sequences were rb3, aaggtcaacttggcgcagttggtgg (SEQ ID NO.:81); rb33, gtgagactgagttctgtattctgg (SEQ ID NO.:82); rb34, ccagaatacagaactcagtctcac (SEQ ID NO.:83); rb5, ggcagacaaactgggtatcgttgc (SEQ ID NO.:84).

The PCR-RFLP analysis of these intron 3 polymorphisms indicated that RHD specific sequences were present at least up to intron 3 position 2872. To further determine the 5' breakpoint region of Cde$^s$, we sequenced a DNA stretch encompassing the breakpoint region. DNA was amplified using primers rb3 and re37 and sequenced using primers rb33, rb34 and Cdesf1. Primer sequences were re37, gggttaaagtcacatacacagatg (SEQ ID NO.:85); Cdesf1, atacagaactcagtctcacaacttag (SEQ ID NO.:86). We determined that the breakpoint region was located in intron 3 as shown in FIG. 12.

Example 16

3' Breakpoint Region of Cde$^s$ in Intron 7

To determine the 3' breakpoint region of Cde$^s$ in intron 7, we sequenced parts of intron 7. DNA was amplified using sense primers rb8, re77 and rex1 and antisense primers rb51 and re711b. Primers rb43, rex19c, cdes7b2, and cdes7f2 were used for nucleotide sequencing. Primer sequences were rb8, gtgttgtaaccgagtgctgggg (SEQ ID NO.:87); re77, tctccacagctccatcatgggg (SEQ ID NO.:88); rex1, ggctgtaaaaatggctgaagcag (SEQ ID NO.:89); rb51, gcatgacgtgttctgcctcttg (SEQ ID NO.:90); re711b, ctatcagcattctgatctcaacg (SEQ ID NO.:91); rb43, rb43, gaatagcagagaaaacctcagactgcc (SEQ ID NO.:92); rex19c, gctccattcttgacaatacaggc (SEQ ID NO.:93); cdes7b2, gcttatactatataagttgggtttttgg (SEQ ID NO.:94); cdes7f2, gtttgaatcccaagagccactcat (SEQ ID NO.:95). We established the breakpoint region as shown in FIG. 13. The structure of the 3' breakpoint region was intriguing, because there were multiple switches between RHCE and RHD specific sequences. Those features are unusual for a breakpoint region and may be used for specific diagnosis of Cde$^s$. They may indicate that the parental alleles differed from the standard RHCE and RHD sequences or that after the major gene conversion, additional small gene conversions were introduced.

Example 17

A PCR-SSP to Specifically Detect Cde$^s$

Usually, the presence of Cde$^s$ is identified by the RHD-CE-D hybrid pattern in an RHD exon specific PCR. Such an approach does not allow the specific detection of the D negative Cde$^s$ haplotype, if an RHD positive haplotype occurs in trans. Since Cde$^s$ does not contain a hybrid Rhesus box, a RHD/Cde$^s$ heterozygous person is likely mistyped as RHD$^+$/RHD$^+$ homozygous. There are several distinct features of Cde$^s$ in the promoter, intron 2, exon 2, and exon 3 that might be used for a specific detection. These features are, however, shared by the D positive alleles D category IVa and partially by D category III type IV, which would hence confound such methods of detection.

Based on the Cde$^s$ specific DNA sequence in intron 7, we developed a PCR-SSP that specifically detected Cde$^s$. The 3' breakpoint region of Cde$^s$ in intron 7 was detected by PCR-SSP using specific primers Cdes7f2 and Cdes7b2 at 0.4 μM and HGH control primers at 0.15 μM. The other PCR conditions were identical as described in example 12. Primer sequences were Cdes7f2, gtttgaatcccaagagccactcat (SEQ ID NO.:95); Cdes7b2, gcttatactatataagttgggtttttgg (SEQ ID NO.:94). We obtained a specific product with the index Cde$^s$ sample (FIG. 14), two additional Cde$^s$ samples and a RHDΨ/Cde$^s$ heterozygous sample (FIG. 14). Normal RHD positive and RHD negative samples as well as samples of D category III type IV and of D category IVa did not result in a specific PCR product (FIG. 14). We concluded that our PCR-SSP method allowed a specific detection of Cde$^s$, even if it occurred in trans to another RHD positive allele. Furthermore, the detection method was not confounded by D category III type IV or D category IVa that shared the N152T substitution with Cde$^s$. It should be noted that the latter haplotypes are frequent in populations comprising African ethnic background, in which Cde$^s$ is prevalent. The method described by us in this example allowed the specific detection of Cde$^s$, is not confounded by the other haplotypes and hence represents a considerable improvement to the prior art. Our characterization of the 5' breakpoint region (example 15) will likewise allow the specific detection of Cde$^s$ by any suitable method known in the art, like PCR-SSP, PCR-LP, PCR-RFLP, PCR-SSO, Southern blotting etc.

The specific detection of Cde$^s$ is also important for the correct prediction of the antigen C. The RHD gene of Cde$^s$ encodes for an antigen C that is often missed in DNA based methods for the prediction of antigen C.

Example 18

Immunohematology

One sample of each RHD positive allele was evaluated by direct agglutination with two monoclonal anti-D (Seraclon anti-D, clone BS226; Biotest, Dreieich, Germany, and Frekaklon anti-D, clone MS201; Gull, Bad Homburg, Germany). Indirect antiglobulin test was done in a gel matrix test (LISS-Coombs 37° C., DiaMed-ID Micro Typing System, DiaMed, Cressier sur Morat, Switzerland) using an oligoclonal anti-D (Seraclon anti-D blend, clones H41 11B7, BS221 and BS232; Biotest). Samples reactive in gel matrix technique were further investigated using the monoclonal anti-D HM10, HM16, P3x61, P3x35, P3x212 11F1, P3x212 23B10, P3x241, P3x249, P3x290 (Diagast, Loos, France) and H41 11B7 (Biotest). The presence of a $D_{el}$ phenotype was determined by adsorption of 500 μl of a polyclonal anti-D (Human incomplete anti-D; Lorne Laboratories, Reading, UK) to 500 μl red cells for 1 h at 37° C. and elution using a chloroform technique (Flegel, Transfusion 40:428-434, 2000). The analysis of samples routinely grouped as D negative revealed 16 $D_{el}$ samples and 3 D positive samples with weak or partial D. These samples clustered among samples previously believed to be D negative with a C or E (Table 9). Nineteen of twenty-seven discrepancies between routine serology and a PCR testing intron 4 and exon 7 represented D positive samples missed by serology, only eight were due to false-positive PCR.

Example 19

Haplotype Frequencies

For alleles observed more than once, their haplotype association was trivial. Alleles that were observed only once were assumed to be associated with the Cde or cdE haplotype rather than the cde haplotype, because no RHD positive allele was detected in any ccddee sample. An allele occurring in a single CcddEe sample was formally counted half for Cde and half for cdE. CCddee samples were assumed to harbour one aberrant and one normal Cde allele. The frequency of a given aberrant RHD allele in its haplotype was calculated as the number of observed samples divided by the number of the corresponding haplotypes under observation (500 Cde, 302 cdE). The population frequency of an RHD allele was calculated from the frequency of this allele in its haplotype and the known frequency of the haplotype in the local population (Wagner, Infusionsther. Transfusionsmed. 22:285-90, 1995). The haplotype frequencies were calculated for each PCR pattern and for each RHD allele (Table 8). In accordance with a previous study in England by Avent et al. (Avent, Blood 89:2568-77, 1997), 4.9% of Cde haplotypes and 1.5% of cdE haplotypes were RHD positive in our population. As no RHD positive allele was detected among 314 ccddee samples, the frequency in the cde haplotype was less than 0.5% (upper limit of one-sided 95% confidence interval, Poisson distribution). The three frequencies differed statistically significantly from each other ($p<0.05$; two sided Fisher's exact test for each pairwise comparison corrected according to Bonferoni-Holm). The population frequency of any D negative RHD positive haplotype was estimated to be 1:1,606. $D_{el}$ alleles could only be observed in the presumed Cde haplotypes. About 3% of samples carrying antigen C that were typed D-negative in the blood bank routine represented $D_{el}$. The population frequency of $D_{el}$ alleles was 1:3,030.

TABLE 1

| Primers | | | |
|---|---|---|---|
| Primer | Nucleotide sequence | Localization | Position |
| rb10b | ggctaaatattttgatgaccaagtt | RHD cDNA | 1,194 to 1,217 |
| re011d | gcagccaacttcccctgtg | RHD promoter | −883 to −901 |
| re014 | gctctaccttggtcacctcc | dJ469D22 | 52,189 to 52,209 |
| re04 | aggtcacatccatttatcccactg | dJ469D22 | 53, 968 to 53,945 |
| re11d | agaagatgggggaatctttttcct | dJ469D22 | 51,193 to 51,216 |
| re96 | ttgtgactgggctagaaagaaggtg | dJ469D22 | 242 to 216 |
| rea7 | tgttgcctgcatttgtacgtgag | RHD cDNA | 1,311 to 1,333 |
| rend31 | ttctgtctgggttggggaggg | dJ465N24 | 128,649 to 128,629 |
| rend32 | ggaggggttaatatgggtggc | dJ465N24 | 127,355 to 127,375 |
| rend8b1 | tttgtcctggttgcctgtggtc | dJ465N24 | 69,296 to 69,274 |
| rend8b2 | caaatcctgttgactggtctcgg | dJ465N24 | 68,451 to 68,473 |
| rend9a1 | aacggctccatcacccctaaag | dJ465N24 | 50,008 to 49,987 |
| rend9a2 | cccactcctagataccaacccaag | dJ465N24 | 49,059 to 49,083 |
| rey14a | ctttatgcactgcctcgttgaatc | dJ469D22 | 56,792 to 56,769 |
| rey14b | ttgactggtgtggttgctgttg | dJ469D22 | 55,863 to 55,884 |
| rey15a | gcagaaaggggagttgatgctg | dJ469D22 | 55,416 to 55,395 |
| rey7 | ctgacaaagttgagagcccactg | dJ469D22 | 62,324 to 62,346 |
| rey8 | ttaagcctacatccacatgctgag | dJ469D22 | 62,854 to 62,831 |
| rez2 | ccttggtctgccagaattttca | RHD cDNA | 2738 to 2717 |
| rez4 | gtttggcatcataggagatttggc | dJ465N24 | 120,101 to 120,124 |
| rez7 | cctgtccccatgattcagttacc | dJ465N24 | 124,831 to 124,854 |
| rh7 | acgtacaaatgcaggcaac | RHD cDNA | 1,330 to 1,312 |
| rnb31 | cctttttttgtttgtttttggcggtgc | downstream Rhesus box | 6,710 to 6,684 |
| rr4 | agcttactggatgaccacca | RHD cDNA | 1,541 to 1,522 |
| sf1 | gactgggggaaaagcgcaatac | SMP1 cDNA | 142 to 164 |
| sf1c | gtattgcgcttttccccccagtc | SMP1 cDNA | 164 to 142 |
| sf3 | tgacttgctctcatcccacatg | SMP1 cDNA | 1,696 to 1,717 |
| sm19 | gggcttgaagcaagtaaatggaag | SMP1 intron 1 | −58 to −35 |
| sr1 | gctatcaatattttcttggttacagacac | SMP1 cDNA | 2,172 to 2,144 |
| sr3 | gttcactgccataagtcttcagtgc | SMP1 cDNA | 575 to 551 |
| sr3kp | tggccgcactgaagacttatgg | SMP1 cDNA | 546 to 567 |
| sr45 | cagctgcatctatgataatccacc | SMP1 cDNA | 224 to243 |
| sr47 | atggacaagtccgaggtgatag | SMP1 cDNA | 315 to 344 |
| sr47c | atcacctcggacttgtccattc | SMP1 cDNA | 342 to 321 |
| sr5 | gcaatcagagatccaaaggccaac | SMP1 cDNA | 428 to 405 |
| sr5c | gttggcctttggatctctgattgc | SMP1 cDNA | 405 to 428 |
| sr55 | gacatagtataccctggaattgctgt | SMP1 cDNA | 472 to 497 |
| sr55c | acagcaattccagggtatactatgtc | SMP1 cDNA | 497 to 472 |
| sr9 | ctcccccgattttagccaagaa | SMP1 cDNA | 27 to 6 |

For the RHD promoter and the RHD cDNA, the positions refer to the distance from the A of the start codon. For introns, they refer to the distance from the intron/exon junction. For all other sequences including the SMP1 cDNA, they refer to the distance from the start of the published sequences. The mismatches in primers reyl4b, rnb31, and sf3 were inadvertently introduced. Primers re11d, re014 and re04 do not exactly match dJ469D22, because they were designed from our raw sequences covering the 5' flanking region of RHD.

TABLE 2

| Presence of RHD flanking sequences in the YAC 38A-A10 | | | | | | | |
|---|---|---|---|---|---|---|---|
| | | | | | Amplicons obtained with | | |
| Primer | | | | Amplicon | Genomic DNA | | YAC |
| sense | antisense | Predicted position | | size | $RHD^+$ | $RHD^-$ | 38A-A10 |
| rend9a1 | rend9a2 | RHD 5' flanking region | about 85,000 bp from ATG | 948 bp | yes | yes | yes |
| rend8b1 | rend8b2 | RHD 5' flanking region | about 50,000 bp from ATG | 845 bp | yes | yes | yes |
| rea7 | rez2 | RHD 3' flanking region | about 1,500 bp from STOP | 1,412 bp | yes | no | yes |
| rend32 | sr9 | RHCE 3' flanking region | about 20,000 bp from STOP | 1,989 bp | yes | yes | yes |
| sr1 | sf3 | RHCE 3' flanking region | about 1,000 bp from STOP | 477 bp | yes | yes | yes |
| rey14b | rey14a | RHCE 5' flanking region | about 5,300 bp from ATG | 929 bp | yes | yes | no |
| rey7 | rey8 | RHCE 5' flanking region | about 10,000 bp from ATG | 530 bp | yes | yes | no |

TABLE 3

| PCR-RFLP for the specific detection of the RHD deletion | | | | | | | | | |
|---|---|---|---|---|---|---|---|---|---|
| | | | Number of samples with RHD genotype | | | | | | |
| Pheno- | Known | Samples | determined | | | expected* | | | |
| type | genotype | tested (n) | +/+ | +/− | −/− | +/+ | +/− | −/− | P¶ |
| Known genotype | | | | | | | | | |
| ccddee | cde/cde | 14 | 0 | 0 | 14 | 0 | 0 | 14 | N.A. |
| CCddee | Cde/Cde† | 5 | 0 | 0 | 5 | 0 | 0 | 5 | N.A. |
| ccddEE | cdE/cdE† | 1 | 0 | 0 | 1 | 0 | 0 | 1 | N.A. |
| D variants | D/cde‡ | 9 | 0 | 9 | 0 | 0 | 9 | 0 | N.A. |
| ccDEe | cDe/cDE§ | 4 | 4 | 0 | 0 | 4 | 0 | 0 | N.A. |
| Common phenotypes | | | | | | | | | |
| CcDee | | 10 | 1 | 9 | 0 | 0.5 | 9.5 | 0 | >0.4 |
| ccDEe | | 10 | 0 | 10 | 0 | 0.3 | 9.7 | 0 | >0.5 |
| ccDee | | 10 | 1 | 9 | 0 | 0.5 | 9.5 | 0 | >0.4 |

TABLE 3-continued

| PCR-RFLP for the specific detection of the RHD deletion | | | | | | | | | |
|---|---|---|---|---|---|---|---|---|---|
| | | | Number of samples with RHD genotype | | | | | | |
| Pheno- | Known | Samples | determined | | | expected* | | | |
| type | genotype | tested (n) | +/+ | +/− | −/− | +/+ | +/− | −/− | P¶ |
| CCDee | | 10 | 9 | 1 | 0 | 9.5 | 0.5 | 0 | >0.4 |
| CcDEe | | 12 | 11 | 1 | 0 | 11 | 1 | 0 | >0.5 |
| ccDEE | | 10 | 10 | 0 | 0 | 9.2 | 0.8 | 0 | >0.4 |
| CCDEe | | 6 | 5 | 1 | 0 | 5.8 | 0.2 | 0 | >0.1 |

*Expected number of $RHD^+/RHD^+$ and $RHD^+/RHD^-$ samples based on known genotypes or the haplotype frequencies in the local population [41]

†RHD-negative in PCR.

‡$RHD^+/RHD^-$, because a weak or partial D phenotype would be masked in a $RHD^+/RHD^+$ gentoype. These samples were weak D type 1 (n = 2), type 2 (n = 2), type 3 (n = 2), type 4 (n = 2) and $D^{VII}$ (n = 1).

§Presence of two RHD genes differing in their polymorphic HaeIII-site in intron 3 [42] demonstrated by PCR-RFLP.

N.A.—not applicable. Probabilities were calculated based on confidence limits of binomial distribution.

TABLE 4

| RHD PCR-SSP: (SEQ ID NOs: 96, 29, 97-101, 69, 102-105, 67, 68, 106-111, 34, 112) | | | | | | | |
|---|---|---|---|---|---|---|---|
| Region | Name* Reference | DNA sequence | Position | | Polymorphisms detected | Amplicon size | |
| Promoter | re012 | tccactttccacctccctgc | Promoter | −1,137 to −1,119 | 7 bp deletion at −1125 | 255 | 43 |
| | re011d | gcagccaacttcccctgtg | Promoter | −883 to −901 | 4 bp deletion at −896 | | 44 |
| Exon 3 | ga31 (D-3-383) | ttgtcggtgctgatctcagtgga | Exon 3 | 361 to 383 | 383 A | 154 | 21 |
| | rb21 | aggtccctcctccagcac | Intron 3 | 28 to 11 | | | 42 |
| Exon 4 | ga41 (D-4-527) | acatgatgcacatctacgtgttcgc | Exon 4 | 503 to 527 | | 123 | 21 |
| | ga42 (D-4-602) | cagacaaactgggtatcgttgctg | Exon 4 | 625 to 602 | 602 C | | 21 |
| Intron 4 | re41 | cgatacccagtttgtctgccatgc | Exon 4 | 608 to 631 | | 226 | this study |
| | rb12 | tcctgaacctgctctgtgaagtgc | Intron 4 | 198 to 175 | Intron 4 deletion in RHD | | 40 |
| Exon 5 | rb24 | agacctttggagcaggagtg | Intron 4 | −53 to −34 | | 228 | 40 |
| | ga51 (D-5-787) | ctgctcaccttgctgatcttccc | Intron 5/Exon 5 | | 8 to 787 | 787 G | 21 |
| Exon 6 | ga62 (D-6-826) | ttatgtgcacagtgcggtgttgg | Exon 6 | 804 to 826 | | 133 | 21 |
| | ga61 (D-6-916) | caggtacttggctcccccgac | Exon 6 | 936 to 916 | 916 G | | 21 |
| Exon 7† | ga71 (D-7-967) | gttgtaaccgagtgctggggattc | Exon 7 | 944 to 967 | | 123 | 21 |
| | ga72 (D-7-1048) | tgccggctccgacggtatc | Exon 7 | 1,066 to 1,048 | 1,048 G | | 21 |
| Exon 7† | rb26 | aggggtgggtagggaatatg | Intron 6 | −62 to −43 | | 130 | 42 |
| | re71 | acccagcaagctgaagttgtagcc | Exon 7 | 1,008 to 985 | 985/986 GG | | 42 |
| Intron 7 | rb52 | ccaggttgttaagcattgctgtacc | Intron 7 | 6,666 to 6,690 | 6,690 C | | 42 |
| | rb51 | gcatgacgtgttctgcctcttg | Intron 7 | 6,734 to 6,713 | 6,713 C | 169 | this study |
| Exon 9 | re83 | gagattaaaaatcctgtgctcca | Intron 8 | −56 to −34 | | 119 | 42 |
| | re94 | cttggtcatcaaaatatttagcct | Exon 9 | 1,216 to 1,193 | 1,193 A | | this study |

TABLE 4-continued

| RHD PCR-SSP: (SEQ ID NOs: 96, 29, 97-101, 69, 102-105, 67, 68, 106-111, 34, 112) | | | | | | | |
|---|---|---|---|---|---|---|---|
| Region | Name* Reference | DNA sequence | Position | | Polymorphisms detected | Amplicon size | |
| Exon 10 (3' UTR) | rea7 | tgttgcctgcatttgtacgtgag | 3'UTR | 1,310 to 1,333 | RHD/Rhesus box | 23 | 44 |
| | rr4 | agcttactggatgaccacca | 3'UTR | 1,541 to 1,522 | junction | | 42 |

*Primer names in brackets are as described by Gassner et al. [21].

†Primer set ga71/ga72 was used for the screening, primer set rb26-re71 for RHD exon specific PCR-SSP.

TABLE 5

| Population survey of known D negative blood donors screened by RHD PCR-SSP | | |
|---|---|---|
| Documented | Samples (n) | |
| phenotype | screened | PCR-SSP positive* |
| ccddee | 314 | 0 |
| Ccddee | 433 | 34 |
| ccddEe | 271 | 5 |
| CCddee | 24 | 4 |
| CcddEe | 19 | 4 |
| ccddEE | 6 | 1 |
| CcddEE | 1 | 0 |
| Total | 1,068 | 48 |

*Positive for at least one of four RHD specific polymorphisms tested (promoter, intron 4, exon 7 or 3' UTR).

TABLE 6

| PCR patterns compatible with RHD-RHCE-RHD hybrid genes or partial RHD deletions in 25 D negative samples | | | | | | | | | | | | | | | |
|---|---|---|---|---|---|---|---|---|---|---|---|---|---|---|---|
| PCR | RHD specific PCR-SSP* | | | | | | | | | | Samples | Phenotype | | Haplo- | |
| pattern | P | E3 | E4 | I4 | E5 | E6 | E7 | I7 | E9 | E10 | Possible cause† | (n) | Documented | Confirmed | type | Reference‡ |
| Pattern 1 | + | − | − | − | − | − | − | − | − | + | RHD-CE(3-9)-D | 11 | Ccddee§ | D negative | Cde | Whites [1,25], Africans [24] |
| Pattern 2 | + | − | − | − | − | − | − | − | + | + | RHD-CE(3-7)-D | 4 | Ccddee | D negative | Cde | this study |
| Pattern 3 | + | + | − | − | − | − | − | − | + | + | RHD-CE(4-7)-D | 3 | ccddEe | D negative | cdE | Whites [16] |
| Pattern 4 | + | + | − | − | − | − | − | + | + | + | RHD-CE(4-7)-D | 1 | CcddEe | D negative | n.k.¶ | this study |
| Pattern 5 | + | + | − | − | − | + | + | + | + | + | RHD-CE(4-5)-D | 2 | ccddEe$^{\alpha}$ | partial D/$D_{el}$$^{\alpha}$ | cDE | Whites [3,22,30,40] |
| Pattern 6 | + | + | + | + | + | + | + | − | − | + | RHD-CE(8-9)-D | 3 | CCddee | D negative | Cde | Whites [21] |
| Pattern 7 | − | − | − | − | − | − | − | − | − | + | RHCE(1-9)-D(10) | 1 | ccddEe | D negative | cdE | this study |
| Pattern 8 | − | + | − | − | − | − | − | + | + | + | RHD(1-3)-CE(4-7)-D | 1 | CcddEe | D negative | Cde$^{\beta}$ | Africans [5,15] |

*P—Promoter, E3—Exon 3, E4—Exon 4, I4—Intron 4, E5—Exon 5, E6—Exon 6; E7—Exon 7; I7—Intron 7; E9—Exon 9; E10—Exon 10 (3' UTR )

†Assuming the presence of a single RHD-CE-D hybrid allele.

‡Previously described alleles that fit PCR pattern and haplotype.

§11 samples: 9 Ccddee, 1 CCddee, 1 CcddEe

¶n.k.—not known.

$^{\alpha}$2 samples, 1 labeled CcddEe with $D_{el}$ phenotype, 1 labeled ccddEe with partial D $D^{VI}$ phenotype.

$^{\beta}$Probably identical to $Cde^{s}$ (see below).

TABLE 7

| RHD alleles with single nucleotide substitutions in 22 D negative samples | | | | | | | |
|---|---|---|---|---|---|---|---|
| | Substitution | | Samples | Phenotype | | | |
| Allele | Reference | Effect(s) | (n) | Documented | Confirmed | Haplotype | |
| RHD(W16X) | G->A at 48 | Stop codon at codon 16 | 2 | Ccddee | D negative | Cde | this study |
| RHD(G486(+1)A) | g->a at 486 + 1 | 5' splice site intron 3 ACgt->ACat | 3 | Ccddee | $D_{el}$ | CDe | this study |
| RHD(G212V) | G->T at 635 | 3' splice site intron 4 agGC->agTC Missense mutation G212V | 1 | Ccddee | D negative | Cde | this study |
| RHD(C285Y) | G->A at 854 | Missense mutation C285Y | 1 | ccddEe | partial D* | cDE | this study[1] |

TABLE 7-continued

RHD alleles with single nucleotide substitutions in 22 D negative samples

| Allele | Substitution Reference | Effect(s) | Samples (n) | Phenotype Documented | Phenotype Confirmed | Haplotype | |
|---|---|---|---|---|---|---|---|
| RHD(M295I) | G->T at 885 | Missense mutation M295I | 7 | Ccddee | $D_{el}$ | CDe† | 42 |
| RHD(Y330X) | C->G at 985 | Stop codon at codon 330 | 1 | Ccddee | D negative | Cde | this study |
| RHD(G1153(+1)A) | g->a at 1153 + 1 | 5' splice site intron 8 AGgt->AGat | 1 | Ccddee | D negative | Cde | this study |
| RHD(G385A) | G->C at 1154 | 3' splice site intron 8 agGT->agCT Missense mutation G385A | 1 | CcddEe | weak D | cDE | 42 |
| RHD(K409K) | G->A at 1227 | 5' splice site intron 9 AGgt->AAgt | 5 | Ccddee | $D_{el}$ | CDe | this study |

*A detailed serologic analysis of this sample representing the partial D DIM has been published previously [43].

†The same allele occurring in a cDe haplotype has been described as weak D type 11.

TABLE 8

Estimated frequencies in population

| PCR pattern/Allele | Frequency among Cde/cdE | Frequency in population |
|---|---|---|
| Pattern 1 | 1:45 | 1:4,132 |
| Pattern 2 | 1:125 | 1:11,364 |
| Pattern 3 | 1:101 | 1:17,976 |
| Pattern 4 | 1:500* | 1:45,455* |
| Pattern 6 | 1:167 | 1:15,152 |
| Pattern 7 | 1:302 | 1:53,929 |
| Pattern 8 | 1:500 | 1:45,455 |
| RHD(W16X) | 1:250 | 1:22,727 |
| RHD(G212V) | 1:500 | 1:45,455 |
| RHD(Y330X) | 1:500 | 1:45,455 |
| RHD(G1153(+1)A) | 1:500 | 1:45,455 |
| Any D negative | 1:20/1:67† | 1:1,607 |
| RHD(G486(+1)A) | 1:167 | 1:15,152 |
| RHD(M295I) | 1:71 | 1:6,493 |
| RHD(K409K) | 1:100 | 1:9,091 |
| Any $D_{el}$ | 1:33‡ | 1:3,030 |

*Assuming a Cde haplotype; a cdE haplotype would result in a frequency of 1:302 among cdE and 1:53,929 in the population. For statistics and sum frequencies, the haplotype was formally counted as 0.5 Cde and 0.5 cdE.

†1:20 among Cde, 1:67 among cdE.

‡1:33 relative to the Cde haplotype.

TABLE 9

False negative rate in routine typing for antigen D

| Documented Phenotype | Samples (n) | Confirmed phenotype (n) $D_{el}$ | Confirmed phenotype (n) partial or weak D | False negatives n | False negatives Rate |
|---|---|---|---|---|---|
| ccddee | 314 | 0 | 0 | 0 | 0%† |
| Ccddee | 433 | 15 | 0 | 15 | 3.5% |
| ccddEe | 271 | 0 | 2 | 2 | 0.7% |
| other* | 50 | 1 | 1 | 2 | 4% |
| D negative | N.A.‡ | 0.15% | 0.02% | | 0.17% |

*CCddee, CcddEe, ccddEE, and CCddEe

†Upper limit of 95% confidence interval was 0.95% (Poisson distribution)

‡N.A. - not applicable. The frequencies are estimates based on the phenotype frequencies in the population 41.

TABLE 10

Previously described D negative, RHD positive alleles

| Allele | Haplotype | Population | Possible match |
|---|---|---|---|
| RHD(Q41X) [2] | Cde | Whites | not detected |
| RHD-CE(2-9)-D [1,24,25] | Cde | Whites[1,25], Blacks[24] | Pattern 1 |
| RHD-CE(3:455-7)-D [5,15] | Cdes | Blacks | Pattern 8 |
| RHD(488del4) [1] | Cde | Whites | not detected |
| RHD-CE(4-7)-D [16] | cdE | Whites | Pattern 3 or 4 |
| RHDΨ [38] | cde | Blacks | not detected |
| RHD(600del) [10] | Cde | somatic mutation* | not detected |
| RHD (exon 5 variant) [8] | cde | not communicated | not detected |
| RHD(G314V) [34] | Cde | Japanese | not detected |
| RHD(exon 9 variant) | Cde | Whites | Pattern 6 |

*Allele acquired by somatic mutation in a woman with chronic myelogenic leucemia and restricted to the myeloid lineage

TABLE 11

Population rates of false positives and positive predictive value of different RHDPCR strategies

| PCR strategy | Rate of false positives | Positive predictive value of positive result | Number of polymorphism tested |
|---|---|---|---|
| Exon 10 only | 1:1,275 | 0.999216 | 1 |
| Intron 4/Exon 7 | 1:4,081 | 0.999755 | 2 |
| Intron 4/Exon 7/RHDΨ | 1:4,700 | 0.999787 | 3 |
| Intron 4/Exon 7/VV16X | 1:5,212 | 0.999808 | 3 |
| Intron 4/Exon 7/Intron 7 | 1:6,051 | 0.999835 | 3 |
| Exons 3, 4, 5, 6, 7, 9 | 1:6,051 | 0.999835 | 6 |
| Exons 2, 3, 4, 5, 6, 7, 9, 10 | 1:6,051 | 0.999835 | 8 |
| Intron 4/Exon 7/W16X/RHDΨ | 1:6,267 | 0.999840 | 4 |
| All Exons/RHDΨ | 1:7,520 | 0.999867 | 9 |
| Intron 4/Exon 7/ Intron 7/W16X | 1:8,921 | 0.999888 | 4 |
| Intron 4/Exon 7/ Intron 7/W16X/RHDΨ | 1:12,533 | 0.999920 | 5 |

REFERENCES

1. Andrews K T, Wolter L C, Saul A, Hyland C A: The RhD-trait in a white patient with the RhCCee phenotype attributed to a four-nucleotide deletion in the RHD gene. Blood 92:1839, 1998

2. Avent N D, Martin P G, Armstrong-Fisher S S, Liu W, Finning K M, Maddocks D, Urbaniak S J: Evidence of genetic diversity underlying Rh D negative, weak D ($D^u$) and partial D phenotypes as determined by multiplex PCR analysis of the RHD gene. Blood 89:2568, 1997

3. Avent N D, Liu W, Jones J W, Scott M L, Voak D, Pisacka M, Watt J, Fletcher A. Molecular analysis of Rh transcripts and polypeptides from individuals expressing the $D^{VI}$ variant phenotype: an RHD gene deletion event does not generate all $D^{VI}$ccEe phenotypes. Blood 1997; 89:1779-86.

4. Blumenfeld O O, Huang C H: Molecular genetics of the glycophorin gene family, the antigens for MNSs blood groups: multiple gene rearrangements and modulation of splice site usage result in extensive diversification. Hum Mutat 6:199, 1995
5. Blunt T, Daniels G, Carritt B: Serotype switching in a partially deleted RHD gene. Vox Sang 67:397, 1994
6. Bowman J: The management of hemolytic disease in the fetus and newborn. Semin Perinatol 21:39, 1997
7. Carritt B, Kemp T J, Poulter M: Evolution of the human RH (rhesus) blood group genes: a 50 year old prediction (partially) fulfilled. Hum Mol Genet 6:843, 1997
8. Carritt B, Steers F J, Avent N D. Prenatal determination of fetal RhD type. Lancet 1994; 344:205-6.
9. Cherif-Zahar B, Mattel M G, Le Van Kim C, Bailly P, Cartron J P, Colin Y: Localization of the human Rh blood group gene structure to chromosome region 1p34.3-1p36.1 by in situ hybridization. Hum Genet 86:398, 1991
10. Cherif-Zahar B, Bony V, Steffensen R, Gane P, Raynal V, Goosens D, Laursen J S, Varming K, Jersild C, Cartron J P. Shift from Rh-positive to Rh-negative phenotype caused by a somatic mutation within the RHD gene in a patient with chronic myelocytic leukaemia. Br J Haematol 1998; 102:1263-70.
11. Colin Y, Cherif-Zahar B, Le Van Kim C, Raynal V, van Huffel V, Cartron J-P. Genetic basis of the RhD-positive and RhD-negative blood group polymorphism as determined by southern analysis. Blood 1991; 78:2747-52.
12. Cossu G, Angius A, Gelfi C, Righetti P G: Rh D/d genotyping by quantitative polymerase chain reaction and capillary zone electrophoresis. Electrophoresis 17:1911, 1996
13. Daniels G L, Faas B H, Green C A, Smart E, Maaskant-van Wijk P A, Avent N D, Zondervan H A, von dem Borne A E, van der Schoot C E. The VS and V blood group polymorphisms in Africans: a serologic and molecular analysis. Transfusion 1998; 38:951-8.
14. Döscher A, Schunter F, Müller T H: Quantitativae PCR to assess RHD zygosity. Infusionsther Transfusionsmed 26(suppl 1):31, 1999 (abstr.)
15. Faas B H W, Becker E A M, Wildoer P, Ligthart P C, Overbeeke M A M, Zondervan H A, von dem Borne A E G K, van der Schoot C E: Molecular background of VS and weak C expression in blacks. Transfusion 37:38, 1997
16. Faas B H W, Beckers E A M, Simsek S, Overbeeke M A M, Pepper R, van Rhenen D J, von dem Borne A E G K, van der Schoot C E: Involvement of Ser103 of the Rh polypeptides in G epitope formation. Transfusion 36:506, 1996
17. Filbey D, Hanson U, Wesstrom G: The prevalence of red cell antibodies in pregnancy correlated to the outcome of the newborn: a 12 year study in central Sweden. Acta Obstet Gynecol Scand 74:687, 1995
18. Flegel W A, Khull S R, Wagner F F. Primary anti-D immunization by weak D type 2 RBCs. Transfusion 2000; 40: 428-434
19. Flegel W A, Wagner F F, Gassner C: Rh phenotype prediction by DNA typing and its application to practice. Transfus Med 8:281, 1998
20. Fujiwara H, Okuda H, Omi T, Iwamoto S, Tanaka Y, Takahashi J, Tani Y, Minakami H, Araki S, Sato I, Kajii E: The STR polymorphisms in intron 8 may provide information about the molecular evolution of RH haplotypes. Hum Genet 104:301, 1999
21. Gassner C, Schmarda A, Kilga-Nogler S, Jenny-Feldkircher B, Rainer E, Müller T H, Wagner F F, Flegel W A, Schönitzer D: RhesusD/CE typing by polymerase chain reaction using sequence-specific primers. Transfusion 37:1020, 1997
22. Huang C H. Human $D^{VI}$ category erythrocytes: correlation of the phenotype with a novel hybrid RhD-CE-D gene but not an internally deleted RhD gene. Blood 1997; 89:1834-9.
23. Huang C H, Reid M E, Chen Y, Coghlan G, Okubo Y: Molecular definition of red cell Rh haplotypes by tightly linked SphI RFLPs. Am J Hum Genet 58:133, 1996
24. Huang C H: Alteration of RH gene structure and expression in human dCCee and DCW-red blood cells: phenotypic homozygosity versus genotypic heterozygosity. Blood 88:2326, 1996
25. Hyland C A, Wolter L C, Saul A. Three unrelated Rh D gene polymorphisms identified among blood donors with Rhesus CCee (r'r') phenotypes. Blood 1994; 84:321-4.
26. Kemp T J, Poulter M, Carritt B: Microsatellite variation within the human RHCE gene. Vox Sang 77:159, 1999
27. Lo Y-MD, Bowell P J, Selinger M, Mackenzie I Z, Chamberlain P, Gillmer M D G, Littlewood T J, Fleming K A, Wainscoat J S: Prenatal determination of fetal RhD status by analysis of peripheral blood of rhesus negative mothers. Lancet 341:1147, 1993
28. Maaskant-van Wijk P A, Hemker M B, Douglas-Berger L, et al. Ethnic variability of the Rhesus system. Transfusion 1999; 39:(10S)103S-4S (Abstract).
29. Maaskant-van Wijk P A, Faas B H W, de Ruijter J A M, Overbeeke M A M, von dem Borne A E G K, van Rhenen D J, van der Schoot C E. Genotyping of RHD by multiplex polymerase chain reaction analysis of six RHD-specific exons. Transfusion 1998; 38:1015-21.
30. Maaskant-van Wijk P A, Beckers E A M, van Rhenen D J, Mouro I, Colin Y, Cartron J-P, Faas B H W, van der Schoot C E, Apoil P A, Blancher A, et al. Evidence that the RHD (VI) deletion genotype does not exist. Blood 1997; 90:1709-11.
31. MacGeoch C, Mitchell C J, Carritt B, Avent N D, Ridgwell K, Tanner M J, Spurr N K: Assignment of the chromosomal locus of the human 30-kDal Rh (rhesus) blood group-antigen-related protein (Rh30A) to chromosome region 1p36.13 - - - - p34. Cytogenet Cell Genet 59:261, 1992
32. Mourant A E, Kopec A C, Domaniewska-Sobczak K: The distribution of the human blood groups and other polymorphisms. London, Oxford University Press, 1976
33. Okuda H, Suganuma H, Tsudo N, Omi T, Iwamoto S, Kajii E: Sequence analysis of the spacer region between the RHD and RHCE genes. Biochem Biophys Res Commun 263:378, 1999
34. Okuda H, Kawano M, Iwamoto S, Tanaka M, Seno T, Okubo Y, Kajii E: The RHD gene is highly detectable in RhD-negative Japanese donors. J Clin Invest 100:373, 1997
35. Onda M, Fukuda M: Detailed physical mapping of the genes encoding glycophorins A, B and E, as revealed by P1 plasmids containing human genomic DNA. Gene 159:225, 1995
36. Reboul J, Gardiner K, Monneron D, Uze G, Lutfalla G: Comparative genomic analysis of the interferon/interleukin-10 receptor gene cluster. Genome Res 9:242, 1999
37. Salvignol I, Calvas P, Socha W W, Colin Y, Le Van Kim C, Bailly P, Ruffle J, Cartron J P, Blancher A: Structural analysis of the RH-like blood group gene products in nonhuman primates. Immunogenetics 41:271, 1995
38. Singleton B K, Green C A, Avent N D, Martin P G, Smart E, Daka A, Narter-Olaga E G, Hawthorne L M, Daniels G:

The presence of an RHD pseudogene containing a 37 base pair duplication and a nonsense mutation in africans with the Rh D-negative blood group phenotype. Blood 95:12, 2000

39. Urbaniak S J, Robertson A E: A successful program of immunizing Rh-negative male volunteers for anti-D production using frozen/thawed blood. Transfusion 21:64, 1981
40. Wagner F F, Gassner C, Schönitzer D, Schunter F, Flegel W A: Three molecular structures cause Rhesus D category VI phenotypes with distinct immunohematologic features. Blood 91:2157, 1998
41. Wagner F F, Kasulke D, Kerowgan M, Flegel W A: Frequencies of the blood groups ABO, Rhesus, D category VI, Kell, and of clinically relevant high-frequency antigens in South-Western Germany. Infusionsther Transfusionsmed 22:285, 1995
42. Wagner F F, Gassner C, Müller T H, Schönitzer D, Schunter F, Flegel W A: Molecular basis of weak D phenotypes. Blood 93:385, 1999
43. Wagner F F, Frohmajer A, Ladewig B, Eicher N I, Lonicer C B, Müller T H, Siegel M H, Flegel W A. Weak D alleles express distinct phenotypes. Blood 2000; 95: 2699-2708
44. Wagner F F, Flegel W A. RHD gene deletion occurred in the Rhesus box. Blood 2000;
45. Wissenschaftlicher Beirat der Bundesärztekammer; Paul-Ehrlich-Institut. Richtlinien zur Blutgruppenbestimmung and Bluttransfusion (Hämotherapie). Köln: Deutscher Ärzte-Verlag; 1996.
46. Legler T J, Kohler M, Mayr W R, Panzer S, Ohto H, Fischer G F; Genotyping of the human platelet antigen systems 1 through 5 by multiplex polymerase chain reaction and ligation-based typing. Transfusion 1996 May; 36(5): 426-31

The invention claimed is:

1. An isolated nucleic acid molecule comprising SEQ ID NO:18 or comprising SEQ ID NO:20 hybridized to an oligonucleotide that is 12-50 nucleotides in length labelled with a non-nucleotide containing label.

2. The nucleic acid molecule of claim 1 derived from a sample comprising an RHD positive haplotype that is serologically classified RhD negative.

3. The nucleic acid molecule of claim 2, wherein said sample is obtained from a Caucasian.

4. A vector comprising SEQ ID NO:18 or comprising SEQ ID NO:20.

5. The nucleic acid molecule of claim 1, wherein the label comprises a radioactive marker, or a fluorescent, phosphorescent, chemiluminescent or enzymatic label.

* * * * *